United States Patent
Dennis et al.

(10) Patent No.: US 10,941,215 B2
(45) Date of Patent: Mar. 9, 2021

(54) LOW AFFINITY BLOOD BRAIN BARRIER RECEPTOR ANTIBODIES AND USES THEREOF

(71) Applicant: Genentech, Inc., South San Francisco, CA (US)

(72) Inventors: Mark Dennis, South San Francisco, CA (US); Ryan Jefferson Watts, South San Francisco, CA (US); Yunhua Yu Zuchero, South San Francisco, CA (US); Yin Zhang, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/131,591

(22) Filed: Sep. 14, 2018

(65) Prior Publication Data
US 2019/0202936 A1 Jul. 4, 2019

Related U.S. Application Data

(60) Continuation of application No. 15/435,658, filed on Feb. 17, 2017, now abandoned, which is a division of application No. 14/577,006, filed on Dec. 19, 2014, now Pat. No. 9,611,323, which is a continuation of application No. 13/306,524, filed on Nov. 29, 2011, now abandoned.

(60) Provisional application No. 61/418,223, filed on Nov. 30, 2010.

(51) Int. Cl.
| | |
|---|---|
| *C07K 16/46* | (2006.01) |
| *C07K 16/28* | (2006.01) |
| *C07K 16/18* | (2006.01) |
| *C07K 16/40* | (2006.01) |
| *A61K 47/68* | (2017.01) |
| *A61K 39/00* | (2006.01) |

(52) U.S. Cl.
CPC ............ *C07K 16/468* (2013.01); *C07K 16/18* (2013.01); *C07K 16/28* (2013.01); *C07K 16/2881* (2013.01); *C07K 16/40* (2013.01); *A61K 47/68* (2017.08); *A61K 2039/505* (2013.01); *C07K 2317/31* (2013.01); *C07K 2317/54* (2013.01); *C07K 2317/70* (2013.01); *C07K 2317/76* (2013.01); *C07K 2317/92* (2013.01); *Y02A 50/30* (2018.01)

(58) Field of Classification Search
CPC ...... C07K 16/18; C07K 16/468; C07K 16/28; C07K 16/2881; C07K 16/40; C07K 2317/31; C07K 2317/54; C07K 2317/70; C07K 2317/76; C07K 2317/92; A61K 47/68; A61K 2039/505
See application file for complete search history.

(56) References Cited

U.S. PATENT DOCUMENTS

| | | |
|---|---|---|
| 4,332,785 A | 6/1982 | Allen et al. |
| 4,434,156 A | 2/1984 | Trowbridge |
| 4,447,547 A | 5/1984 | Allen et al. |
| 4,545,985 A | 10/1985 | Pastan et al. |
| 4,626,507 A | 12/1986 | Trowbridge et al. |
| 4,801,575 A | 1/1989 | Pardridge et al. |
| 4,892,827 A * | 1/1990 | Pastan ................. A61P 35/00 435/193 |
| 4,956,453 A | 9/1990 | Bjorn et al. |
| 5,141,736 A | 8/1992 | Iwasa et al. |
| 5,141,743 A | 8/1992 | Schryvers |
| 5,154,924 A | 10/1992 | Friden |
| 5,182,107 A | 1/1993 | Friden |
| 5,208,021 A | 5/1993 | Johnson et al. |
| 5,217,713 A | 6/1993 | Iwasa et al. |
| 5,231,000 A | 7/1993 | Majocha et al. |
| 5,254,342 A | 10/1993 | Shen et al. |
| 5,292,869 A | 3/1994 | Schryvers |
| 5,352,447 A | 10/1994 | Johnson et al. |
| 5,360,719 A | 11/1994 | Levine et al. |
| 5,480,778 A | 1/1996 | Levine et al. |
| 5,527,527 A | 6/1996 | Friden |
| 5,601,819 A | 2/1997 | Wong et al. |
| 5,648,469 A | 7/1997 | Trowbridge et al. |
| 5,658,570 A | 8/1997 | Newman et al. |
| 5,667,781 A | 9/1997 | Trowbridge et al. |
| 5,672,683 A | 9/1997 | Friden et al. |
| 5,681,722 A | 10/1997 | Newman et al. |
| 5,693,780 A | 12/1997 | Newman et al. |
| 5,708,149 A | 1/1998 | Loosmore et al. |
| 5,728,383 A | 3/1998 | Johnson et al. |
| 5,750,105 A | 5/1998 | Newman et al. |
| 5,792,458 A | 8/1998 | Johnson et al. |

(Continued)

FOREIGN PATENT DOCUMENTS

| | | |
|---|---|---|
| CN | 101245107 B | 10/2010 |
| EP | 079696 B1 | 3/1988 |

(Continued)

OTHER PUBLICATIONS

Langmuir VK et al. Comparisons between two monoclonal antibodies that bind to the same antigen but have differing affinities: uptake kinetics and 125I-antibody therapy efficacy in multicell spheroids. Cancer Res. 52, 4728-4734. (Year: 1992).*

(Continued)

*Primary Examiner* — Kimberly Ballard
(74) *Attorney, Agent, or Firm* — McNeill Baur PLLC

(57) ABSTRACT

The present invention relates to antibodies that bind blood brain barrier receptors (BBB-R) and methods of using the same.

16 Claims, 20 Drawing Sheets
Specification includes a Sequence Listing.

(56) References Cited

U.S. PATENT DOCUMENTS

| | | |
|---|---|---|
| 5,798,097 A | 8/1998 | McKenzie et al. |
| 5,817,789 A | 10/1998 | Heartlein et al. |
| 5,833,988 A | 11/1998 | Friden |
| 5,912,336 A | 6/1999 | Sparling et al. |
| 5,922,323 A | 7/1999 | Loosmore et al. |
| 5,922,562 A | 7/1999 | Loosmore et al. |
| 5,922,841 A | 7/1999 | Loosmore et al. |
| 5,977,307 A | 11/1999 | Friden et al. |
| 6,008,326 A | 12/1999 | Loosmore et al. |
| 6,015,555 A | 1/2000 | Friden |
| 6,015,688 A | 1/2000 | Loosmore et al. |
| 6,027,921 A | 2/2000 | Heartlein et al. |
| 6,028,049 A | 2/2000 | Jacobs et al. |
| 6,060,058 A | 5/2000 | Schryvers |
| 6,077,834 A | 6/2000 | Cheng |
| 6,090,576 A | 7/2000 | Myers et al. |
| 6,099,842 A | 8/2000 | Pastan et al. |
| 6,190,668 B1 | 2/2001 | Yang et al. |
| 6,214,974 B1 | 4/2001 | Rosenblum et al. |
| 6,262,016 B1 | 7/2001 | Loosmore et al. |
| 6,287,792 B1 | 9/2001 | Pardridge et al. |
| 6,290,970 B1 | 9/2001 | Yang et al. |
| 6,326,350 B1 | 12/2001 | Jacobs et al. |
| 6,329,508 B1 | 12/2001 | Friden |
| 6,358,727 B1 | 3/2002 | Loosmore et al. |
| 6,361,779 B1 | 3/2002 | Loosmore et al. |
| 6,372,250 B1 | 4/2002 | Pardridge |
| 6,437,096 B1 | 8/2002 | Myers et al. |
| 6,440,701 B1 | 8/2002 | Myers et al. |
| 6,497,881 B1 | 12/2002 | Meruelo et al. |
| 6,511,967 B1 | 1/2003 | Weissleder et al. |
| 6,660,264 B1 | 12/2003 | Pasechnik et al. |
| 6,743,893 B2 | 6/2004 | Engler et al. |
| 6,821,504 B2 | 11/2004 | Wisniewski et al. |
| 6,858,578 B2 | 2/2005 | Heartlein et al. |
| 6,891,028 B1 | 5/2005 | Kawabata et al. |
| 7,083,934 B2 | 8/2006 | Kawabata et al. |
| 7,090,864 B2 | 8/2006 | Pardridge |
| 7,118,749 B2 | 10/2006 | Loosmore et al. |
| 7,211,251 B2 | 5/2007 | Kawabata et al. |
| 7,241,449 B1 | 7/2007 | Myers et al. |
| 7,479,276 B1 | 1/2009 | Xu et al. |
| 7,572,895 B2 | 8/2009 | Mather et al. |
| 7,582,730 B2 | 9/2009 | Sparling et al. |
| 7,666,991 B2 | 2/2010 | Mrsny |
| 7,713,737 B2 | 5/2010 | Mrsny |
| 7,736,647 B2 | 6/2010 | Boumsell et al. |
| 7,741,446 B2 | 6/2010 | Pardridge et al. |
| 7,780,882 B2 | 8/2010 | Chang et al. |
| 7,811,572 B2 | 10/2010 | Dai et al. |
| 7,858,757 B2 | 12/2010 | Hollmann et al. |
| 7,973,019 B1 | 7/2011 | Chatterton et al. |
| 7,976,841 B2 | 7/2011 | Monteiro et al. |
| 8,053,569 B2 | 11/2011 | Pardridge et al. |
| 8,106,161 B2 | 1/2012 | Ledbetter et al. |
| 8,124,095 B2 | 2/2012 | Pardridge et al. |
| 8,142,781 B2 | 3/2012 | Pardridge et al. |
| 2002/0102261 A1 | 8/2002 | Raso |
| 2004/0102369 A1 | 5/2004 | Wu et al. |
| 2004/0146516 A1 | 7/2004 | Roben et al. |
| 2005/0042298 A1 | 2/2005 | Pardridge et al. |
| 2008/0019984 A1 | 1/2008 | Shusta et al. |
| 2008/0154022 A1 | 6/2008 | Wu et al. |
| 2008/0213179 A1 | 9/2008 | Gaillard et al. |
| 2010/0077498 A1 | 3/2010 | Pardridge et al. |
| 2010/0098693 A1 | 4/2010 | Pardridge et al. |
| 2011/0044980 A1 | 2/2011 | Ghayur et al. |
| 2012/0237526 A1 | 9/2012 | De Strooper et al. |

FOREIGN PATENT DOCUMENTS

| | | | |
|---|---|---|---|
| EP | 0592564 | B1 | 9/1996 |
| EP | 1975178 | A1 | 10/2008 |
| JP | 6210017 | | 4/1987 |
| JP | 4187096 | A | 11/1990 |
| JP | 92/17210 | A1 | 10/1992 |
| JP | 10245400 | A | 9/1998 |
| JP | 2002095476 | A | 4/2002 |
| JP | 2005321411 | A | 11/2005 |
| JP | 3973169 | B2 | 6/2007 |
| WO | 81/02930 | A1 | 10/1981 |
| WO | 88/00834 | A1 | 2/1988 |
| WO | 89/10134 | A1 | 11/1989 |
| WO | 90/12591 | A1 | 11/1990 |
| WO | 91/03259 | A1 | 3/1991 |
| WO | 91/14452 | A1 | 10/1991 |
| WO | 92/03467 | A1 | 3/1992 |
| WO | 92/09613 | A1 | 6/1992 |
| WO | 92/22332 | A2 | 12/1992 |
| WO | 93/02108 | A1 | 2/1993 |
| WO | 93/10819 | A1 | 6/1993 |
| WO | 94/02178 | A1 | 2/1994 |
| WO | 95/02421 | A1 | 1/1995 |
| WO | 95/13370 | A1 | 5/1995 |
| WO | 95/15982 | A2 | 6/1995 |
| WO | 95/15982 | A3 | 6/1995 |
| WO | 95/21195 | A1 | 8/1995 |
| WO | 96/39510 | A1 | 12/1996 |
| WO | 97/13785 | A1 | 4/1997 |
| WO | 97/19957 | A1 | 6/1997 |
| WO | 97/28817 | A1 | 8/1997 |
| WO | 97/32980 | A1 | 9/1997 |
| WO | 98/22092 | A1 | 5/1998 |
| WO | 99/42127 | A2 | 8/1999 |
| WO | 99/42127 | A3 | 8/1999 |
| WO | 00/27874 | A2 | 5/2000 |
| WO | 00/27874 | A3 | 5/2000 |
| WO | 00/29574 | A2 | 5/2000 |
| WO | 00/29574 | A3 | 5/2000 |
| WO | 00/29600 | A1 | 5/2000 |
| WO | 00/50008 | A2 | 8/2000 |
| WO | 00/50008 | A3 | 8/2000 |
| WO | 00/61190 | A2 | 10/2000 |
| WO | 00/61190 | A3 | 10/2000 |
| WO | 01/07084 | A1 | 2/2001 |
| WO | 01/44300 | A2 | 6/2001 |
| WO | 01/44300 | A3 | 6/2001 |
| WO | 01/74399 | A1 | 10/2001 |
| WO | 01/82900 | A1 | 11/2001 |
| WO | 01/82972 | A2 | 11/2001 |
| WO | 01/82972 | A3 | 11/2001 |
| WO | 02/00914 | A2 | 1/2002 |
| WO | 02/00914 | A3 | 1/2002 |
| WO | 02/07783 | A2 | 1/2002 |
| WO | 02/07783 | A3 | 1/2002 |
| WO | 02/21141 | A2 | 3/2002 |
| WO | 02/21141 | A3 | 3/2002 |
| WO | 02/44329 | A2 | 6/2002 |
| WO | 02/44329 | A9 | 6/2002 |
| WO | 02/055736 | A2 | 7/2002 |
| WO | 02/055736 | A3 | 7/2002 |
| WO | 02/094191 | A2 | 11/2002 |
| WO | 02/094191 | A3 | 11/2002 |
| WO | 03/020746 | A1 | 3/2003 |
| WO | 03/075747 | A2 | 9/2003 |
| WO | 03/075747 | A3 | 9/2003 |
| WO | 03/084470 | A2 | 10/2003 |
| WO | 03/084470 | A3 | 10/2003 |
| WO | 2003/083069 | A2 | 10/2003 |
| WO | 2003/083069 | A3 | 10/2003 |
| WO | 2004/019872 | A2 | 3/2004 |
| WO | 2004/019872 | A3 | 3/2004 |
| WO | 2004/020404 | A2 | 3/2004 |
| WO | 2004/020404 | A3 | 3/2004 |
| WO | 2004/020405 | A2 | 3/2004 |
| WO | 2004/020405 | A3 | 3/2004 |
| WO | 2004/020454 | A2 | 3/2004 |
| WO | 2004/020454 | A3 | 3/2004 |
| WO | 2004/020588 | A2 | 3/2004 |
| WO | 2004/020588 | A3 | 3/2004 |
| WO | 2004/041867 | A2 | 5/2004 |
| WO | 2004/041867 | A3 | 5/2004 |
| WO | 2004/062602 | A2 | 7/2004 |
| WO | 2004/062602 | A3 | 7/2004 |

(56) References Cited

FOREIGN PATENT DOCUMENTS

| | | |
|---|---|---|
| WO | 2004/069870 A2 | 8/2004 |
| WO | 2004/078777 A2 | 9/2004 |
| WO | 2004/078777 A3 | 9/2004 |
| WO | 2004/108071 A2 | 12/2004 |
| WO | 2004/108071 A3 | 12/2004 |
| WO | 2005/014822 A2 | 2/2005 |
| WO | 2005/014822 A3 | 2/2005 |
| WO | 2005/017148 A1 | 2/2005 |
| WO | 2005/021579 A2 | 3/2005 |
| WO | 2005/021579 A3 | 3/2005 |
| WO | 2005/025511 A2 | 3/2005 |
| WO | 2005/037989 A2 | 4/2005 |
| WO | 2005/037989 A3 | 4/2005 |
| WO | 2005/089148 A2 | 9/2005 |
| WO | 2005/089148 A3 | 9/2005 |
| WO | 2005/094364 A2 | 10/2005 |
| WO | 2005/094364 A3 | 10/2005 |
| WO | 2005/100401 A2 | 10/2005 |
| WO | 2005/100401 A3 | 10/2005 |
| WO | 2005/111082 A1 | 11/2005 |
| WO | 2005/117999 A2 | 12/2005 |
| WO | 2005/117999 A3 | 12/2005 |
| WO | 2005/121179 A2 | 12/2005 |
| WO | 2005/121179 A3 | 12/2005 |
| WO | 610046 B1 | 12/2005 |
| WO | 2006/004910 A2 | 1/2006 |
| WO | 2006/004910 A3 | 1/2006 |
| WO | 2006/044205 A2 | 4/2006 |
| WO | 2006/044205 A3 | 4/2006 |
| WO | 2006/088491 A2 | 8/2006 |
| WO | 2006/088491 A3 | 8/2006 |
| WO | 2006/088503 A1 | 8/2006 |
| WO | 2006/096515 A2 | 9/2006 |
| WO | 2006/096515 A3 | 9/2006 |
| WO | 2006/099516 A2 | 9/2006 |
| WO | 2006/099516 A3 | 9/2006 |
| WO | 2006/126208 A2 | 11/2006 |
| WO | 2006/126208 A3 | 11/2006 |
| WO | 2006/133566 A1 | 12/2006 |
| WO | 2007/000671 A2 | 1/2007 |
| WO | 2007/000671 A3 | 1/2007 |
| WO | 2007/027559 A2 | 3/2007 |
| WO | 2007/027559 A3 | 3/2007 |
| WO | 2007/044323 A2 | 4/2007 |
| WO | 2007/044323 A3 | 4/2007 |
| WO | 2007/047504 A2 | 4/2007 |
| WO | 2007/047504 A3 | 4/2007 |
| WO | 2007/067596 A2 | 6/2007 |
| WO | 2007/067596 A3 | 6/2007 |
| WO | 2007/067597 A2 | 6/2007 |
| WO | 2007/067597 A3 | 6/2007 |
| WO | 2007/068412 A2 | 6/2007 |
| WO | 2007/068412 A3 | 6/2007 |
| WO | 2007/103288 A2 | 9/2007 |
| WO | 2007/103288 A3 | 9/2007 |
| WO | 2007/112451 A2 | 10/2007 |
| WO | 2007/112451 A3 | 10/2007 |
| WO | 2007/113172 A2 | 10/2007 |
| WO | 2008/011348 A2 | 1/2008 |
| WO | 2008/011348 A3 | 1/2008 |
| WO | 2008/013709 A2 | 1/2008 |
| WO | 2008/021234 A2 | 2/2008 |
| WO | 2008/021234 A3 | 2/2008 |
| WO | 2008/021412 A2 | 2/2008 |
| WO | 2008/021412 A3 | 2/2008 |
| WO | 2008/022349 A2 | 2/2008 |
| WO | 2008/022349 A3 | 2/2008 |
| WO | 2008/033395 A2 | 3/2008 |
| WO | 2008/033395 A3 | 3/2008 |
| WO | 2008/033924 A2 | 3/2008 |
| WO | 2008/033924 A3 | 3/2008 |
| WO | 2008/050133 A2 | 5/2008 |
| WO | 2008/050133 A3 | 5/2008 |
| WO | 2008/054544 A2 | 5/2008 |
| WO | 2008/054544 A3 | 5/2008 |
| WO | 2008/106524 A1 | 9/2008 |
| WO | 2008/118013 A2 | 10/2008 |
| WO | 2008/118013 A3 | 10/2008 |
| WO | 2008/147526 A1 | 12/2008 |
| WO | 2008/152140 A2 | 12/2008 |
| WO | 2008/152140 A3 | 12/2008 |
| WO | 2008/156621 A1 | 12/2008 |
| WO | 2008/156622 A1 | 12/2008 |
| WO | 2008/156622 A8 | 12/2008 |
| WO | 2009/058383 A2 | 5/2009 |
| WO | 2009/058383 A3 | 5/2009 |
| WO | 2009/081154 A1 | 7/2009 |
| WO | 2009/094561 A1 | 7/2009 |
| WO | 2009/121804 A1 | 10/2009 |
| WO | 2009/149281 A1 | 12/2009 |
| WO | 2009/155609 A1 | 12/2009 |
| WO | 2010/037135 A2 | 4/2010 |
| WO | 2010/037135 A3 | 4/2010 |
| WO | 2010/081173 A2 | 7/2010 |
| WO | 2010/081173 A3 | 7/2010 |
| WO | WO-2010088522 A2 * | 8/2010 ......... C07K 16/2809 |
| WO | 2010/108048 A2 | 9/2010 |
| WO | 2010/108048 A3 | 9/2010 |
| WO | 2010/0120262 A1 | 10/2010 |
| WO | 2011/009624 A1 | 1/2011 |
| WO | 2011/057216 A1 | 5/2011 |
| WO | 2011/073943 A1 | 6/2011 |
| WO | 2011/088409 A1 | 7/2011 |
| WO | 2011/090762 A1 | 7/2011 |
| WO | 2011/130164 A2 | 10/2011 |
| WO | 2011/130164 A3 | 10/2011 |
| WO | 2011/138557 A2 | 11/2011 |
| WO | 2011/138557 A3 | 11/2011 |
| WO | 2012/075037 A1 | 6/2012 |

OTHER PUBLICATIONS

Ng PP et al. An anti-transferrin receptor-avidin fusion protein exhibits both strong proapoptotic activity and the ability to deliver various molecules into cancer cells. Proc. Natl. Acad. Sci. USA, 99(16), 10706-10711. (Year: 2002).*

Moos et al., "Restricted transport of anti-transferrin receptor antibody (OX26) through the blood-brain barrier in the rat" Journal of Neurochemistry 79:119-129 (2001).

Boado et al., "Drug targeting of erythropoietin across the primate blood-brain barrier with an IgG molecular Trojan horse" J Pharm Exp Ther, Am Soc Pharm Exp Ther 333(3):961-969 (Jun. 1, 2010).

Boado et al., "Engineering and expression of a chimeric transferrin receptor monoclonal antibody for blood-brain barrier delivery in the mouse" Biotechnol Bioeng 102(4):1251-1258 (Mar. 1, 2009).

Schneider et al., "Primary structure of human transferrin receptor deduced from the mRNA sequence" Nature 311:675-678 (Oct. 18, 1984).

Pardridge, "Drug and gene targeting to the brain with molecular Trojan horses" Nature Reviews 1(2):131-139 (Feb. 2002).

Trowbridge and Omary, "Human cell surface glycoprotein related to cell proliferation is the receptor for transferrin" Proc Natl Acad Sci USA 78(5):3039-3043 (May 1981).

Gosk et al., "Targeting Anti-Transferrin Receptor Antibody (OX26) and OX26-Conjugated Liposomes to Brain Capillary Endothelial Cells Using In Situ Perfusion" Journal of Cerebral Blood Flow & Metabolism 24:1193-1204 (Nov. 2004).

Omary and Trowbridge, "Biosynthesis of the transferrin receptor in cultured cells" J Biol Chem 256(24):12888-12892 (Dec. 25, 1981).

Paul, Steven, "Therapeutic antibodies for brain disorders" Science Translational Med 3(84):84ps20 (May 25, 2011).

"KD Value A quantitative measurement of antibody affinity." Abcam, pp. 1-5 (downloaded Jun. 2014).

Cole and Vassar, "The Alzheimer's disease β-secretase enzyme, BACE1" Molec Neurodegeneration 2(1):22 (Nov. 15, 2007).

Shin et al., "Transferrin-antibody fusion proteins are effective in brain targeting" Proc Natl Acad Sci USA 92:2820-2824 (Mar. 1995).

Skarlatos et al., "Transport of $^{125}$Itransferrin through the rat blood-brain barrier" Brain Res 683:164-171 (1995).

(56) References Cited

OTHER PUBLICATIONS

Pardridge, "Biologic TNFα-inhibitors that cross the human blood-brain barrier" Bioengineered Bugs 1(4):231-234 (Jul. 2010).
Vassar et al., "β-Secretase cleavage of Alzheimer's amyloid precursor transmembrane aspartic protease BACE" Science 286:735-741 (Oct. 22, 1999).
Wang et al., "Mining a yeast library for brain endothelial cell-binding antibodies" Nat. Methods 4(2):143-145 (2007).
Trowbridge and Lopez, "Monoclonal antibody to transferrin receptor blocks transferrin binding and inhibits human tumor cell growth in vitro" Proc Natl Acad Sci USA 79:1175-1179 (Feb. 1982).
Sutherland et al., "Ubiquitous cell-surface glycoprotein on tumor cells is proliferation-associated receptor for transferrin" Proc Natl Acad Sci USA 78(7):4515-4519 (Jul. 1981).
Boado et al., "IgG-single chain Fv fusion protein therapeutic for Alzheimer's disease: Expression in CHO cells and pharmacokinetics and brain delivery in the rhesus monkey" Biotechnol Bioeng 105(3):627-635 (Feb. 15, 2010).
Yu et al., "Boosting brain uptake of a therapeutic antibody by reducing its affinity for a transcytosis target" Science Translational Med 3(84):84ra44 (May 25, 2011).
Dennis et al., "Transferrin Antibodies into the Brain" Neuropsychopharmacology 37:302-3030 (2012).
Atwal et al., "A therapeutic antibody targeting BACE1 inhibits amyloid-β production in vivo" Science Translational Med 3(84):84ra43 (May 25, 2011).
Pardridge et al., "β-Endorphin chimeric peptides: Transport through the blood-brain barrier in vivo and cleavage of disulfide linkage by brain" Endocrinology 126(2):977-984 (1990).
Jefferies et al., "Transferrin receptor on endothelium of brain capillaries" Nature 312:162-163 (Nov. 8, 1984).
Faulk et al., "Transferrin and transferrin receptors in carcinoma of the breast" Lancet 2(8191):390-392 (Aug. 23, 1980).
Ridgway et al., "'Knobs-into-holes' engineering of antibody $C_H3$ domains for heavy chain heterodimerization" Protein Eng 9(7):617-621 (1996).
Kornacker et al., "An inhibitor binding pocket distinct from the catalytic active site on human β-APP cleaving enzyme" Biochem 44:11567-11573 (2005).
Zhou et al., "Receptor-mediated abeta amyloid antibody targeting to Alzheimer's disease mouse brain" Molec Pharmaceutics 8(1):280-285 (Feb. 7, 2011).
Boado et al., "Pharmacokinetics and brain uptake of a genetically engineered bifunctional fusion antibody targeting the mouse transferrin receptor" Molec Pharmaceutics (e-published Nov. 18, 2009), 7(1):237-244 (Feb. 1, 2010).
Cheng et al., "Relationship Between the Inhibition Constant ($K_1$) and the Concentration of Inhibitor Which Causes 50 Percent Inhibition ($I_{50}$) of an Enzymatic Reaction," Biochemical Pharmacology 22:3099-3108 (1973).
Adams et al. "High affinity restricts the localization and tumor penetration of single-chain Fv antibody molecules," Cancer Res. 61:4750-4755 (2001).
Aktas et al., "Development and Brain Delivery of Chitosan-PEG Nanoparticles Functionalized with the Monoclonal Antibody OX26" Bioconjugate Chem. 16:1503-1511
Allen, "Ligand-Targeted Therapeutics in Anticancer Therapy" Nature 2:750-763 (Oct. 2002).
Azimzadeh et al., "Antibody Affinity Measurements" J. of Molecular Recognition 3(3) (1990).
Banks, "Delivery of Peptides to the Brain: Emphasis on Therapeutic Development" PeptideScience 90(5):589-594 (Mar. 11, 2008).
Bickel et al., "Pharmacologic effects in vivo in brain by vector-mediated peptide drug delivery" Proc. Natl. Acad. Sci. USA 90:2618-2622 (Apr. 1993).
Bigott-Hennkens et al., "In vitro receptor binding assays: general methods and considerations" Q J Nucl. Med. Mol. Imaging 52(3):245-253 (2008).
Carter, "Potent antibody therapeutics by design" Nature Reviews 6:343-357 (May 2006).
Chowdhury et al., "Tailor-made antibody therapeutics" Methods 36:11-24 (2005).
Couch et al., "Addressing Safety Liabilities of TfR Bispecific Antibodies that Cross the Blood-Brain Barrier" Science Translational Medicine 5(183):183ra57 (12 pages) (May 1, 2013).
Friguet et al., "Measurements of the True Affinity Constant in Solution of Antigen-Antibody Complexes by Enzyme-Linked Immunosorbent Assay" Journal of Immunological Methods 77:305-319 (1985).
Fujimori et al., "Modeling Analysis of the Global and Microscopic Distribution of Immunoglobulin G, F(ab')2, and Fab in Tumors" Cancer Research 49:5656-5663 (Oct. 15, 1989).
Guerreiro et al., "The Genetic Architecture of Alzheimer's Disease: Beyond APP, PSENs AND APOE" Neurobiol Aging 33(3):437-456 (Mar. 2012).
Jefferies et al., "Analysis of lymphopoietic stem cells with a monoclonal antibody to the rat transferrin receptor" Immunology 54:333-341 ( 1985).
Juweid et al., "Micropharmacology of Monoclonal Antibodies in Solid Tumors: Direct Experimental Evidence for a Binding Site Barrier" Cancer Research 52:5144-5153 (Oct. 1, 1992).
Kenanova et al., "Tailoring antibodies for radionuclide delivery" Expert Opin. Drug Delivery 3(1):53-70 (2006).
Kievit et al., "Comparison of the monoclonal antibodies 17-1A and 323/A3: the influence of the affinity on tumor uptake and efficacy of radioimmunotherapy in human ovarian cancer xenografts" Brit. J. Cancer 73:457-464 (1996).
Lanctot et al., "Therapy for Alzheimer's disease: how effective are current treatments?" Therapeutic Advances in Neurological Disorders 2(3):163-180 (2009).
Lee et al., "Targeting Rat Anti-Mouse Transferrin Receptor Monoclonal Antibodies through Blood-Brain Barrier in Mouse" The Journal of Pharmacology and Experimental Therapeutics 292(3):1048-1052 (2000).
Li et al., "Genetically engineering brain drug delivery vectors: cloning, expression and in vivo application of an anti-transferrin receptor single chain antibody-streptavidin fusion gene and protein" Protein Engineering 12(9):787-796 (1999)
Neubig et al., "International Union of Pharmacology Committee on Receptor Nomenclature and Drug Classification. XXXVIII. Update on Terms and Symbols in Quantative Pharmacology" Pharmacology Reviews 55(4):597-606 (2003).
Newton et al., "A Novel Method for Determination of the Affinity of Protein: Protein Interactions in Homogeneous Assays" Journal of Biomolecular Screening 13(7):674-682 (2008).
Nielsen et al., "Targeting of Bivalent Anti-ErbB2 Diabody Antibody Fragments to Tumor Cells is Independent of the Intrinsic Antibody Affinity" Cancer Research 60:6434-6440 (Nov. 15, 2000).
Notice of Opposition filed in related European Patent No. EP2646470 by Pfizer, Inc., dated Dec. 1, 2017, 13 pages.
Notice of Opposition filed in related European Patent No. EP2646470 by Lavoix, dated Dec. 1, 2017, 38 pages.
Notice of Opposition filed in related European Patent No. 2646470 by EIP, dated Dec. 1, 2017, 16 pages.
Noyce et al. Neurodegenerative Diseases, advances in Neurobiology "Chapter 3: Parkinson's Disease: Basic Pathomechanisms and a Clinical Overview" Springer International Publishing AG, vol. 15:55-92 (2017).
Pardridge et al., "Selective Transport of an Anti-transferrin Receptor Antibody through the Blood-Brain Barrier in Vivo" The Journal of Pharmacology and Experimental Therapeutics 259(1):66-70 (Jun. 1991).
Patel et al., "Getting into the Brain: Approaches to Enhance Brain Drug Delivery" CNS Drug 23(1):35-58 (2009).
Pepinsky et al., "Exposure Levels of Anti-LINGO-1 Li81 Antibody in the Central Nervous System and Dose-Efficacy Relationships in Rat Spinal Cord Remyelination Models after Systemic Administration" The Journal of Pharmacology and Experimental Therapeutics 339(2):519-529 (2011).
Qian et al., "Targeted Drug Delivery via the Transferrin Receptor-Mediated Endocytosis Pathway" Pharmacology Reviews 54(4):561-587 (2002).

(56) References Cited

OTHER PUBLICATIONS

Rippley et al., "Effects of Cellular Pharmacology on Drug Distribution in Tissues" Biophysical Journal 69:825-839 (Sep. 1995).
Rudnick et al, "Affinity and avidity in antibody-based tumor targeting," Cancer Biother. Radiopharm. 24(2):155-161 (2009).
Sathornsumetee et al. Handbook of Clinical Neurology, Chapter 18, "Molecular targeted therapy in neuro-oncology," W. Grisold and R. Soffietti, 3rd Edition, Elsevier B.V., vol. 104:255-278.
Siegal, Blood-Brain Barrier: Drug Delivery and Brain Pathology, Chapter 22, "Strategies for Increasing Drug Delivery to the Brain: Lessons derived from treatment of brain tumors" Boston, MA, Spring (2001).
Ulbrich et al., "Transferrin- and transferrin-receptor-antibody-modified nanoparticles enable drug delivery across the blood-brain barrier (BBB)" European Journal of Pharmaceutics and Biopharmaceutics 71:251-256 (2009).
Weiner et al., "Tunable antibodies" Nature Biotechnology 23(5):556-557 (May 2005).
Wilkinson et al. Methods in Molecular Biology Chapter 2 "Quantitative Analysis of Protein-Protein Interactions" H. Fu, Totowa, NJ: Humana Press Inc., vol. 261:15-31 (2004).
Xia et al., "Intravenous glial-derived neurotrophic factor gene therapy of experimental Parkinson's disease with Trojan horse liposomes and a tyrosine hydroxylase promoter" The Journal of Gene Medicine 10:306-315 (2008).
Yu et al., "Therapeutic bispecific antibodies cross the blood-brain barrier in nonhuman primates" Science Translational Medicine 6(261):1-11 (Nov. 5, 2014).
Zhang et al., "Absence of Toxicity of Chronic Weekly Intravenous Gene Therapy with Pegylated Immunoliposomes" Pharmaceutical Research 20(11):1779-1785 (Nov. 2003).
Zhang et al., "Conjugation of brain-derived neurotrophic factor to a blood-brain barrier drug targeting system enables neuroprotection in regional brain ischemia following intravenous injection of the neurotrophin" Brain Research 889:49-56 (2001).
Zhang et al., "Intravenous Nonviral Gene Therapy Causes Normalization of Striatal Tyrosine Hydroxylase and Reversal of Motor Impairment in Experimental Parkinsonism" Human Gene Therapy 14:1-12 (Jan. 2003).
Zhang et al., "Near Complete Rescue of Experimental Parkinson's Disease with Intravenous, Non-viral GDNF Gene Therapy" Pharmaceutical Research 26(5):1059-1063 (May 2009).
Zhang et al., "Neuroprotection in Transient Focal Brain Ischemia After Delayed Intravenous Administration of Brain-Derived Neurotrophic Factor Conjugated to a Blood-Brain Barrier Drug Targeting System" Stroke 32:1378-1384 (Jun. 2001).
Gabathuler, "Development of new peptide vectors for the transport of therapeutic across the blood-brain barrier", Therapeutic Delivery, (2010), vol. 1(4), pp. 571-586.
Hanzatian et al., "Brain uptake of multivalent and multi-specific DVD-Ig proteins after systemic administration", mAbs, vol. 10(5), (2018_, pp. 765-777.
Johnsen et al., "Antibody affinity and valency impact brain update of transferrin receptor-targeted gold nanoparticles", Theronostics, (2018), vol. 8, Issue 12, pp. 3416-3436.
Krohn et al., "Interpreting enzyme and receptor kinetics: keeping it simple, but not too simple", Nuclear Medicine and Biology, 30 (2003), pp. 819-826.
EIP Limited, Notice regarding Opposition against European Patent Application No. 11794336.5; dated Apr. 11, 2019 (8 pages).
Lavoix, Notice regarding Opposition to European Patent No. 2646470, dated Apr. 9, 2019. (23 pages).
European Patent Office, Opposition Summary of Facts and Submissions regarding European Patent Application No. 11794336.5, dated Nov. 19, 2018 (17 pages).
Mewburn Ellis LLP, Opposition response to summons against European Patent Application No. 11794336.5; dated Apr. 11, 2019 (3 pages).
Poul et al., "Selection of Tumor-Specific Internalizing Human Antibodies from Phage Libraries", J. Mol. Biol., vol. 301, (2000), pp. 1149-1161.
Thom et al., "Enhanced Delivery of Galanin Conjugates to the Brain through Bioengineering of the Anti-Transferrin Receptor Antibody OX26", Mol Pharm., (Apr. 2, 2018);15(4): pp. 1420-1431.

* cited by examiner

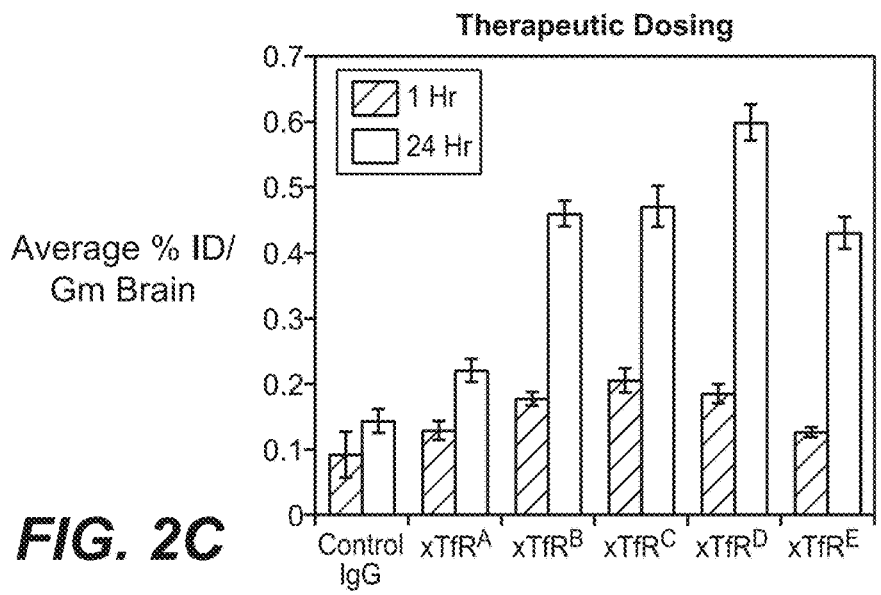
FIG. 2C
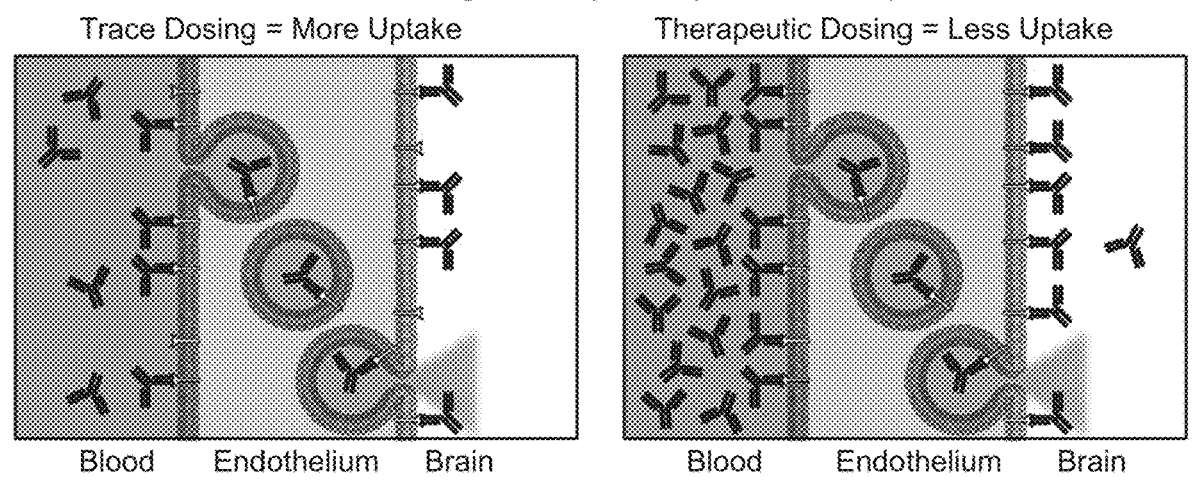
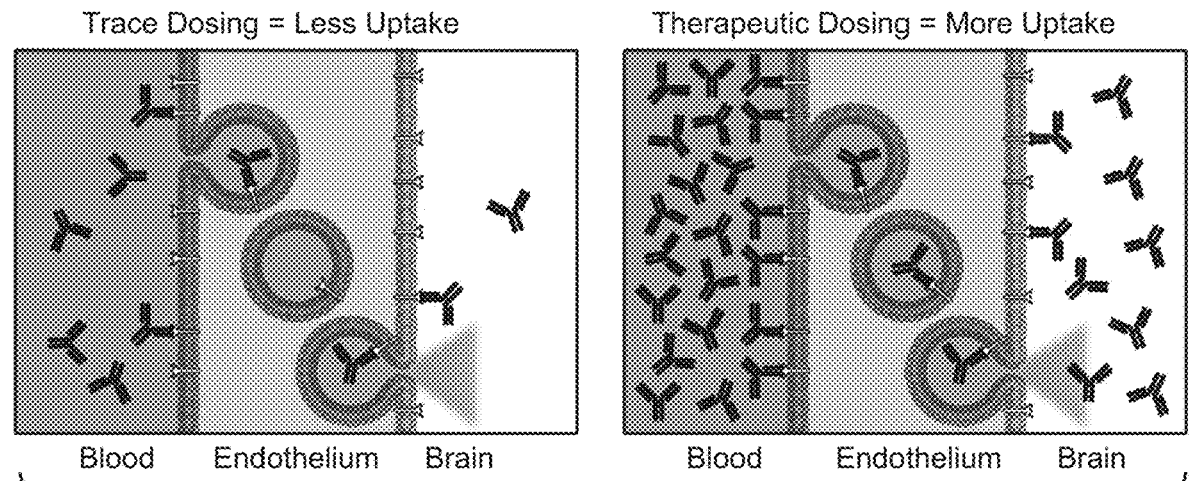
FIG. 2D

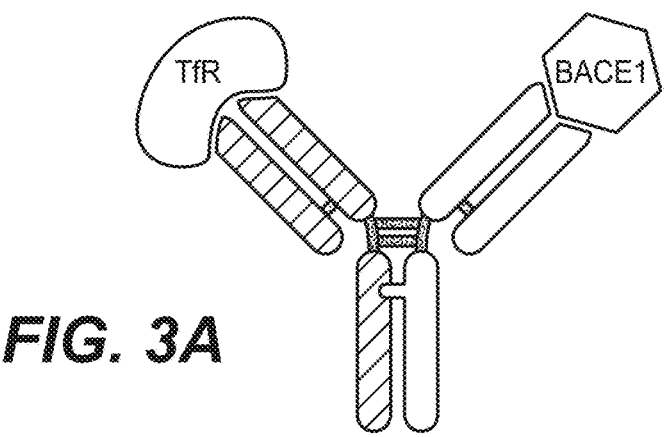
FIG. 3A
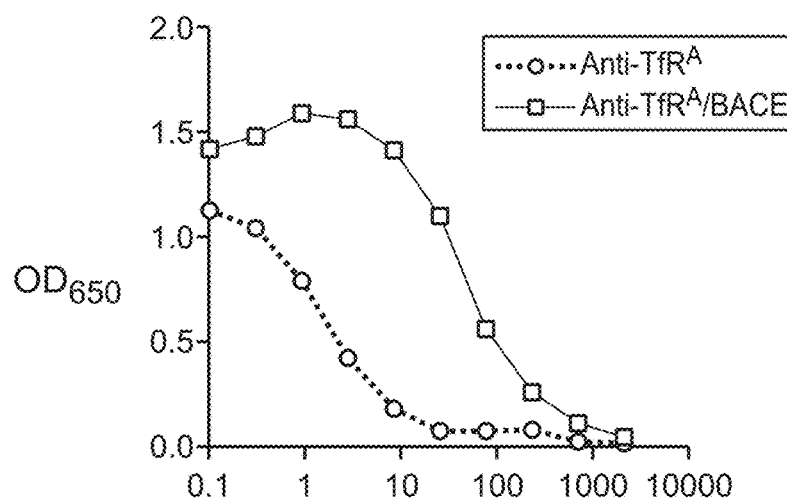
FIG. 3B Antibody Concentration (nM)
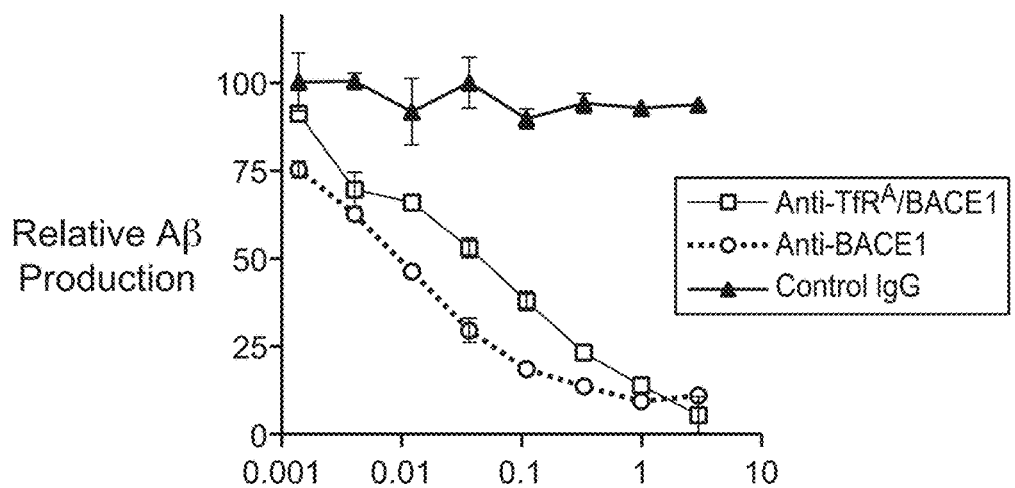
FIG. 3C Antibody Concentration (µM)

| Kabat# | 1 2 3 4 5 6 7 8 9 10 11 12 13 14 15 16 17 18 19 20 21 22 23 24 25 26 27 A B C D E F 28 29 30 31 32 33 34 35 36 37 |
|---|---|
| | Kabat - CDR L1 |
| | Chothia - CDR L1     Contact - CDR L1 |
| YW412.8    | D I Q M T Q S P S S L S A S V G D R V T I T C R A S Q        D V S T A V A W Y Q |
| YW412.8.31 | D I Q M T Q S P S S L S A S V G D R V T I T C R A S Q        D V S T A V A W Y Q |
| YW412.8.30 | D I Q M T Q S P S S L S A S A G D R V T I T C R A S Q        D V S T A W A W Y Q |
| YW412.8.2  | D I Q M T Q S P S S L S A S V G D R V T I T C R A S Q        D V V T A V L W Y Q |
| YW412.8.29 | D I Q M T Q S P S S L S A S A G D R V T I T C R A S Q        D V A N S A W Y Q |
| YW412.8.51 | D I Q M T Q S P S S L S A S V G D R V T I T C R A S Q        D V S T A V A W Y Q |

| Kabat# | 38 39 40 41 42 43 44 45 46 47 48 49 50 51 52 53 54 55 56 57 58 59 60 61 62 63 64 65 66 67 68 69 70 71 72 73 74 75 76 77 78 79 80 |
|---|---|
| | Kabat - CDR L2 |
| | Chothia - CDR L2 |
| | Contact - CDR L2 |
| YW412.8    | Q K P G K A P K L L I Y S A S F L Y S G V P S R F S G S G S G T D F T L T I S S L Q |
| YW412.8.31 | Q K P G K A P K L L I Y S A S F L Y S G V P S R F S G S G S G T D F T L T I S S L Q |
| YW412.8.30 | Q K P G K A P K L L I Y S A S F L Y S G V P S R F S G S G S G T D F T L T I S S L Q |
| YW412.8.2  | Q K P G K A P K L L I Y S A S F L Y S G V P S R F S G S G S G T D F T L T I S S L Q |
| YW412.8.29 | Q K P G K A P K L L I Y L A S F L Y S G V P S R F S G S G S G T D F T L T I S S L Q |
| YW412.8.51 | Q K P G K A P K L L I Y S A S F L Y S G V P S R F S G S G S G T D F T L T I S S L Q |

| Kabat# | 81 82 83 84 85 86 87 88 89 90 91 92 93 94 95 96 97 98 99 100 101 102 103 104 105 106 107 108 |
|---|---|
| | Kabat - CDR L3 |
| | Chothia - CDR L3 |
| | Contact - CDR L3 |
| YW412.8    | E D F A T Y Y C Q Q S Y T T P P T F G Q G T K V E I K R | SEQ ID NO: 1 |
| YW412.8.31 | E D F A T Y Y C Q Q Y P P Y L P T F G Q G T K V E I K R | SEQ ID NO: 2 |
| YW412.8.30 | E D F A T Y Y C Q Q G Y N D P P T F G Q G T K V E I K R | SEQ ID NO: 3 |
| YW412.8.2  | E D F A T Y Y C Q Q G S T D P P T F G Q G T K V E I K R | SEQ ID NO: 4 |
| YW412.8.29 | E D F A T Y Y C Q Q Q D A T P P T F G Q G T K V E I K R | SEQ ID NO: 5 |
| YW412.8.51 | E D F A T Y Y C Q Q Y A T D P P T F G Q G T K V E I K R | SEQ ID NO: 6 |

Heavy chain sequence alignment (Kabat numbering):

Positions 1-40:

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|---|---|---|---|---|---|---|---|---|---|---|---|---|---|---|---|---|---|---|
| YW412.8    | E | V | Q | L | V | E | S | G | G | G | L | V | Q | P | G | G | S | L | R | L | S | C | A | A | S | G | F | T | F | S | G | Y | A | I | H | W | V | R | Q | A |
| YW412.8.31 | E | V | Q | L | V | E | S | G | G | G | L | V | Q | P | G | G | S | L | R | L | S | C | A | A | S | G | F | T | F | T | G | Y | A | I | H | W | V | R | Q | A |
| YW412.8.30 | E | V | Q | L | V | E | S | G | G | G | L | V | Q | P | G | G | S | L | R | L | S | C | A | A | S | G | F | T | F | L | G | Y | G | I | H | W | V | R | Q | A |
| YW412.8.2  | E | V | Q | L | V | E | S | G | G | G | L | V | Q | P | G | G | S | L | R | L | S | C | A | A | S | G | F | T | F | S | G | Y | A | I | H | W | V | R | Q | A |
| YW412.8.29 | E | V | Q | L | V | E | S | G | G | G | L | V | Q | P | G | G | S | L | R | L | S | C | A | A | S | G | F | T | F | S | G | Y | A | I | H | W | V | R | Q | A |
| YW412.8.51 | E | V | Q | L | V | E | S | G | G | G | L | V | Q | P | G | G | S | L | R | L | S | C | A | A | S | G | F | T | F | S | G | Y | A | I | H | W | V | R | Q | A |

CDR annotations: Chothia - CDR H1 (26-32), Kabat - CDR H1 (31-35), Contact - CDR H1 (30-35)

Positions 41-78:

| Kabat# | 41 | 42 | 43 | 44 | 45 | 46 | 47 | 48 | 49 | 50 | 51 | 52 | 52A | 52B | 52C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|---|---|---|---|---|---|---|---|---|---|---|---|---|---|---|
| YW412.8    | P | G | K | G | L | E | W | V | G | W | I | S | P | | | A | G | G | S | T | D | Y | A | D | S | V | K | G | R | F | T | I | S | A | D | T | S | K | N | T | A |
| YW412.8.31 | P | G | K | G | L | E | W | V | G | W | I | S | P | | | A | G | G | S | T | D | Y | A | D | S | V | K | G | R | F | T | I | S | A | D | T | S | K | N | T | A |
| YW412.8.30 | P | G | K | G | L | E | W | V | G | W | I | S | P | | | A | G | G | S | T | D | Y | A | D | S | V | K | G | R | F | T | I | S | A | D | T | S | K | N | T | A |
| YW412.8.2  | P | G | K | G | L | E | W | V | G | W | I | S | P | | | A | G | G | S | T | D | Y | A | D | S | V | K | G | R | F | T | I | S | A | D | T | S | K | N | T | A |
| YW412.8.29 | P | G | K | G | L | E | W | V | G | W | I | S | P | | | A | G | G | S | T | D | Y | A | D | S | V | K | G | R | F | T | I | S | A | D | T | S | K | N | T | A |
| YW412.8.51 | P | G | K | G | L | E | W | V | G | W | I | S | P | | | A | G | G | S | T | D | Y | A | D | S | V | K | G | R | F | T | I | S | A | D | T | S | K | N | T | A |

CDR annotations: Contact - CDR H2 (47-58), Chothia - CDR H2 (52-56), Kabat - CDR H2 (50-65)

Positions 79-113 (with SEQ ID NO):

| Kabat# | 79 | 80 | 81 | 82 | 82A | 82B | 82C | 83 | 84 | 85 | 86 | 87 | 88 | 89 | 90 | 91 | 92 | 93 | 94 | 95 | 96 | 97 | 98 | 99 | 100 | 100A | 100B | 100C | 100D | 100E | 100F | 100G | 101 | 102 | 103 | 104 | 105 | 106 | 107 | 108 | 109 | 110 | 111 | 112 | 113 | SEQ ID NO: |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| YW412.8    | Y | L | Q | M | N | S | L | R | A | E | D | T | A | V | Y | Y | C | A | R | G | P | F | S | P | W | | | | | | | | M | D | Y | W | G | Q | G | T | L | V | T | V | S | S | 7 |
| YW412.8.31 | Y | L | Q | M | N | S | L | R | A | E | D | T | A | V | Y | Y | C | A | R | G | P | F | S | P | W | | | | | | | | M | D | Y | W | G | Q | G | T | L | V | T | V | S | S | 8 |
| YW412.8.30 | Y | L | Q | M | N | S | L | R | A | E | D | T | A | V | Y | Y | C | A | R | G | P | F | S | P | W | | | | | | | | M | D | Y | W | G | Q | G | T | L | V | T | V | S | S | 7 |
| YW412.8.2  | Y | L | Q | M | N | S | L | R | A | E | D | T | A | V | Y | Y | C | A | R | G | P | F | S | P | W | | | | | | | | M | D | Y | W | G | Q | G | T | L | V | T | V | S | S | 7 |
| YW412.8.29 | Y | L | Q | M | N | S | L | R | A | E | D | T | A | V | Y | Y | C | A | R | G | P | F | S | P | W | | | | | | | | M | D | Y | W | G | Q | G | T | L | V | T | V | S | S | 7 |
| YW412.8.51 | Y | L | Q | M | N | S | L | R | A | E | D | T | A | V | Y | Y | C | A | R | G | P | F | S | P | W | | | | | | | | M | D | Y | W | G | Q | G | T | L | V | T | V | S | S | 7 |

CDR annotations: Contact - CDR H3 (93-101), Chothia - CDR H3 (95-102), Kabat - CDR H3 (95-102)

```
Kabat#          1  2  3  4  5  6  7  8  9 10 11 12 13 14 15 16 17 18 19 20 21 22 23 24 25 26 27  A  B  C  D  E  F 28 29 30 31 32 33 34 35 36 37
                                                                                            ┌─────────────────────────────────────┐
                                                                                            │ Kabat - CDR L1                      │
                                                                                            │  ┌──────────────────────────────────┤
                                                                                            │  │ Chothia - CDR L1                 │
                                                                                            │  │              ┌───────────────────┤
                                                                                            │  │              │ Contact - CDR L1  │
Fab12           D  I  Q  M  T  Q  S  P  S  S  L  S  A  S  V  G  D  R  V  T  I  T  C  R  A  S  Q                    S  V  S  S  A  V  A  W  Y  Q
LC6 IgG         D  I  Q  M  T  Q  S  P  S  S  L  S  A  S  V  G  D  R  V  T  I  T  C  R  A  S  Q                    S  V  S  S  A  V  A  W  Y  Q
LC9 IgG         D  I  Q  M  T  Q  S  P  S  S  L  S  A  S  V  G  D  R  V  T  I  T  C  R  A  S  Q                       V  S  S  A  V  A  W  Y  Q
LC10 IgG        D  I  Q  M  T  Q  S  P  S  S  L  S  A  S  V  G  D  R  V  T  I  T  C  R  A  S  Q                    S  V  S  S  A  V  A  W  Y  Q Kabat#         38 39 40 41 42 43 44 45 46 47 48 49 50 51 52 53 54 55 56 57 58 59 60 61 62 63 64 65 66 67 68 69 70 71 72 73 74 75 76 77 78 79 80
                                           ┌──────────────────────┐
                                           │ Kabat - CDR L2       │
                                           │ Chothia - CDR L2     │
                                        ┌──┴──────────────────────┤
                                        │ Contact - CDR L2        │
Fab12           Q  K  P  G  K  A  P  K  L  L  I  Y  S  A  S  S  L  Y  S  G  V  P  S  R  F  S  G  S  G  S  G  T  D  F  T  L  T  I  S  S  L  Q  P
LC6 IgG         Q  K  P  G  K  A  P  K  L  L  I  W  A  S  S  L  Y  S  G  V  P  S  R  F  S  G  S  G  S  G  T  D  F  T  L  T  I  S  S  L  Q  P
LC9 IgG         Q  K  P  G  K  A  P  K  L  L  I  Y  A  S  S  L  Y  S  G  V  P  S  R  F  S  G  S  G  S  G  T  D  F  T  L  T  I  S  S  L  Q  P
LC10 IgG        Q  K  P  G  K  A  P  K  L  L  I  W  A  S  S  L  Y  S  G  V  P  S  R  F  S  G  S  G  S  G  T  D  F  T  L  T  I  S  S  L  Q  P Kabat#         81 82 83 84 85 86 87 88 89 90 91 92 93 94 95 96 97 98 99 100 101 102 103 104 105 106 107 108
                                          ┌──────────────────────────┐
                                          │ Kabat - CDR L3           │
                                          │ Chothia - CDR L3         │
                                          │ Contact - CDR L3         │
Fab12           E  D  F  A  T  Y  Y  C  Q  Q  Y  S  S  P  F  T  F  G  Q  G  T  K  V  E  I  K  R     SEQ ID NO: 9
LC6 IgG         E  D  F  A  T  Y  Y  C  Q  Q  Y  S  S  P  F  T  F  G  Q  G  T  K  V  E  I  K  R     SEQ ID NO: 10
LC9 IgG         E  D  F  A  T  Y  Y  C  Q  Q  Y  S  S  P  F  T  F  G  Q  G  T  K  V  E  I  K  R     SEQ ID NO: 11
LC10 IgG        E  D  F  A  T  Y  Y  C  Q  Q  Y  S  S  P  F  T  F  G  Q  G  T  K  V  E  I  K  R     SEQ ID NO: 12
```

FIG. 6A

| Kabat# | | | | | | | | | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Fab12 | | | | | | | | | | E | V | Q | L | L | E | S | G | G | G | L | V | Q | P | G | G | S | L | R | L | S | C | A | A | S | G | F | N | F | Y | Y | S | S | I | H | W | V | R | Q | A |
| LC6 IgG | | | | | | | | | | E | V | Q | L | V | E | S | G | G | G | L | V | Q | P | G | G | S | L | R | L | S | C | A | A | S | G | F | N | F | Y | Y | S | S | I | H | W | V | R | Q | A |
| LC9 IgG | | | | | | | | | | E | V | Q | L | V | E | S | G | G | G | L | V | Q | P | G | G | S | L | R | L | S | C | A | A | S | G | F | N | F | Y | Y | S | S | I | H | W | V | R | Q | A |
| LC10 IgG | | | | | | | | | | E | V | Q | L | V | E | S | G | G | G | L | V | Q | P | G | G | S | L | R | L | S | C | A | A | S | G | F | N | F | Y | Y | S | S | I | H | W | V | R | Q | A |

| Kabat# | 41 | 42 | 43 | 44 | 45 | 46 | 47 | 48 | 49 | 50 | 51 | 52 | A | B | C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|---|---|---|---|---|---|---|---|---|---|---|---|---|---|---|
| Fab12 | P | G | K | G | L | E | W | V | A | A | S | I | S | P | | Y | S | G | Y | T | S | Y | A | D | S | V | K | G | R | F | T | I | S | A | D | T | S | K | N | T | A |
| LC6 IgG | P | G | K | G | L | E | W | V | A | A | S | I | S | P | | Y | S | G | Y | T | S | Y | A | D | S | V | K | G | R | F | T | I | S | A | D | T | S | K | N | T | A |
| LC9 IgG | P | G | K | G | L | E | W | V | A | A | S | I | S | P | | Y | S | G | Y | T | S | Y | A | D | S | V | K | G | R | F | T | I | S | A | D | T | S | K | N | T | A |
| LC10 IgG | P | G | K | G | L | E | W | V | A | A | S | I | S | P | | Y | S | G | Y | T | S | Y | A | D | S | V | K | G | R | F | T | I | S | A | D | T | S | K | N | T | A |

| Kabat# | 79 | 80 | 81 | 82 | A | B | C | 83 | 84 | 85 | 86 | 87 | 88 | 89 | 90 | 91 | 92 | 93 | 94 | 95 | 96 | 97 | 98 | 99 | 100 | A | B | C | D | E | F | G | H | K | 101 | 102 | 103 | 104 | 105 | 106 | 107 | 108 | 109 | 110 | 111 | 112 | 113 | SEQ ID NO: |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Fab12 | Y | L | Q | M | N | S | L | R | A | E | D | T | A | V | Y | Y | C | A | R | Q | P | T | H | Y | Y | Y | Y | A | K | G | Y | K | A | M | D | Y | W | G | Q | G | T | L | V | T | V | S | S | 13 |
| LC6 IgG | Y | L | Q | M | N | S | L | R | A | E | D | T | A | V | Y | Y | C | A | R | Q | P | T | H | Y | Y | Y | Y | A | K | G | Y | K | A | M | D | Y | W | G | Q | G | T | L | V | T | V | S | S | 13 |
| LC9 IgG | Y | L | Q | M | N | S | L | R | A | E | D | T | A | V | Y | Y | C | A | R | Q | P | T | H | Y | Y | Y | Y | A | K | G | Y | K | A | M | D | Y | W | G | Q | G | T | L | V | T | V | S | S | 13 |
| LC10 IgG | Y | L | Q | M | N | S | L | R | A | E | D | T | A | V | Y | Y | C | A | R | Q | P | T | H | Y | Y | Y | Y | A | K | G | Y | K | A | M | D | Y | W | G | Q | G | T | L | V | T | V | S | S | 13 |

*FIG. 6B*

```
  1  EVQLVESGGG  LVQPGGSLRL  SCAASGFTFS  SYGMSWVRQA  PGKGLELVAS
 51  INSNGGSTYY  PDSVKGRFTI  SRDNAKNSLY  LQMNSLRAED  TAVYYCASGD
101  YWGQGTTVTV  SSASTKGPSV  FPLAPCSRST  SESTAALGCL  VKDYFPEPVT
151  VSWNSGALTS  GVHTFPAVLQ  SSGLYSLSSV  VTVPSSSLGT  KTYTCNVDHK
201  PSNTKVDKRV  ESKYGPPCPP  CPAPEFLGGP  SVFLFPPKPK  DTLMISRTPE
251  VTCVVVDVSQ  EDPEVQFNWY  VDGVEVHNAK  TKPREEQFNS  TYRVVSVLTV
301  LHQDWLNGKE  YKCKVSNKGL  PSSIEKTISK  AKGQPREPQV  YTLPPSQEEM
351  TKNQVSLTCL  VKGFYPSDIA  VEWESNGQPE  NNYKTTPPVL  DSDGSFFLYS
401  RLTVDKSRWQ  EGNVFSCSVM  HEALHNHYTQ  KSLSLSLG  (SEQ ID NO: 14)
```

FIG. 7A

```
  1  DIVMTQSPLS  LPVTPGEPAS  ISCRSSQSLV  YSNGDTYLHW  YLQKPGQSPQ
 51  LLIYKVSNRF  SGVPDRFSGS  GSGTDFTLKI  SRVEAEDVGV  YYCSQSTHVP
101  WTFGQGTKVE  IKRTVAAPSV  FIFPPSDEQL  KSGTASVVCL  LNNFYPREAK
151  VQWKVDNALQ  SGNSQESVTE  QDSKDSTYSL  SSTLTLSKAD  YEKHKVYACE
201  VTHQGLSSPV  TKSFNRGEC  (SEQ ID NO: 15)
```

FIG. 7B

LOW AFFINITY BLOOD BRAIN BARRIER RECEPTOR ANTIBODIES AND USES THEREOF

RELATED APPLICATIONS

This application is a continuation of U.S. application Ser. No. 15/435,658, filed Feb. 17, 2017, which is a division of U.S. application Ser. No. 14/577,006, filed Dec. 19, 2014; which is a continuation of U.S. application Ser. No. 13/306,524, filed Nov. 29, 2011; which claims priority under 35 U.S.C. § 119(e) to U.S. provisional application No. 61/418,223, filed Nov. 30, 2010, the contents of all of which are incorporated in their entirety herein by reference.

REFERENCE TO SEQUENCE LISTING SUBMITTED AS A TEXT FILE VIA EFS-WEB

A sequence listing is submitted concurrently with the specification as an ASCII formatted text file via EFS-Web, with a file name of "2018-09-14_01146-0048-03US_SeqList.txt", a creation date of Sep. 13, 2018, and a size of 19,746 bytes. The sequence listing filed via EFS-Web is part of the specification and is hereby incorporated by reference in its entirety.

FIELD OF THE INVENTION

The present invention relates to antibodies that bind blood brain barrier receptors (BBB-R) and methods of using the same.

BACKGROUND

Brain penetration of large molecule drugs is severely limited by the largely impermeable blood-brain barrier (BBB). Among the many strategies to overcome this obstacle is to utilize transcytosis trafficking pathways of endogenous receptors expressed at the brain capillary endothelium. Recombinant proteins such as monoclonal antibodies have been designed against these receptors to enable receptor-mediated delivery of large molecules to the brain. However, strategies to maximize brain uptake while minimizing reverse transcytosis back to the blood, and the extent of accumulation after therapeutic dosing, remain unexplored. Furthermore, whether antibodies that cross the BBB are pharmacodynamically functional is unknown.

SUMMARY

Monoclonal antibodies have vast therapeutic potential for treatment of neurological or central nervous system (CNS) diseases, but their passage into the brain is restricted by the blood-brain barrier (BBB). Past studies have shown that a very small percentage (approximately 0.1%) of an IgG circulating in the bloodstream crosses through the BBB into the CNS (Felgenhauer, Klin. Wschr. 52: 1158-1164 (1974)), where the CNS concentration of the antibody may be insufficient to permit a robust effect. The methods and compositions of the invention provide a way to improve the percentage of the antibody that distributes into the CNS and thus more readily attain therapeutic antibody concentrations in the CNS.

Herein is described a group of antibodies against the transferrin receptor (TfR) that can deliver therapeutics including antibodies and small molecules across the BBB at both trace and therapeutically relevant doses after a single systemic injection in mice. Distribution of antibody changed from vascular to neuronal 24 hours after injection, indicating that a significant amount of antibody had transcytosed through brain endothelial cells to reach the parenchyma. The magnitude of antibody uptake into and distribution in the CNS was inversely related to its binding affinity to TfR for the anti-TfR variants studied. Proof of BBB transport was achieved using a bispecific antibody that binds both TfR and the amyloid precursor protein (APP) cleavage enzyme, β-secretase (BACE1). A single systemic dose of the bispecific anti-TfR/BACE1 antibody engineered using the methodology of the invention not only resulted in significant antibody uptake in brain, but also dramatically reduced levels of brain $A\beta_{1-40}$ compared to monospecific anti-BACE1 alone, suggesting that BBB penetrance affects the potency of anti-BACE1. Similarly, a bispecific antibody that binds both TfR and amyloid beta (i.e., a portion of APP that results from BACE1 cleavage of APP, which is one of the main constituents of amyloid plaques) was shown to be readily taken up into the brain using the methodology of the invention. The data and experiments described herein highlight several causative mechanisms behind increasing uptake of an antibody into the CNS using a lower-affinity antibody approach. First, high affinity anti-BBB receptor (BBB-R) antibodies (e.g., anti-TfR$^A$) limit brain uptake by quickly saturating the BBB-R in the brain vasculature, thus reducing the total amount of antibody taken up into the brain and also restricting its distribution to the vasculature. Strikingly, lowering affinity for the BBB-R improves brain uptake and distribution, with a robust shift observed in localization from the vasculature to neurons and associated neuropil distributed within the CNS. Second, the lower affinity of the antibody for the BBB-R is proposed to impair the ability of the antibody to return to the vascular side of the BBB via the BBB-R from the CNS side of the membrane because the overall affinity of the antibody for the BBB-R is low and the local concentration of the antibody on the CNS side of the BBB is non-saturating due to the rapid dispersal of the antibody into the CNS compartment. Third, in vivo, and as observed for the TfR system, antibodies with less affinity for the BBB-R are not cleared from the system as efficiently as those with greater affinity for the BBB-R, and thus remain at higher circulating concentrations than their higher-affinity counterparts. This is advantageous because the circulating antibody levels of the lower-affinity antibody are sustained at therapeutic levels for a longer period of time than the higher-affinity antibody, which consequently improves uptake of antibody in brain for a longer period of time. Furthermore, this improvement in both plasma and brain exposure may reduce the frequency of dosing in the clinic, which would have potential benefit not only for patient compliance and convenience but also in lessening any potential side effects or off-target effects of the antibody and/or of a therapeutic compound coupled thereto. Anti-TfR/BACE1 and anti-TfR/Abeta are each promising and novel therapeutic candidates for the treatment of Alzheimer's disease. Furthermore, receptor mediated transport (RMT)-based bispecific targeting technology opens the door for a wide range of potential therapeutics for CNS diseases. The invention provides methods of engineering BBB-penetrant therapeutics that greatly improve transport across the BBB and CNS distribution of the therapeutic.

Accordingly, in a first embodiment, the invention provides a method of transporting a compound across the blood-brain barrier comprising exposing an antibody which binds with low affinity to a blood-brain barrier receptor (BBB-R) coupled to a compound to the blood-brain barrier such that the antibody transports the compound coupled thereto across the blood-brain barrier. In one aspect, the compound is a neurological disorder drug. In another aspect, the compound is an imaging agent. In another aspect, the compound is labeled. In another aspect, the antibody is labeled. In another aspect, the antibody does not impair the binding of the BBB-R to one or more of its native ligands. In another such aspect, the antibody specifically binds to TfR in such a manner that it does not inhibit binding of the TfR to transferrin. In another aspect, the BBB is in a mammal. In another such aspect, the mammal is a human. In another such aspect, the mammal has a neurological disorder. In another such aspect, the neurological disorder is selected from the group consisting of Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, and traumatic brain injury. In another aspect, the BBB is in a human.

In another aspect, the antibody has an IC50 for the BBB-R from about 1 nM to about 100 µM. In another such aspect, the IC50 is from about 5 nM to about 100 µM. In another such aspect, the IC50 is from about 50 nM to about 100 µM. In another such aspect, the IC50 is from about 100 nM to about 100 µM. In another aspect, the antibody has an affinity for the BBB-R from about 5 nM to about 10 µM. In another such aspect, the antibody, when coupled to a compound, has an affinity for the BBB-R from about 30 nM to about 1 µM. In another such aspect, the antibody, when coupled to a compound, has an affinity for the BBB-R from about 50 nM to about 1 µM. In another such aspect, the compound-coupled antibody specifically binds to TfR and has an affinity for TfR between those affinities observed for the anti-TfR$^A$/BACE1 antibody and the anti-TfR$^E$/BACE1 antibody. In another such aspect, the compound-coupled antibody specifically binds to TfR and has an affinity for TfR between those affinities observed for the anti-TfR$^D$/BACE1 antibody and the anti-TfR$^E$/BACE1 antibody. In another such aspect, the compound-coupled antibody specifically binds to TfR and has an IC50 for TfR between those IC50s observed for the anti-TfR$^A$/BACE1 antibody and the anti-TfR$^E$/BACE1 antibody. In another such aspect, the compound-coupled antibody specifically binds to TfR and has an IC50 for TfR between those IC50s observed for the anti-TfR$^D$/BACE1 antibody and the anti-TfR$^E$/BACE1 antibody. In one aspect, the affinity of the anti-BBB-R or anti-BBB-R/compound for the BBB-R is measured using scatchard analysis. In another aspect, the affinity of the anti-BBB-R or anti-BBB-R/compound for the BBB-R is measured using BIACORE analysis. In another aspect, the affinity of the anti-BBB-R or anti-BBB-R/compound for the BBB-R is measured using a competition ELISA.

In another aspect, the BBB-R is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF). In another such aspect, the BBB-R is a human BBB-R. In one such aspect, the BBB-R is TfR. In another such aspect, the BBB-R is TfR and the antibody does not inhibit TfR activity. In another such aspect, the BBB-R is TfR and the antibody does not inhibit the binding of TfR to transferrin. In another aspect, the compound-coupled antibody is administered at a therapeutic dose. In one such aspect, the therapeutic dose is a dose that saturates the BBB-R to which the antibody specifically binds.

In another aspect, the compound is covalently coupled to the antibody. In one such aspect, the compound is joined to the antibody by a linker. In one such aspect, the linker is cleavable. In another such aspect, the linker is not cleavable. In another such aspect, the compound is directly linked to the antibody. In one such aspect, the antibody is a multispecific antibody and the compound forms one portion of the multispecific antibody. In another such aspect, the multispecific antibody comprises a first antigen binding site which binds the BBB-R and a second antigen binding site which binds a brain antigen. In another such aspect, the brain antigen is selected from the group consisting of: beta-secretase 1 (BACE1), Abeta, epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), and caspase 6. In another such aspect, the multispecific antibody binds both TfR and BACE1. In another such aspect, the multispecific antibody binds both TfR and Abeta. In another such aspect, the multispecific antibody is labeled. In another aspect, the compound is reversibly coupled to the antibody such that the compound is released from the antibody concurrent with or after BBB transport.

In another embodiment, the invention provides a method of increasing exposure of the CNS to a compound, wherein the compound is coupled to an antibody which binds with low affinity to a BBB-R, thereby increasing the exposure of the CNS to the compound. In one aspect, the compound is a neurological disorder drug. In another aspect, the compound is an imaging agent. In another aspect, the compound is labeled. In another aspect, the antibody is labeled. In another aspect, the antibody does not impair the binding of the BBB-R to one or more of its native ligands. In another such aspect, the antibody specifically binds to TfR in such a manner that it does not inhibit binding of the TfR to transferrin. In another aspect, the antibody-coupled compound is administered to a mammal. In another such aspect, the mammal is a human. In another such aspect, the mammal has a neurological disorder. In another such aspect, the neurological disorder is selected from the group consisting of Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, and traumatic brain injury.

In another aspect, the increase in CNS exposure to the compound is measured relative to the CNS exposure of a compound coupled with a typical antibody not having lowered affinity for the BBB-R. In another aspect, the increase in CNS exposure to the compound is measured as a ratio of the amount of the compound found in the CNS relative to the amount found in the serum after administration. In another such aspect, the increase in CNS exposure results in a ratio of greater than 0.1%. In another aspect, the increase in CNS exposure to the compound is measured relative to the CNS exposure of a compound in the absence of a coupled antibody. In another aspect, the increase in CNS exposure to the compound is measured by imaging. In another aspect, the increase in CNS exposure to the compound is measured by an indirect readout such as a modification of one or more physiological symptoms.

In another aspect, the antibody has an IC50 for the BBB-R from about 1 nM to about 100 μM. In another such aspect, the IC50 is from about 5 nM to about 100 μM. In another such aspect, the IC50 is from about 50 nM to about 100 μM. In another such aspect, the IC50 is from about 100 nM to about 100 μM. In another aspect, the antibody has an affinity for the BBB-R from about 5 nM to about 10 μM. In another such aspect, the antibody, when coupled to a compound, has an affinity for the BBB-R from about 30 nM to about 1 μM. In another such aspect, the antibody, when coupled to a compound, has an affinity for the BBB-R from about 50 nM to about 1 μM. In another such aspect, the compound-coupled antibody specifically binds to TfR and has an affinity for TfR between those affinities observed for the anti-TfR$^A$/BACE1 antibody and the anti-TfR$^E$/BACE1 antibody. In another such aspect, the compound-coupled antibody specifically binds to TfR and has an affinity for TfR between those affinities observed for the anti-TfR$^D$/BACE1 antibody and the anti-TfR$^E$/BACE1 antibody. In another such aspect, the compound-coupled antibody specifically binds to TfR and has an IC50 for TfR between those IC50s observed for the anti-TfR$^A$/BACE1 antibody and the anti-TfR$^E$/BACE1 antibody. In another such aspect, the compound-coupled antibody specifically binds to TfR and has an IC50 for TfR between those IC50s observed for the anti-TfR$^D$/BACE1 antibody and the anti-TfR$^E$/BACE1 antibody. In one aspect, the affinity of the anti-BBB-R or anti-BBB-R/compound for the BBB-R is measured using scatchard analysis. In another aspect, the affinity of the anti-BBB-R or anti-BBB-R/compound for the BBB-R is measured using BIACORE analysis. In another aspect, the affinity of the anti-BBB-R or anti-BBB-R/compound for the BBB-R is measured using a competition ELISA.

In another aspect, the BBB-R is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF). In another such aspect, the BBB-R is a human BBB-R. In one such aspect, the BBB-R is TfR. In another such aspect, the BBB-R is TfR and the antibody does not inhibit TfR activity. In another such aspect, the BBB-R is TfR and the antibody does not inhibit the binding of TfR to transferrin. In another aspect, the compound-coupled antibody is administered at a therapeutic dose. In one such aspect, the therapeutic dose is a dose that saturates the BBB-R to which the antibody specifically binds.

In another aspect, the compound is covalently coupled to the antibody. In one such aspect, the compound is joined to the antibody by a linker. In one such aspect, the linker is cleavable. In another such aspect, the linker is not cleavable. In another such aspect, the compound is directly linked to the antibody. In one such aspect, the antibody is a multispecific antibody and the compound forms one portion of the multispecific antibody. In another such aspect, the multispecific antibody comprises a first antigen binding site which binds the BBB-R and a second antigen binding site which binds a brain antigen. In another such aspect, the brain antigen is selected from the group consisting of: beta-secretase 1 (BACE1), Abeta, epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), and caspase 6.

In another such aspect, the multispecific antibody binds both TfR and BACE1. In another such aspect, the multispecific antibody binds both TfR and Abeta. In another such aspect, the multispecific antibody is labeled. In another aspect, the compound is reversibly coupled to the antibody such that the compound is released from the antibody concurrent with or after BBB transport.

In another embodiment, the invention provides a method of decreasing clearance of a compound administered to a subject, wherein the compound is coupled to an antibody which binds with low affinity to a BBB-R, such that the clearance of the compound is decreased. In one aspect, the compound is a neurological disorder drug. In another aspect, the compound is an imaging agent. In another aspect, the compound is labeled. In another aspect, the antibody is labeled. In another aspect, the antibody does not impair the binding of the BBB-R to one or more of its native ligands. In another such aspect, the antibody specifically binds to TfR in such a manner that it does not inhibit binding of the TfR to transferrin. In another aspect, the subject is a mammal. In another such aspect, the mammal is a human. In another such aspect, the mammal has a neurological disorder. In another such aspect, the neurological disorder is selected from the group consisting of Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, and traumatic brain injury.

In another aspect, the decrease in clearance of the compound is measured relative to the clearance of a compound coupled with a typical antibody not having lowered affinity for the BBB-R. In another aspect, the decrease in clearance of the compound is measured relative to the clearance of the compound in the absence of a coupled antibody.

In another aspect, the antibody has an IC50 for the BBB-R from about 1 nM to about 100 μM. In another such aspect, the IC50 is from about 5 nM to about 100 μM. In another such aspect, the IC50 is from about 50 nM to about 100 μM. In another such aspect, the IC50 is from about 100 nM to about 100 μM. In another aspect, the antibody has an affinity for the BBB-R from about 5 nM to about 10 μM. In another such aspect, the antibody, when coupled to a compound, has an affinity for the BBB-R from about 30 nM to about 1 μM. In another such aspect, the antibody, when coupled to a compound, has an affinity for the BBB-R from about 50 nM to about 1 μM. In another such aspect, the compound-coupled antibody specifically binds to TfR and has an affinity for TfR between those affinities observed for the anti-TfR$^A$/BACE1 antibody and the anti-TfR$^E$/BACE1 antibody. In another such aspect, the compound-coupled antibody specifically binds to TfR and has an affinity for TfR between those affinities observed for the anti-TfR$^D$/BACE1 antibody and the anti-TfR$^E$/BACE1 antibody. In another such aspect, the compound-coupled antibody specifically binds to TfR and has an IC50 for TfR between those IC50s observed for the anti-TfR$^A$/BACE1 antibody and the anti-TfR$^E$/BACE1 antibody. In another such aspect, the compound-coupled antibody specifically binds to TfR and has an IC50 for TfR between those IC50s observed for the anti-TfR$^D$/BACE1 antibody and the anti-TfR$^E$/BACE1 antibody. In one aspect, the affinity of the anti-BBB-R or anti-BBB-R/compound for the BBB-R is measured using scatchard analysis. In another aspect, the affinity of the anti-BBB-R or anti-BBB-R/compound for the BBB-R is measured using BIACORE analysis. In another aspect, the affinity of the anti-BBB-R or anti-BBB-R/compound for the BBB-R is measured using a competition ELISA.

In another aspect, the BBB-R is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF). In another such aspect, the BBB-R is a human BBB-R. In one such aspect, the BBB-R is TfR. In another such aspect, the BBB-R is TfR and the antibody does not inhibit TfR activity. In another such aspect, the BBB-R is TfR and the antibody does not inhibit the binding of TfR to transferrin. In another aspect, the compound-coupled antibody is administered at a therapeutic dose. In one such aspect, the therapeutic dose is a dose that saturates the BBB-R to which the antibody specifically binds.

In another aspect, the compound is covalently coupled to the antibody. In one such aspect, the compound is joined to the antibody by a linker. In one such aspect, the linker is cleavable. In another such aspect, the linker is not cleavable. In another such aspect, the compound is directly linked to the antibody. In one such aspect, the antibody is a multispecific antibody and the compound forms one portion of the multispecific antibody. In another such aspect, the multispecific antibody comprises a first antigen binding site which binds the BBB-R and a second antigen binding site which binds a brain antigen. In another such aspect, the brain antigen is selected from the group consisting of: beta-secretase 1 (BACE1), Abeta, epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), and caspase 6. In another such aspect, the multispecific antibody binds both TfR and BACE1. In another such aspect, the multispecific antibody binds both TfR and Abeta. In another such aspect, the multispecific antibody is labeled. In another aspect, the compound is reversibly coupled to the antibody such that the compound is released from the antibody concurrent with or after BBB transport.

A method of increasing retention in the CNS of a compound administered to a subject, wherein the compound is coupled to an antibody which binds with low affinity to a BBB-R, such that the retention in the CNS of the compound is increased. In one aspect, the compound is a neurological disorder drug. In another aspect, the compound is an imaging agent. In another aspect, the compound is labeled. In another aspect, the antibody is labeled. In another aspect, the antibody does not impair the binding of the BBB-R to one or more of its native ligands. In another such aspect, the antibody specifically binds to TfR in such a manner that it does not inhibit binding of the TfR to transferrin. In another aspect, the compound is administered to a mammal. In another such aspect, the mammal is a human. In another such aspect, the mammal has a neurological disorder. In another such aspect, the neurological disorder is selected from the group consisting of Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, and traumatic brain injury.

In another aspect, the increase in CNS retention of the compound is measured relative to the CNS retention of a compound coupled with a typical antibody not having lowered affinity for the BBB-R. In another aspect, the increase in CNS retention of the compound is measured as a ratio of the amount of the compound found in the CNS relative to the amount found in the serum at one or more time points after administration. In another such aspect, the increase in CNS retention results in a ratio of greater than 0.1% at one or more time points after administration. In another aspect, the increase in CNS retention of the compound is measured relative to the CNS retention of a compound in the absence of a coupled antibody. In another aspect, the increase in CNS retention of the compound is measured by imaging. In another aspect, the increase in CNS retention of the compound is measured by an indirect readout such as a modification of one or more physiological symptoms.

In another aspect, the antibody has an IC50 for the BBB-R from about 1 nM to about 100 µM. In another such aspect, the IC50 is from about 5 nM to about 100 µM. In another such aspect, the IC50 is from about 50 nM to about 100 µM. In another such aspect, the IC50 is from about 100 nM to about 100 µM. In another aspect, the antibody has an affinity for the BBB-R from about 5 nM to about 10 µM. In another such aspect, the antibody, when coupled to a compound, has an affinity for the BBB-R from about 30 nM to about 1 µM. In another such aspect, the antibody, when coupled to a compound, has an affinity for the BBB-R from about 50 nM to about 1 µM. In another such aspect, the compound-coupled antibody specifically binds to TfR and has an affinity for TfR between those affinities observed for the anti-TfR$^A$/BACE1 antibody and the anti-TfR$^E$/BACE1 antibody. In another such aspect, the compound-coupled antibody specifically binds to TfR and has an affinity for TfR between those affinities observed for the anti-TfR$^D$/BACE1 antibody and the anti-TfR$^E$/BACE1 antibody. In another such aspect, the compound-coupled antibody specifically binds to TfR and has an IC50 for TfR between those IC50s observed for the anti-TfR$^A$/BACE1 antibody and the anti-TfR$^E$/BACE1 antibody. In another such aspect, the compound-coupled antibody specifically binds to TfR and has an IC50 for TfR between those IC50s observed for the anti-TfR$^D$/BACE1 antibody and the anti-TfR$^E$/BACE1 antibody. In one aspect, the affinity of the anti-BBB-R or anti-BBB-R/compound for the BBB-R is measured using scatchard analysis. In another aspect, the affinity of the anti-BBB-R or anti-BBB-R/compound for the BBB-R is measured using BIACORE analysis. In another aspect, the affinity of the anti-BBB-R or anti-BBB-R/compound for the BBB-R is measured using a competition ELISA.

In another aspect, the BBB-R is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF). In another such aspect, the BBB-R is a human BBB-R. In one such aspect, the BBB-R is TfR. In another such aspect, the BBB-R is TfR and the antibody does not inhibit TfR activity. In another such aspect, the BBB-R is TfR and the antibody does not inhibit the binding of TfR to transferrin. In another aspect, the compound-coupled antibody is administered at a therapeutic dose. In one such aspect, the therapeutic dose is a dose that saturates the BBB-R to which the antibody specifically binds.

In another aspect, the compound is covalently coupled to the antibody. In one such aspect, the compound is joined to the antibody by a linker. In one such aspect, the linker is cleavable. In another such aspect, the linker is not cleavable. In another such aspect, the compound is directly linked to the antibody. In one such aspect, the antibody is a multispecific antibody and the compound forms one portion of the multispecific antibody. In another such aspect, the multispecific antibody comprises a first antigen binding site which binds the BBB-R and a second antigen binding site which binds a brain antigen. In another such aspect, the brain antigen is selected from the group consisting of: beta-secretase 1 (BACE1), Abeta, epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), and caspase 6. In another such aspect, the multispecific antibody binds both TfR and BACE1. In another such aspect, the multispecific antibody binds both TfR and Abeta. In another such aspect, the multispecific antibody is labeled. In another aspect, the compound is reversibly coupled to the antibody such that the compound is released from the antibody concurrent with or after BBB transport.

In another embodiment, the invention provides a method of optimizing the pharmacokinetics and/or pharmacodynamics of a compound to be efficacious in the CNS of a subject, wherein the compound is coupled to an antibody which binds with low affinity to a BBB-R, and the antibody is selected such that its affinity for the BBB-R after coupling to the compound results in an amount of transport of the antibody conjugated to the compound across the BBB that optimizes the pharmacokinetics and/or pharmacodynamics of the compound in the CNS. In one aspect, the compound is a neurological disorder drug. In another aspect, the compound is an imaging agent. In another aspect, the compound is labeled. In another aspect, the antibody is labeled. In another aspect, the antibody does not impair the binding of the BBB-R to one or more of its native ligands. In another such aspect, the antibody specifically binds to TfR in such a manner that it does not inhibit binding of the TfR to transferrin. In another aspect, the BBB is in a mammal. In another such aspect, the mammal is a human. In another such aspect, the mammal has a neurological disorder. In another such aspect, the neurological disorder is selected from the group consisting of Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, and traumatic brain injury. In another aspect, the BBB is in a human.

In one aspect, the optimizing may include the generation of a series of antibody-compound complexes in which each antibody has a different affinity for the BBB-R, and assessing the pharmacokinetics and/or pharmacodynamics of each in the CNS. In another aspect, optimizing may be relative to a known standard, such as, but not limited to, the pharmacokinetics and/or pharmacodynamics of the compound when directly introduced into the CNS or when introduced to the subject in the absence of a coupled anti-BBB-R antibody.

In another aspect, the antibody has an IC50 for the BBB-R from about 1 nM to about 100 μM. In another such aspect, the IC50 is from about 5 nM to about 100 μM. In another such aspect, the IC50 is from about 50 nM to about 100 μM. In another such aspect, the IC50 is from about 100 nM to about 100 μM. In another aspect, the antibody has an affinity for the BBB-R from about 5 nM to about 10 μM. In another such aspect, the antibody, when coupled to a compound, has an affinity for the BBB-R from about 30 nM to about 1 μM. In another such aspect, the antibody, when coupled to a compound, has an affinity for the BBB-R from about 50 nM to about 1 μM. In another such aspect, the compound-coupled antibody specifically binds to TfR and has an affinity for TfR between those affinities observed for the anti-TfR$^A$/BACE1 antibody and the anti-TfR$^E$/BACE1 antibody. In another such aspect, the compound-coupled antibody specifically binds to TfR and has an affinity for TfR between those affinities observed for the anti-TfR$^D$/BACE1 antibody and the anti-TfR$^E$/BACE1 antibody. In another such aspect, the compound-coupled antibody specifically binds to TfR and has an IC50 for TfR between those IC50s observed for the anti-TfR$^A$/BACE1 antibody and the anti-TfR$^E$/BACE1 antibody. In another such aspect, the compound-coupled antibody specifically binds to TfR and has an IC50 for TfR between those IC50s observed for the anti-TfR$^D$/BACE1 antibody and the anti-TfR$^E$/BACE1 antibody. In one aspect, the affinity of the anti-BBB-R or anti-BBB-R/compound for the BBB-R is measured using scatchard analysis. In another aspect, the affinity of the anti-BBB-R or anti-BBB-R/compound for the BBB-R is measured using BIACORE analysis. In another aspect, the affinity of the anti-BBB-R or anti-BBB-R/compound for the BBB-R is measured using a competition ELISA.

In another aspect, the BBB-R is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF). In another such aspect, the BBB-R is a human BBB-R. In one such aspect, the BBB-R is TfR. In another such aspect, the BBB-R is TfR and the antibody does not inhibit TfR activity. In another such aspect, the BBB-R is TfR and the antibody does not inhibit the binding of TfR to transferrin. In another aspect, the compound-coupled antibody is administered at a therapeutic dose. In one such aspect, the therapeutic dose is a dose that saturates the BBB-R to which the antibody specifically binds.

In another aspect, the compound is covalently coupled to the antibody. In one such aspect, the compound is joined to the antibody by a linker. In one such aspect, the linker is cleavable. In another such aspect, the linker is not cleavable. In another such aspect, the compound is directly linked to the antibody. In one such aspect, the antibody is a multispecific antibody and the compound forms one portion of the multispecific antibody. In another such aspect, the multispecific antibody comprises a first antigen binding site which binds the BBB-R and a second antigen binding site which binds a brain antigen. In another such aspect, the brain antigen is selected from the group consisting of: beta-secretase 1 (BACE1), Abeta, epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), and caspase 6. In another such aspect, the multispecific antibody binds both TfR and BACE1. In another such aspect, the multispecific antibody binds both TfR and Abeta. In another such aspect, the multispecific antibody is labeled. In another aspect, the compound is reversibly coupled to the antibody such that the compound is released from the antibody concurrent with or after BBB transport.

In another embodiment the invention provides a method of treating a neurological disorder in a mammal comprising treating the mammal with an antibody that binds a BBB-R and is coupled to a compound, wherein the antibody has been selected to have a low affinity for the BBB-R and thereby improves CNS uptake of the antibody and coupled compound. In one aspect, the compound is a neurological disorder drug. In another aspect, the compound is an imaging agent. In another aspect, the compound is labeled. In another aspect, the antibody is labeled. In another aspect, the antibody does not impair the binding of the BBB-R to one or more of its native ligands. In another such aspect, the antibody specifically binds to TfR in such a manner that it does not inhibit binding of the TfR to transferrin. In one aspect, the mammal is a human. In another such aspect, the mammal has a neurological disorder. In another such aspect, the neurological disorder is selected from the group consisting of Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, and traumatic brain injury.

In one aspect, the treating results in lessening or elimination of disorder symptoms. In another aspect, the treating results in amelioration of the neurological disorder.

In another aspect, the antibody has an IC50 for the BBB-R from about 1 nM to about 100 µM. In another such aspect, the IC50 is from about 5 nM to about 100 µM. In another such aspect, the IC50 is from about 50 nM to about 100 µM. In another such aspect, the IC50 is from about 100 nM to about 100 µM. In another aspect, the antibody has an affinity for the BBB-R from about 5 nM to about 10 µM. In another such aspect, the antibody, when coupled to a compound, has an affinity for the BBB-R from about 30 nM to about 1 µM. In another such aspect, the antibody, when coupled to a compound, has an affinity for the BBB-R from about 50 nM to about 1 µM. In another such aspect, the compound-coupled antibody specifically binds to TfR and has an affinity for TfR between those affinities observed for the anti-TfR$^A$/BACE1 antibody and the anti-TfR$^E$/BACE1 antibody. In another such aspect, the compound-coupled antibody specifically binds to TfR and has an affinity for TfR between those affinities observed for the anti-TfR$^D$/BACE1 antibody and the anti-TfR$^E$/BACE1 antibody. In another such aspect, the compound-coupled antibody specifically binds to TfR and has an IC50 for TfR between those IC50s observed for the anti-TfR$^A$/BACE1 antibody and the anti-TfR$^E$/BACE1 antibody. In another such aspect, the compound-coupled antibody specifically binds to TfR and has an IC50 for TfR between those IC50s observed for the anti-TfR$^D$/BACE1 antibody and the anti-TfR$^E$/BACE1 antibody. In one aspect, the affinity of the anti-BBB-R or anti-BBB-R/compound for the BBB-R is measured using scatchard analysis. In another aspect, the affinity of the anti-BBB-R or anti-BBB-R/compound for the BBB-R is measured using BIACORE analysis. In another aspect, the affinity of the anti-BBB-R or anti-BBB-R/compound for the BBB-R is measured using a competition ELISA.

In another aspect, the BBB-R is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF). In another such aspect, the BBB-R is a human BBB-R. In one such aspect, the BBB-R is TfR. In another such aspect, the BBB-R is TfR and the antibody does not inhibit TfR activity. In another such aspect, the BBB-R is TfR and the antibody does not inhibit the binding of TfR to transferrin. In another aspect, the compound-coupled antibody is administered at a therapeutic dose. In one such aspect, the therapeutic dose is a dose that saturates the BBB-R to which the antibody specifically binds.

In another aspect, the compound is covalently coupled to the antibody. In one such aspect, the compound is joined to the antibody by a linker. In one such aspect, the linker is cleavable. In another such aspect, the linker is not cleavable. In another such aspect, the compound is directly linked to the antibody. In one such aspect, the antibody is a multispecific antibody and the compound forms one portion of the multispecific antibody. In another such aspect, the multispecific antibody comprises a first antigen binding site which binds the BBB-R and a second antigen binding site which binds a brain antigen. In another such aspect, the brain antigen is selected from the group consisting of: beta-secretase 1 (BACE1), Abeta, epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), and caspase 6. In another such aspect, the multispecific antibody binds both TfR and BACE1. In another such aspect, the multispecific antibody binds both TfR and Abeta. In another such aspect, the multispecific antibody is labeled. In another aspect, the compound is reversibly coupled to the antibody such that the compound is released from the antibody concurrent with or after BBB transport.

In another embodiment, the invention provides a method of making an antibody useful for transporting a compound across the BBB comprising selecting an antibody specific for a blood-brain barrier receptor (BBB-R) because it has a desirably low affinity for the BBB-R.

In one aspect, the antibody is selected from a panel of antibodies based upon the affinity of the selected antibody. In another aspect, the antibody is engineered to have the affinity. In one such aspect, the antibody is generated using any art-known protein engineering methodology including, but not limited to, phage display, yeast display, random mutagenesis, and site-directed mutagenesis.

In one aspect, the compound is a neurological disorder drug. In another aspect, the compound is an imaging agent. In another aspect, the compound is labeled. In another aspect, the antibody is labeled. In another aspect, the antibody does not impair the binding of the BBB-R to one or more of its native ligands. In another such aspect, the antibody specifically binds to TfR in such a manner that it does not inhibit binding of the TfR to transferrin. In another aspect, the BBB is in a mammal. In another such aspect, the mammal is a human. In another such aspect, the mammal has a neurological disorder. In another such aspect, the neurological disorder is selected from the group consisting of Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, and traumatic brain injury. In another aspect, the BBB is in a human.

In another aspect, the antibody has an IC50 for the BBB-R from about 1 nM to about 100 µM. In another such aspect, the IC50 is from about 5 nM to about 100 μM. In another such aspect, the IC50 is from about 50 nM to about 100 μM. In another such aspect, the IC50 is from about 100 nM to about 100 μM. In another aspect, the antibody has an affinity for the BBB-R from about 5 nM to about 10 μM. In another such aspect, the antibody, when coupled to a compound, has an affinity for the BBB-R from about 30 nM to about 1 μM. In another such aspect, the antibody, when coupled to a compound, has an affinity for the BBB-R from about 50 nM to about 1 μM. In another such aspect, the compound-coupled antibody specifically binds to TfR and has an affinity for TfR between those affinities observed for the anti-TfR$^A$/BACE1 antibody and the anti-TfR$^E$/BACE1 antibody. In another such aspect, the compound-coupled antibody specifically binds to TfR and has an affinity for TfR between those affinities observed for the anti-TfR$^D$/BACE1 antibody and the anti-TfR$^E$/BACE1 antibody. In another such aspect, the compound-coupled antibody specifically binds to TfR and has an IC50 for TfR between those IC50s observed for the anti-TfR$^A$/BACE1 antibody and the anti-TfR$^E$/BACE1 antibody. In another such aspect, the compound-coupled antibody specifically binds to TfR and has an IC50 for TfR between those IC50s observed for the anti-TfR$^D$/BACE1 antibody and the anti-TfR$^E$/BACE1 antibody. In one aspect, the affinity of the anti-BBB-R or anti-BBB-R/compound for the BBB-R is measured using scatchard analysis. In another aspect, the affinity of the anti-BBB-R or anti-BBB-R/compound for the BBB-R is measured using BIACORE analysis. In another aspect, the affinity of the anti-BBB-R or anti-BBB-R/compound for the BBB-R is measured using a competition ELISA.

In another aspect, the BBB-R is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF). In another such aspect, the BBB-R is a human BBB-R. In one such aspect, the BBB-R is TfR. In another such aspect, the BBB-R is TfR and the antibody does not inhibit TfR activity. In another such aspect, the BBB-R is TfR and the antibody does not inhibit the binding of TfR to transferrin. In another aspect, the compound-coupled antibody is administered at a therapeutic dose. In one such aspect, the therapeutic dose is a dose that saturates the BBB-R to which the antibody specifically binds.

In another aspect, the compound is covalently coupled to the antibody. In one such aspect, the compound is joined to the antibody by a linker. In one such aspect, the linker is cleavable. In another such aspect, the linker is not cleavable. In another such aspect, the compound is directly linked to the antibody. In one such aspect, the antibody is a multispecific antibody and the compound forms one portion of the multispecific antibody. In another such aspect, the multispecific antibody comprises a first antigen binding site which binds the BBB-R and a second antigen binding site which binds a brain antigen. In another such aspect, the brain antigen is selected from the group consisting of: beta-secretase 1 (BACE1), Abeta, epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), and caspase 6. In another such aspect, the multispecific antibody binds both TfR and BACE1. In another such aspect, the multispecific antibody binds both TfR and Abeta. In another such aspect, the multispecific antibody is labeled. In another aspect, the compound is reversibly coupled to the antibody such that the compound is released from the antibody concurrent with or after BBB transport.

In another embodiment, the invention provides an antibody which binds to a blood-brain barrier receptor (BBB-R) with low affinity. In one aspect, the affinity of the antibody for the BBB-R is from about 5 nM to about 10 μM. In another aspect, the affinity of the antibody for the BBB-R is from about 20 nM to about 1 μM. In another aspect, the antibody has an IC50 for the BBB-R from about 1 nM to about 100 μM. In another such aspect, the IC50 is from about 5 nM to about 100 μM. In another such aspect, the IC50 is from about 50 nM to about 100 μM. In another such aspect, the IC50 is from about 100 nM to about 100 μM. In another such aspect, the antibody, when coupled to a compound, has an affinity for the BBB-R from about 50 nM to about 1 μM. In another such aspect, the compound-coupled antibody specifically binds to TfR and has an affinity for TfR between those affinities observed for the anti-TfR$^A$/BACE1 antibody and the anti-TfR$^E$/BACE1 antibody. In another such aspect, the compound-coupled antibody specifically binds to TfR and has an affinity for TfR between those affinities observed for the anti-TfR$^D$/BACE1 antibody and the anti-TfR$^E$/BACE1 antibody. In another such aspect, the compound-coupled antibody specifically binds to TfR and has an IC50 for TfR between those IC50s observed for the anti-TfR$^A$/BACE1 antibody and the anti-TfR$^E$/BACE1 antibody. In another such aspect, the compound-coupled antibody specifically binds to TfR and has an IC50 for TfR between those IC50s observed for the anti-TfR$^D$/BACE1 antibody and the anti-TfR$^E$/BACE1 antibody. In one aspect, the affinity of the anti-BBB-R or anti-BBB-R/compound for the BBB-R is measured using scatchard analysis. In another aspect, the affinity of the anti-BBB-R or anti-BBB-R/compound for the BBB-R is measured using BIACORE analysis. In another aspect, the affinity of the anti-BBB-R or anti-BBB-R/compound for the BBB-R is measured using a competition ELISA.

In another aspect, the BBB-R is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF). In one such aspect, the BBB-R is TfR. In another such aspect, the BBB-R is TfR and the antibody does not inhibit TfR activity. In another such aspect, the BBB-R is TfR and the antibody does not inhibit the binding of TfR to transferrin. In another such aspect, the BBB-R is a human BBB-R.

In another aspect, the antibody is coupled to a compound. In one aspect, the compound is a neurological disorder drug. In another aspect, the compound is an imaging agent. In another aspect, the compound is labeled. In another aspect, the antibody is labeled. In another aspect, the antibody does not impair the binding of the BBB-R to one or more of its native ligands. In another such aspect, the antibody specifically binds to TfR in such a manner that it does not inhibit binding of the TfR to transferrin.

In another aspect, the compound is covalently coupled to the antibody. In one such aspect, the compound is joined to the antibody by a linker. In one such aspect, the linker is cleavable. In another such aspect, the linker is not cleavable. In another such aspect, the compound is directly linked to the antibody. In one such aspect, the antibody is a multispecific antibody and the compound forms one portion of the multispecific antibody. In another such aspect, the multispecific antibody comprises a first antigen binding site which binds the BBB-R and a second antigen binding site which binds a brain antigen. In another such aspect, the brain antigen is selected from the group consisting of: beta-secretase 1 (BACE1), Abeta, epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), and caspase 6. In another such aspect, the multispecific antibody binds both TfR and BACE1. In another such aspect, the multispecific antibody binds both TfR and Abeta. In another such aspect, the multispecific antibody is labeled. In another aspect, the compound is reversibly coupled to the antibody such that the compound is released from the antibody concurrent with or after BBB transport.

In another aspect, the antibody is an antibody fragment with an antigen-binding region that binds the BBB-R, including, but not limited to, Fab, Fab', F(ab')$_2$, and Fv. In another aspect, the antibody is a full-length antibody.

In another embodiment, the invention provides the use of an antibody that binds with low affinity to a BBB-R for the manufacture of a medicament for treating a neurological disorder. Any of the foregoing described low-affinity anti-BBB-R antibodies or any of the low-affinity anti-BBB-R antibodies described elsewhere herein may be used in the method.

In another embodiment, the invention provides an antibody that binds with low affinity to a BBB-R for use in treating a neurological disorder. Any of the foregoing described low-affinity anti-BBB-R antibodies or any of the low-affinity anti-BBB-R antibodies described elsewhere herein may be used in the method. Accordingly, in a first aspect, the invention provides an antibody which binds to a blood-brain barrier receptor (BBB-R), wherein the affinity of the antibody for the BBB-R is from about 5 nM to about 10 μM (e.g. from about 20 nM to about 1 μM). Optionally, the BBB-R is selected from the group consisting of transferrin receptor (TfR), insulin receptor, insulin-like growth factor receptor (IGF receptor), low density lipoprotein receptor-related protein 1 (LRP1), low density lipoprotein receptor-related protein 8 (LRP8), and heparin-binding epidermal growth factor-like growth factor (HB-EGF). Optionally, the antibody is coupled with a therapeutic compound, such as a neurological disorder drug. In one embodiment, the antibody is a multispecific antibody which comprises a first antigen binding site which binds the BBB-R and a second antigen binding site which binds a brain antigen, for instance where the brain antigen is selected from the group consisting of: beta-secretase 1 (BACE1), amyloid beta (Abeta), epidermal growth factor receptor (EGFR), human epidermal growth factor receptor 2 (HER2), Tau, apolipoprotein A3 (ApoE3), apolipoprotein E4 (ApoE4), alpha-synuclein, CD20, Huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), and caspase 6. The antibody (e.g. multispecific antibody) includes antibody fragments and full-length antibodies.

In another embodiment, the invention provides a method of transporting a therapeutic compound, such as a neurological disorder drug, across the blood-brain barrier comprising exposing the anti-BBB-R antibody coupled with a neurological disorder drug to the blood-brain barrier such that the antibody transports the neurological disorder drug coupled thereto across the blood-brain barrier. The blood-brain barrier in this method may be in a mammal, e.g. one with a neurological disorder, examples of which include: Alzheimer's disease (AD) (including, but not limited to, mild cognitive impairment and prodromal AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer (e.g. cancer affecting the CNS or brain), and traumatic brain injury.

The invention additionally concerns a method of making an antibody useful for transporting a therapeutic compound such as a neurological disorder drug across the blood-brain barrier comprising selecting an antibody against a blood-brain barrier receptor (BBB-R) because it has an affinity for the BBB-R which is from about 5 nM to about 10 μM. In one embodiment the antibody is selected from a panel of antibodies because it has the desired affinity. Alternatively, or additionally, the antibody is engineered to have the desired affinity. The method optionally further comprises coupling the antibody with a therapeutic compound such as a neurological disorder drug. For example, the method can comprise making a multispecific antibody which comprises a first antigen binding site which binds the BBB-R and a second antigen binding site which binds a brain antigen.

The invention additionally provides a method of treating a neurological disorder in a mammal comprising treating the mammal with a multispecific antibody that binds both a blood-brain barrier receptor (BBB-R) and a brain antigen, wherein the anti-BBB-R antibody has been selected to have a low affinity for the BBB-R and thereby improves brain uptake of the anti-brain antigen antibody. Optionally, the multispecific antibody binds both transferrin receptor (TfR) and BACE1 or Abeta.

It will be understood that any of the foregoing methods and compositions of the invention may be combined with one another and/or with the further aspects of the invention described in the specification herein.

BRIEF DESCRIPTION OF THE FIGURES

FIG. 1A shows brain uptake after IV administration of trace doses (approximately 50 μg/kg) of [$^{131}$I]anti-TfR$^A$ and [$^{125}$I]control IgG in mice and was quantified as a mean percentage of injected dose per gram of brain at 5, 30 min., 1, 4, 24, 48, and 72 hours after IV injection (n=6). Uptake of [$^{131}$I]anti-TfR$^A$ was decreased by injection with 4 mg/kg unlabeled anti-TfR$^A$ (cold). FIG. 1B shows quantification of mean antibody uptake in brain 1 and 24 hours after a 20 mg/kg IV injection of control IgG or anti-TfR$^A$ (*p=0.0002, n=10). FIG. 1C shows ratio of mean percent brain to serum concentrations (p=0.003, n=10). FIGS. 1D and 1E depict immunohistochemical staining of brain sections following IV-injection with anti-TfR$^A$ (FIG. 1D, upper panels), which shows co-localization with anti-collagen IV, a vascular marker (lower panel). IV-injection with control IgG (FIG. 1E, upper panels) exhibits vascular distribution in brain only after 1 hour and an absence of antibody after 24 hours. Scale bar=50 μm.

FIGS. 2A-F show that affinity of anti-TfR antibodies and extent of brain uptake are inversely related when administered at a therapeutically relevant dose (20 mg/kg) as compared to a low trace dose (approximately 50 µg/kg). FIG. 2A depicts a competitive binding ELISA in which increasing concentrations of anti-TfR$^{A,B,C,D,E}$ variant antibodies are used to compete against biotinylated TfR$^A$ for binding to TfR. The anti-TfR competition ELISA was performed in Maxisorp plates (Neptune, N.J.) coated with 2.5 µg/ml of purified murine TfR extracellular domain in PBS at 4° C. overnight. Plates were washed with PBS/0.05% Tween 20 and blocked using Superblock blocking buffer in PBS (Thermo Scientific, Hudson, N.H.). A titration of anti-TfR$^A$, anti-TfR$^B$, anti-TfR$^C$, or anti-TfR$^D$ (1:3 serial dilution) was combined with biotinylated anti-TfR$^A$ (0.5 nM final concentration) and added to the plate for 1 hour at room temperature. Plates were washed with PBS/0.05% Tween 20, and HRP-streptavidin (Southern Biotech, Birmingham) was added to the plate and incubated for 1 hour at room temperature. Plates were washed with PBS/0.05% Tween 20, and biotinylated anti-TfR$^A$ bound to the plate was detected using TMB substrate (BioFX Laboratories, Owings Mills). The results in FIG. 2A present data from a single experiment in which all five anti-TfR variants were separately assessed. The IC50 values determined from this data are shown in Table 2. FIG. 2B depicts quantification of mean brain uptake after IV-injection of trace doses (approximately 50 µg/kg) of the [$^{125}$I]anti-TfR$^{A,B,C,D,E}$ variants after 5 min., 1, 4, 6, and 24 hours (n=3). The results in FIG. 2B present data from a single experiment in which all five anti-TfR variants were separately assessed. FIG. 2C shows quantification of mean brain uptake after 20 mg/kg IV injection of anti-TfR variants at 1 and 24 hours using the methods described with regard to FIG. 1B. The experiment was replicated under the same conditions using anti-TfR$^E$, and all results presented in FIG. 2C. FIG. 2D is a model illustrating the inverse relationship between affinity and brain uptake. FIG. 2E is a comparison of immunohistochemical staining of brain sections after IV injection with either the high affinity anti-TfR$^A$ or lower affinity anti-TfR$^{B,C,D}$ antibodies showing differences in antibody distribution (staining in left panels is for anti-TfR alone) and extent of co-localization with NeuN (staining in right panels is for both anti-TfR and NeuN). Scale bar=50 µm. FIG. 2F is a representative high magnification image of anti-TfR$^D$ localizaton in neurons (as indicated by NeuN staining); this data shows that anti-TfR$^D$ and NeuN colocalize and thus that anti-TfR$^D$ traverses the BBB and interacts with neurons, whereas anti-TfR$^A$ mainly localizes to the vasculature as opposed to neurons. Scale bar=20 µm.

FIGS. 3A-G show that a bispecific anti-TfR/BACE1 antibody inhibits Aβ in vitro and accumulates in the brain. FIG. 3A is a schematic model of a bispecific antibody which was engineered to bind both TfR and β-secretase (BACE1). FIG. 3B shows binding affinity for TfR of the parental anti-TfR$^A$ and anti-TfR$^A$/BACE1 as measured by the anti-TfR competition ELISA assay described above for FIG. 2A. FIG. 3C shows quantification of Aβ levels produced by HEK293 cells stably expressing APP after treatment with anti-TfR$^A$/BACE1, anti-BACE1, and control IgG in a cell-based assay. The ability of the antibodies to inhibit Aβ1-40 production in HEK293 cells stably expressing wild-type human amyloid precursor protein was assessed as follows. HEK293-APPWT cells were seeded overnight at a density of 3×10$^4$ cells/well in a 96-well plate. 50 µl of fresh media (DMEM+10% FBS) containing an anti-BACE1 antibody or a control IgG1 antibody was incubated with the cells for 24 hours at 37° C. The cellular media was harvested and assayed for the presence of Aβ1-40 using a Aβ1-40 HTRF® assay (CisBio) according to the manufacturer's instructions. Aβ1-40 values were normalized for cell viability, as determined using the CellTiter-Glo Luminescent Cell Viability Assay (Promega). Experiments were performed at least three times, and each point in each experiment was repeated in duplicate. FIG. 3D depicts quantification of mean brain uptake after trace doses of [$^{125}$I]-labeled antibody 30 min., 6, 24, and 48 hours after IV-injection in mice (n=4). FIG. 3E shows quantification of mean antibody uptake in brain and in FIG. 3F average brain to serum ratio at 1, 12, 24, and 48 hours after a 20 mg/kg IV injection of antibody in mice (n=10). The experiments in FIGS. 3E and 3F was performed using the same protocol as the experiment described with regard to FIG. 1B. FIG. 3G shows immunohistochemical staining of brain sections from mice 24 hours after IV injection with either anti-TfR/BACE1 (left panels) or control IgG (right panels). Co-localization of antibody with NeuN is observed after anti-TfR$^A$/BACE1 treatment (NeuN neuronal staining coincides with pervasive antibody staining) but absent in control IgG treated mice (only the NeuN neuronal staining pattern is observed, no antibody staining).

FIGS. 4A-D show quantification of brain (A,B) and plasma (C,D) Aβ$_{1-40}$ levels after a 25 mg/kg or 50 mg/kg IV-injection of control IgG, anti-BACE1, or anti-TfR/BACE1. Briefly, for Abeta1-40 measurements, hemi-brains were homogenized in 5M guanidine hydrochloride buffer and samples rotated for 3 hours at room temperature prior to dilution (1:10) in 0.25% casein, 5 mM EDTA (pH 8.0) in PBS containing freshly added aprotinin (20 mg/mL) and leupeptin (10 mg/ml). Diluted homogenates were centrifuged at 14,000 rpm for 20 min. and supernates were isolated for Abeta1-40 measurement. For antibody concentration measurements, the corresponding hemi-brain from each mouse was homogenized in 1% NP-40 as described above. Whole blood was collected in EDTA microtainer tubes (BD Diagnostics) prior to perfusion, centrifuged at 5,000×g for 15 minutes and the supernatant was isolated for measuring plasma mouse Abeta 1-40 and anti-TfR/BACE1 concentrations. The concentrations of total mouse Abeta1-40 in plasma and brain were determined using a sandwich ELISA following similar procedures described above. Rabbit polyclonal antibody specific for the C-terminus of Abeta1-40 (Millipore, Bedford Mass.) was coated onto plates, and biotinylated anti-mouse Abeta monoclonal antibody M3.2 (Covance, Dedham Mass.) was used for detection. The assay had lower limit of quantification values of 1.96 pg/ml in plasma and 39.1 pg/g in brain. Statistical analysis of differences between experimental groups was performed using a two-tailed unpaired t-test. * represent significance compared to control IgG, while # represent significance compared to anti-BACE1. * p<0.05,  p<0.01, * p<0.001; n=10 for all groups. FIG. 4E shows mean Aβ$_{1-40}$ reduction from data in (A-D) calculated as a percentage of Aβ$_{1-40}$ levels relative to control IgG-injected mice.

FIGS. 5A-B depict the light and heavy chain amino acid sequences of anti-BACE1 clone YW412.8 obtained from a naïve sort of the natural diversity phage display library and affinity-matured forms of YW412.8. FIG. 5A depicts the variable light (VL) sequence alignments (SEQ ID NOs. 1-6). FIG. 5B depicts the variable heavy (VH) sequence alignments (SEQ ID Nos. 7-8). In both figures, the HVR sequences for each clone are indicated by the boxed regions, with the first box indicating HVR-L1 (FIG. 5A) or HVR-H1 (FIG. 5B), the second box indicating HVR-L2 (FIG. 5A) or HVR-H2 (FIG. 5B), and the third box indicating HVR-L3 (FIG. 5A) or HVR-H3 (FIG. 5B).

FIGS. 6A-B depict the light and heavy chain amino acid sequences of clone Fab 12 obtained from a naïve sort of a synthetic diversity phage display library and affinity-matured forms of Fab 12. FIG. 6A depicts the light chain sequence alignments (SEQ ID NOs. 9-12). FIG. 6B depicts the heavy chain sequence alignments (SEQ ID NO. 13). In both figures, the HVR sequences for each clone are indicated by the boxed regions, with the first box indicating HVR-L1 (FIG. 6A) or HVR-H1 (FIG. 6B), the second box indicating HVR-L2 (FIG. 6A) or HVR-H2 (FIG. 6B), and the third box indicating HVR-L3 (FIG. 6A) or HVR-H3 (FIG. 6B).

FIGS. 7A-B depict the heavy chain (FIG. 7A; SEQ ID NO. 14) and light chain (FIG. 7B; SEQ ID NO. 15) of an exemplary anti-Abeta antibody.

FIG. 9A depicts the results of an anti-TfR competition ELISA assay using anti-TfR$^{A,D,E}$/BACE1, following the same assay procedure as that described in FIG. 2A. The IC50 values determined from this data are shown in Table 3. FIGS. 9B and 9D quantitate the amount of observed antibody (9B) and the amount of Abeta1-40 (9D) observed in the plasma at 1, 2, 4, 6, 8 and 10 days after a 50 mg/kg IV injection of antibodies in mice (n=6). FIG. 9C depicts quantification of mean brain uptake and FIG. 9E depicts the amount of Abeta1-40 observed in the brains of those same treated mice at 1, 2, 4, 6, 8 and 10 days after treatment. Six to eight week-old wild type female C57B/6 mice were used for all studies. Mice were intravenously injected with 50 mg/kg anti-TfR/BACE1 variants, control IgG, or anti-BACE1. After the indicated time, mice were perfused with D-PBS, and brain and plasma antibody concentration for each animal was measured as described above. The assay was performed as described in the FIG. 4 description.

FIGS. 10A and 11A depict quantification of the amount of observed antibody in the plasma 1 day after a 50 mg/kg i.p. injection of antibodies in mice (n=4-6). FIGS. 10B and 11B quantitate mean brain uptake in the same treated mice.

DETAILED DESCRIPTION OF EMBODIMENTS OF THE INVENTION

I. Definitions

Figure 1A:
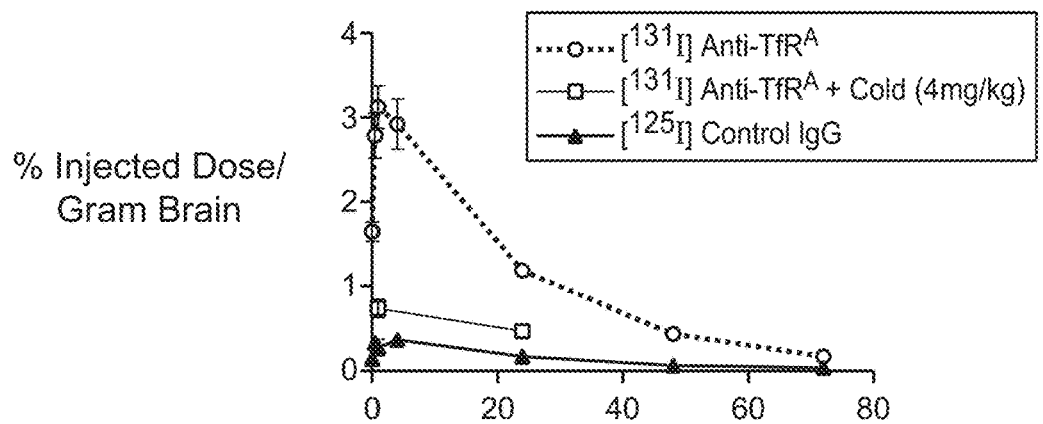
FIGS. 1A-E depict significant brain vascular uptake of systemically administered anti-TfR antibody.

The "blood-brain barrier" or "BBB" refers to the physiological barrier between the peripheral circulation and the brain and spinal cord which is formed by tight junctions within the brain capillary endothelial plasma membranes, creating a tight barrier that restricts the transport of molecules into the brain, even very small molecules such as urea (60 Daltons). The blood-brain barrier within the brain, the blood-spinal cord barrier within the spinal cord, and the blood-retinal barrier within the retina are contiguous capillary barriers within the CNS, and are herein collectively referred to a the blood-brain barrier or BBB. The BBB also encompasses the blood-CSF barrier (choroid plexus) where the barrier is comprised of ependymal cells rather than capillary endothelial cells.

The "central nervous system" or "CNS" refers to the complex of nerve tissues that control bodily function, and includes the brain and spinal cord.

A "blood-brain barrier receptor" (abbreviated "BBB-R" herein) is a transmembrane receptor protein expressed on brain endothelial cells which is capable of transporting molecules across the blood-brain barrier. Examples of BBB-R herein include: transferrin receptor (TfR), insulin receptor, insulin-like growth factor receptor (IGF-R), low density lipoprotein receptors including without limitation low density lipoprotein receptor-related protein 1 (LRP1) and low density lipoprotein receptor-related protein 8 (LRP8), and heparin-binding epidermal growth factor-like growth factor (HB-EGF). An exemplary BBB-R herein is transferrin receptor (TfR).

The "transferrin receptor" ("TfR") is a transmembrane glycoprotein (with a molecular weight of about 180,000) composed of two disulphide-bonded sub-units (each of apparent molecular weight of about 90,000) involved in iron uptake in vertebrates. In one embodiment, the TfR herein is human TfR comprising the amino acid sequence as in Schneider et al. *Nature* 311: 675-678 (1984), for example.

A "neurological disorder" as used herein refers to a disease or disorder which affects the CNS and/or which has an etiology in the CNS. Exemplary CNS diseases or disorders include, but are not limited to, neuropathy, amyloidosis, cancer, an ocular disease or disorder, viral or microbial infection, inflammation, ischemia, neurodegenerative disease, seizure, behavioral disorders, and a lysosomal storage disease. For the purposes of this application, the CNS will be understood to include the eye, which is normally sequestered from the rest of the body by the blood-retina barrier. Specific examples of neurological disorders include, but are not limited to, neurodegenerative diseases (including, but not limited to, Lewy body disease, postpoliomyelitis syndrome, Shy-Draeger syndrome, olivopontocerebellar atrophy, Parkinson's disease, multiple system atrophy, striatonigral degeneration, tauopathies (including, but not limited to, Alzheimer disease and supranuclear palsy), prion diseases (including, but not limited to, bovine spongiform encephalopathy, scrapie, Creutzfeldt-Jakob syndrome, kuru, Gerstmann-Straussler-Scheinker disease, chronic wasting disease, and fatal familial insomnia), bulbar palsy, motor neuron disease, and nervous system heterodegenerative disorders (including, but not limited to, Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome), dementia (including, but not limited to, Pick's disease, and spinocerebellar ataxia), cancer (e.g. of the CNS and/or brain, including brain metastases resulting from cancer elsewhere in the body).

A "neurological disorder drug" is a drug or therapeutic agent that treats one or more neurological disorder(s). Neurological disorder drugs of the invention include, but are not limited to, antibodies, peptides, proteins, natural ligands of one or more CNS target(s), modified versions of natural ligands of one or more CNS target(s), aptamers, inhibitory nucleic acids (i.e., small inhibitory RNAs (siRNA) and short hairpin RNAs (shRNA)), ribozymes, and small molecules, or active fragments of any of the foregoing. Exemplary neurological disorder drugs of the invention are described herein and include, but are not limited to: antibodies, aptamers, proteins, peptides, inhibitory nucleic acids and small molecules and active fragments of any of the foregoing that either are themselves or specifically recognize and/or act upon (i.e., inhibit, activate, or detect) a CNS antigen or target molecule such as, but not limited to, amyloid precursor protein or portions thereof, amyloid beta, beta-secretase, gamma-secretase, tau, alpha-synuclein, parkin, huntingtin, DR6, presenilin, ApoE, glioma or other CNS cancer markers, and neurotrophins. Non-limiting examples of neurological disorder drugs and disorders they may be used to treat are provided in the following Table 1:

TABLE 1

Non-limiting examples of neurological disorder drugs and the corresponding disorders they may be used to treat

| Drug | Neurological disorder |
| --- | --- |
| Anti-BACE1 Antibody | Alzheimer's, acute and chronic brain injury, stroke |
| Anti-Abeta Antibody | Alzheimer's disease |
| Neurotrophin | Stroke, acute brain injury, spinal cord injury |
| Brain-derived neurotrophic factor (BDNF), Fibroblast growth factor 2 (FGF-2) | Chronic brain injury (Neurogenesis) |
| Anti-Epidermal Growth Factor Receptor (EGFR)-antibody | Brain cancer |
| Glial cell-line derived neural factor (GDNF) | Parkinson's disease |
| Brain-derived neurotrophic factor (BDNF) | Amyotrophic lateral sclerosis, depression |
| Lysosomal enzyme | Lysosomal storage disorders of the brain |
| Ciliary neurotrophic factor (CNTF) | Amyotrophic lateral sclerosis |
| Neuregulin-1 | Schizophrenia |
| Anti-HER2 antibody (e.g. trastuzumab) | Brain metastasis from HER2-positive cancer |

An "imaging agent" is a compound that has one or more properties that permit its presence and/or location to be detected directly or indirectly. Examples of such imaging agents include proteins and small molecule compounds incorporating a labeled moiety that permits detection.

A "CNS antigen" or "brain antigen" is an antigen expressed in the CNS, including the brain, which can be targeted with an antibody or small molecule. Examples of such antigens include, without limitation: beta-secretase 1 (BACE1), amyloid beta (Abeta), epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), and caspase 6. In one embodiment, the antigen is BACE1.

The term "BACE1," as used herein, refers to any native beta-secretase 1 (also called β-site amyloid precursor protein cleaving enzyme 1, membrane-associated aspartic protease 2, memapsin 2, aspartyl protease 2 or Asp2) from any vertebrate source, including mammals such as primates (e.g. humans) and rodents (e.g., mice and rats), unless otherwise indicated. The term encompasses "full-length," unprocessed BACE1 as well as any form of BACE1 which results from processing in the cell. The term also encompasses naturally occurring variants of BACE1, e.g., splice variants or allelic variants. The amino acid sequence of an exemplary BACE1 polypeptide is the sequence for human BACE1, isoform A as reported in Vassar et al., Science 286:735-741 (1999), which is incorporated herein by reference in its entirety. Several other isoforms of human BACE1 exist including isoforms B, C and D. See UniProtKB/Swiss-Prot Entry P56817, which is incorporated herein by reference in its entirety.

The terms "anti-beta-secretase antibody", "anti-BACE1 antibody", "an antibody that binds to beta-secretase" and "an antibody that binds to BACE1" refer to an antibody that is capable of binding BACE1 with sufficient affinity such that the antibody is useful as a diagnostic and/or therapeutic agent in targeting BACE1. In one embodiment, the extent of binding of an anti-BACE1 antibody to an unrelated, non-BACE1 protein is less than about 10% of the binding of the antibody to BACE1 as measured, e.g., by a radioimmunoassay (MA). In certain embodiments, an antibody that binds to BACE1 has a dissociation constant (Kd) of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M). In certain embodiments, an anti-BACE1 antibody binds to an epitope of BACE1 that is conserved among BACE1 from different species and isoforms. In one embodiment, an antibody is provided that binds to the epitope on BACE1 bound by anti-BACE1 antibody YW412.8.31. In other embodiments, an antibody is provided that binds to an exosite within BACE1 located in the catalytic domain of BACE1. In one embodiment an antibody is provided that competes with the peptides identified in Kornacker et al., Biochem. 44:11567-11573 (2005), which is incorporated herein by reference in its entirety, (i.e., Peptides 1, 2, 3, 1-11, 1-10, 1-9, 1-8, 1-7, 1-6, 2-12, 3-12, 4-12, 5-12, 6-12, 7-12, 8-12, 9-12, 10-12, 4, 5, 6, 5-10, 5-9, scrambled, YSA, P6A, Y7A, F8A, I9A, P10A and L11A) for binding to BACE1. Exemplary BACE1 antibody sequences are depicted in FIGS. 5A-B and FIGS. 6A-B. One exemplary antibody herein comprises the variable domains of the antibody YW412.8.31 (e.g. as in FIGS. 5A-B).

A "native sequence" protein herein refers to a protein comprising the amino acid sequence of a protein found in nature, including naturally occurring variants of the protein. The term as used herein includes the protein as isolated from a natural source thereof or as recombinantly produced.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

"Antibody fragments" herein comprise a portion of an intact antibody which retains the ability to bind antigen. Examples of antibody fragments include Fab, Fab', F(ab')$_2$, and Fv fragments; diabodies; linear antibodies; single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example. Specific examples of monoclonal antibodies herein include chimeric antibodies, humanized antibodies, and human antibodies, including antigen-binding fragments thereof.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992).

A "human antibody" herein is one comprising an amino acid sequence structure that corresponds with the amino acid sequence structure of an antibody obtainable from a human B-cell, and includes antigen-binding fragments of human antibodies. Such antibodies can be identified or made by a variety of techniques, including, but not limited to: production by transgenic animals (e.g., mice) that are capable, upon immunization, of producing human antibodies in the absence of endogenous immunoglobulin production (see, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and U.S. Pat. Nos. 5,591,669, 5,589,369 and 5,545,807)); selection from phage display libraries expressing human antibodies or human antibody fragments (see, for example, McCafferty et al., *Nature* 348:552-553 (1990); Johnson et al., *Current Opinion in Structural Biology* 3:564-571 (1993); Clackson et al., *Nature*, 352:624-628 (1991); Marks et al., *J. Mol. Biol.* 222:581-597 (1991); Griffith et al., *EMBO J.* 12:725-734 (1993); U.S. Pat. Nos. 5,565,332 and 5,573,905); generation via in vitro activated B cells (see U.S. Pat. Nos. 5,567,610 and 5,229,275); and isolation from human antibody producing hybridomas.

A "multispecific antibody" herein is an antibody having binding specificities for at least two different epitopes. Exemplary multispecific antibodies may bind both a BBB-R and a brain antigen. Multispecific antibodies can be prepared as full-length antibodies or antibody fragments (e.g. F(ab')$_2$ bispecific antibodies). Engineered antibodies with two, three or more (e.g. four) functional antigen binding sites are also contemplated (see, e.g., US Appln No. US 2002/0004587 A1, Miller et al.). Multispecific antibodies can be prepared as full length antibodies or antibody fragments.

Antibodies herein include "amino acid sequence variants" with altered antigen-binding or biological activity. Examples of such amino acid alterations include antibodies with enhanced affinity for antigen (e.g. "affinity matured" antibodies), and antibodies with altered Fc region, if present, e.g. with altered (increased or diminished) antibody dependent cellular cytotoxicity (ADCC) and/or complement dependent cytotoxicity (CDC) (see, for example, WO 00/42072, Presta, L. and WO 99/51642, Iduosogie et al.); and/or increased or diminished serum half-life (see, for example, WO00/42072, Presta, L.).

An "affinity modified variant" has one or more substituted hypervariable region or framework residues of a parent antibody (e.g. of a parent chimeric, humanized, or human antibody) that alter (increase or reduce) affinity. In one embodiment, the resulting variant(s) selected for further development will have reduced affinity for the BBB-R according to the present invention. A convenient way for generating such substitutional variants uses phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity). In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and its target. Such contact residues and neighboring residues are candidates for substitution according to the techniques elaborated herein. Once such variants are generated, the panel of variants is subjected to screening and antibodies with altered affinity may be selected for further development.

The antibody herein may be conjugated with a "heterologous molecule" for example to increase half-life or stability or otherwise improve the antibody. For example, the antibody may be linked to one of a variety of non-proteinaceous polymers, e.g., polyethylene glycol (PEG), polypropylene glycol, polyoxyalkylenes, or copolymers of polyethylene glycol and polypropylene glycol. Antibody fragments, such as Fab', linked to one or more PEG molecules are an exemplary embodiment of the invention.

The antibody herein may be a "glycosylation variant" such that any carbohydrate attached to the Fc region, if present, is altered. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) describing antibodies with modified glycosylation.

The term "hypervariable region" when used herein refers to the amino acid residues of an antibody that are responsible for antigen binding. The hypervariable region comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework" or "FR" residues are those variable domain residues other than the hypervariable region residues as herein defined.

A "full length antibody" is one which comprises an antigen-binding variable region as well as a light chain constant domain (CL) and heavy chain constant domains, CH1, CH2 and CH3. The constant domains may be native sequence constant domains (e.g. human native sequence constant domains) or amino acid sequence variants thereof.

A "naked antibody" is an antibody (as herein defined) that is not conjugated to a heterologous molecule, such as a cytotoxic moiety, polymer, or radiolabel.

Antibody "effector functions" refer to those biological activities attributable to the Fc region (a native sequence Fc region or amino acid sequence variant Fc region) of an antibody. Examples of antibody effector functions include C1q binding, complement dependent cytotoxicity (CDC), Fc receptor binding, antibody-dependent cell-mediated cytotoxicity (ADCC), etc. In one embodiment, the antibody herein essentially lacks effector function.

Depending on the amino acid sequence of the constant domain of their heavy chains, full length antibodies can be assigned to different "classes". There are five major classes of full length antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called alpha, delta, epsilon, gamma, and mu, respectively. The subunit structures and three-dimensional configurations of different classes of immunoglobulins are well known.

The term "recombinant antibody", as used herein, refers to an antibody (e.g. a chimeric, humanized, or human antibody or antigen-binding fragment thereof) that is expressed by a recombinant host cell comprising nucleic acid encoding the antibody. Examples of "host cells" for producing recombinant antibodies include: (1) mammalian cells, for example, Chinese Hamster Ovary (CHO), COS, myeloma cells (including Y0 and NS0 cells), baby hamster kidney (BHK), Hela and Vero cells; (2) insect cells, for example, sf9, sf21 and Tn5; (3) plant cells, for example plants belonging to the genus *Nicotiana* (e.g. *Nicotiana tabacum*); (4) yeast cells, for example, those belonging to the genus *Saccharomyces* (e.g. *Saccharomyces cerevisiae*) or the genus *Aspergillus* (e.g. *Aspergillus niger*); (5) bacterial cells, for example *Escherichia. coli* cells or *Bacillus subtilis* cells, etc.

As used herein, "specifically binding" or "binds specifically to" refers to an antibody selectively or preferentially binding to an antigen. The binding affinity is generally determined using a standard assay, such as Scatchard analysis, or surface plasmon resonance technique (e.g. using BIACORE®).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. In one embodiment, an anti-BACE1 antibody binds to the BACE1 epitope bound by YW412.8.31.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

An "immunoconjugate" is an antibody conjugated to one or more heterologous molecule(s), including but not limited to a label or cytotoxic agent. Optionally such conjugation is via a linker.

A "linker" as used herein is a structure that covalently or non-covalently connects the anti-BBB-R antibody to heterologous molecule. In certain embodiments, a linker is a peptide. In other embodiments, a linker is a chemical linker.

A "label" is a marker coupled with the antibody herein and used for detection or imaging. Examples of such labels include: radiolabel, a fluorophore, a chromophore, or an affinity tag. In one embodiment, the label is a radiolabel used for medical imaging, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese, iron, etc.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

The term "package insert" is used to refer to instructions customarily included in commercial packages of therapeutic products, that contain information about the indications, usage, dosage, administration, combination therapy, contraindications and/or warnings concerning the use of such therapeutic products.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject., A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

II. Compositions and Methods

II. Production of Anti-BBB-R Antibodies and Conjugates Thereof

The methods and articles of manufacture of the present invention use, or incorporate, an antibody that binds to BBB-R. The BBB-R antigen to be used for production of, or screening for, antibodies may be, e.g., a soluble form of or a portion thereof (e.g. the extracellular domain), containing the desired epitope. Alternatively, or additionally, cells expressing BBB-R at their cell surface can be used to generate, or screen for, antibodies. Other forms of BBB-R useful for generating antibodies will be apparent to those skilled in the art. Examples of BBB-Rs herein include transferrin receptor (TfR), insulin receptor, insulin-like growth factor receptor (IGF-R), low density lipoprotein receptor-related protein 1 (LRP1) and LRP8 etc, and heparin-binding epidermal growth factor-like growth factor (HB-EGF).

According to the present invention, a "low affinity" anti-BBB-R (e.g. anti-TfR) antibody is selected based on the data herein demonstrating that such antibodies display improved CNS (for example, brain) uptake. In order to identify such low affinity antibodies, various assays for measuring antibody affinity are available including, without limitation: Scatchard assay and surface plasmon resonance technique (e.g. using BIACORE®). According to one embodiment of the invention, the antibody has an affinity for the BBB-R antigen (e.g. for TfR) from about 5 nM, or from about 20 nM, or from about 100 nM, to about 10 µM, or to about 1 µM, or to about 500 nM. Thus, the affinity may be in the range from about 5 nM to about 10 µM, or in the range from about 20 nM to about 1 µM, or in the range from about 100 nM to about 500 nM, e.g. as measured by Scatchard analysis or BIACORE®.

Thus, the invention provides a method of making an antibody useful for transporting a neurological disorder drug across the blood-brain barrier comprising selecting an antibody from a panel of antibodies against a blood-brain barrier receptor (BBB-R) because it has an affinity for the BBB-R which is in the range from about 5 nM, or from about 20 nM, or from about 100 nM, to about 10 µM, or to about 1 µM, or to about 500 mM. Thus, the affinity may be in the range from about 5 nM to about 10 µM or in the range from about 20 nM to about 1 µM, or in the range from about 100 nM to about 500 nM, e.g. as measured by Scatchard analysis or BIACORE®. As will be understood by one of ordinary skill in the art, conjugating a heterologous molecule/compound to an antibody will often decrease the affinity of the antibody for its target due, e.g., to steric hindrance or even to elimination of one binding arm if the antibody is made multispecific with one or more arms binding to a different antigen than the antibody's original target. In one embodiment, a low affinity antibody of the invention specific for TfR conjugated to BACE1 had a Kd for TfR as measured by BIACORE of about 30 nM. In another embodiment, a low affinity antibody of the invention specific for TfR conjugated to BACE1 had a Kd for TfR as measured by BIACORE of about 600 nM.

One exemplary assay for evaluating antibody affinity is by Scatchard analysis. For example, the anti-BBB-R antibody of interest can be iodinated using the lactoperoxidase method (Bennett and Horuk, *Methods in Enzymology* 288 pg. 134-148 (1997)). A radiolabeled anti-BBB-R antibody is purified from free $^{125}$I-Na by gel filtration using a NAP-5 column and its specific activity measured. Competition reaction mixtures of 50 µL containing a fixed concentration of iodinated antibody and decreasing concentrations of serially diluted unlabeled antibody are placed into 96-well plates. Cells transiently expressing BBB-R are cultured in growth media, consisting of Dulbecco's modified eagle's medium (DMEM) (Genentech) supplemented with 10% FBS, 2 mM L-glutamine and 1× penicillin-streptomycin at 37° C. in 5% $CO_2$. Cells are detached from the dishes using Sigma Cell Dissociation Solution and washed with binding buffer (DMEM with 1% bovine serum albumin, 50 mM HEPES, pH 7.2, and 0.2% sodium azide). The washed cells are added at an approximate density of 200,000 cells in 0.2 mL of binding buffer to the 96-well plates containing the 50-µL competition reaction mixtures. The final concentration of the unlabeled antibody in the competition reaction with cells is varied, starting at 1000 nM and then decreasing by 1:2 fold dilution for 10 concentrations and including a zero-added, buffer-only sample. Competition reactions with cells for each concentration of unlabeled antibody are assayed in triplicate. Competition reactions with cells are incubated for 2 hours at room temperature. After the 2-hour incubation, the competition reactions are transferred to a filter plate and washed four times with binding buffer to separate free from bound iodinated antibody. The filters are counted by gamma counter and the binding data are evaluated using the fitting algorithm of Munson and Rodbard (1980) to determine the binding affinity of the antibody.

An exemplary scatchard analysis using the compositions of the invention may be performed as follows. Anti-TFR$^A$ was iodinated using the lactoperoxidase method (Bennett and Horuk, *Methods in Enzymology* 288 pg. 134-148 (1997)). Radiolabeled anti-TFR$^A$ was purified from free $^{125}$I-Na by gel filtration using a NAP-5 column; purified anti-TFR$^A$ had a specific activity of 19.82 µCi/µg. Competition reaction mixtures of 50 µL containing a fixed concentration of iodinated antibody and decreasing concentrations of serially diluted unlabeled antibody were placed into 96-well plates. The 293 cells transiently expressing murine TfR were cultured in growth media, consisting of Dulbecco's modified eagle's medium (DMEM) (Genentech) supplemented with 10% FBS, 2 mM L-glutamine and 1× penicillin-streptomycin at 37° C. in 5% $CO_2$. Cells were detached from the dishes using Sigma Cell Dissociation Solution and washed with binding buffer (DMEM with 1% bovine serum albumin, 50 mM HEPES, pH 7.2, and 0.2% sodium azide). The washed cells were added at an approximate density of 200,000 cells in 0.2 mL of binding buffer to the 96-well plates containing the 50-µL competition reaction mixtures. The final concentration of the iodinated antibody in each competition reaction with cells was 100 pM (134, 000 cpm per 0.25 mL). The final concentration of the unlabeled antibody in the competition reaction with cells varied, starting at 1000 nM and then decreasing by 1:2 fold dilution for 10 concentrations and including a zero-added, buffer-only sample. Competition reactions with cells for each concentration of unlabeled antibody were assayed in triplicate. Competition reactions with cells were incubated for 2 hours at room temperature. After the 2-hour incubation, the competition reactions were transferred to a Millipore Multiscreen filter plate and washed four times with binding buffer to separate free from bound iodinated antibody. The filters were counted on a Wallac Wizard 1470 gamma counter (PerkinElmer Life and Analytical Sciences; Waltham, Mass.). The binding data were evaluated using New Ligand software (Genentech), which uses the fitting algorithm of Munson and Rodbard (1980) to determine the binding affinity of the antibody.

An exemplary BIACORE® analysis using the compositions of the invention may be performed as follows. Kd was measured using surface plasmon resonance assays using a BIACORE®-2000 (BIAcore, Inc., Piscataway, N.J.) at 25° C. using anti-human Fc kit (BiAcore Inc., Piscataway, N.J.). Briefly, carboxymethylated dextran biosensor chips (CM5, BIACORE, Inc.) were activated with N-ethyl-N'-(3-dimethylaminopropyl)-carbodiimide hydrochloride (EDC) and N-hydroxysuccinimide (NETS) according to the supplier's instructions. Anti-human Fc antibody was diluted with 10 mM sodium acetate, pH 4.0, to 50 µg/ml before injection at a flow rate of 5 µl/minute to achieve approximately 10000 response units (RU) of coupled protein. Following the injection of antibody, 1 M ethanolamine was injected to block unreacted groups. For kinetics measurements, anti-TfR antibody variants were injected in HBS-P to reach about 220 RU, then two-fold serial dilutions of MuTfR-His (0.61 nM to 157 nM) were injected in HBS-P at 25° C. at a flow rate of approximately 30 µl/min. Association rates (kon) and dissociation rates (koff) were calculated using a simple one-to-one Langmuir binding model (BIACORE® Evaluation Software version 3.2) by simultaneously fitting the association and dissociation sensorgrams. The equilibrium dissociation constant (Kd) was calculated as the ratio koff/kon. See, e.g., Chen et al., *J. Mol. Biol.* 293:865-881 (1999)

According to another embodiment, Kd is measured using surface plasmon resonance assays with a BIACORE®-2000 device (BIAcore, Inc., Piscataway, N.J.) at 25° C. using anti-human Fc kit (BiAcore Inc., Piscataway, N.J.). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Anti-human Fc antibody is diluted with 10 mM sodium acetate, pH 4.0, to 50 µg/ml before injection at a flow rate of 5 µl/minute to achieve approximately 10000 response units (RU) of coupled protein. Following the injection of antibody, 1 M ethanolamine is injected to block unreacted groups. For kinetics measurements, anti-BBB-R antibody variants are injected in HBS-P to reach about 220 RU, then two-fold serial dilutions of BBB-R-His (0.61 nM to 157 nM) are injected in HBS-P at 25° C. at a flow rate of approximately 30 µl/min. Association rates (kon) and dissociation rates (koff) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio koff/kon. See, e.g., Chen et al., *J. Mol. Biol.* 293:865-881 (1999).

A surrogate measurement for the affinity of one or more antibodies for the BBB-R is its half maximal inhibitory concentration (IC50), a measure of how much of the antibody is needed to inhibit the binding of a known BBB-R ligand to the BBB-R by 50%. Several methods of determining the IC50 for a given compound are art-known; a common approach is to perform a competition binding assay, such as that described herein in the examples, i.e. with regard to FIG. 2A. In general, a high IC50 indicates that more of the antibody is required to inhibit binding of the known ligand, and thus that the antibody's affinity for that ligand is relatively low. Conversely, a low IC50 indicates that less of the antibody is required to inhibit binding of the known ligand, and thus that the antibody's affinity for that ligand is relatively high.

An exemplary competitive ELISA assay to measure IC50 is one in which increasing concentrations of anti-TfR or anti-TfR/brain antigen (i.e., anti-TfR/BACE1, anti-TfR/Abeta and the like) variant antibodies are used to compete against biotinylated TfR$^A$ for binding to TfR. The anti-TfR competition ELISA was performed in Maxisorp plates (Neptune, N.J.) coated with 2.5 µg/ml of purified murine TfR extracellular domain in PBS at 4° C. overnight. Plates were washed with PBS/0.05% Tween 20 and blocked using Superblock blocking buffer in PBS (Thermo Scientific, Hudson, N.H.). A titration of each individual anti-TfR or anti-TfR/brain antigen (i.e., anti-TfR/BACE1 or anti-TfR/Abeta) (1:3 serial dilution) was combined with biotinylated anti-TfR$^A$ (0.5 nM final concentration) and added to the plate for 1 hour at room temperature. Plates were washed with PBS/0.05% Tween 20, and HRP-streptavidin (Southern Biotech, Birmingham) was added to the plate and incubated for 1 hour at room temperature. Plates were washed with PBS/0.05% Tween 20, and biotinylated anti-TfR$^A$ bound to the plate was detected using TMB substrate (BioFX Laboratories, Owings Mills).

In one embodiment, the low affinity anti-BBB-R antibody herein is coupled with a label and/or neurological disorder drug or imaging agent in order to more efficiently transport the label and/or drug or imaging agent across the BBB. Such coupling can be achieved by chemical cross-linkers or by generating fusion proteins etc.

Covalent conjugation can either be direct or via a linker. In certain embodiments, direct conjugation is by construction of a protein fusion (i.e., by genetic fusion of the two genes encoding BBB-R antibody and neurological disorder drug and expression as a single protein). In certain embodiments, direct conjugation is by formation of a covalent bond between a reactive group on one of the two portions of the anti-BBB-R antibody and a corresponding group or acceptor on the neurological drug. In certain embodiments, direct conjugation is by modification (i.e., genetic modification) of one of the two molecules to be conjugated to include a reactive group (as nonlimiting examples, a sulfhydryl group or a carboxyl group) that forms a covalent attachment to the other molecule to be conjugated under appropriate conditions. As one nonlimiting example, a molecule (i.e., an amino acid) with a desired reactive group (i.e., a cysteine residue) may be introduced into, e.g., the anti-BBB-R antibody and a disulfide bond formed with the neurological drug. Methods for covalent conjugation of nucleic acids to proteins are also known in the art (i.e., photocrosslinking, see, e.g., Zatsepin et al. *Russ. Chem. Rev.* 74: 77-95 (2005)) Non-covalent conjugation can be by any nonconvalent attachment means, including hydrophobic bonds, ionic bonds, electrostatic interactions, and the like, as will be readily understood by one of ordinary skill in the art. Conjugation may also be performed using a variety of linkers. For example, an anti-BBB-R antibody and a neurological drug may be conjugated using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Peptide linkers, comprised of from one to twenty amino acids joined by peptide bonds, may also be used. In certain such embodiments, the amino acids are selected from the twenty naturally-occurring amino acids. In certain other such embodiments, one or more of the amino acids are selected from glycine, alanine, proline, asparagine, glutamine and lysine. The linker may be a "cleavable linker" facilitating release of the neurological drug upon delivery to the brain. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The invention herein expressly contemplates, but is not limited to, conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A.).

For a neuropathy disorder, a neurological drug may be selected that is an analgesic including, but not limited to, a narcotic/opioid analgesic (i.e., morphine, fentanyl, hydrocodone, meperidine, methadone, oxymorphone, pentazocine, propoxyphene, tramadol, codeine and oxycodone), a non-steroidal anti-inflammatory drug (NSAID) (i.e., ibuprofen, naproxen, diclofenac, diflunisal, etodolac, fenoprofen, flurbiprofen, indomethacin, ketorolac, mefenamic acid, meloxicam, nabumetone, oxaprozin, piroxicam, sulindac, and tolmetin), a corticosteroid (i.e., cortisone, prednisone, prednisolone, dexamethasone, methylprednisolone and triamcinolone), an anti-migraine agent (i.e., sumatriptin, almotriptan, frovatriptan, sumatriptan, rizatriptan, eletriptan, zolmitriptan, dihydroergotamine, eletriptan and ergotamine), acetaminophen, a salicylate (i.e., aspirin, choline salicylate, magnesium salicylate, diflunisal, and salsalate), a anti-convulsant (i.e., carbamazepine, clonazepam, gabapentin, lamotrigine, pregabalin, tiagabine, and topiramate), an anaesthetic (i.e., isoflurane, trichloroethylene, halothane, sevoflurane, benzocaine, chloroprocaine, cocaine, cyclomethycaine, dimethocaine, propoxycaine, procaine, novocaine, proparacaine, tetracaine, articaine, bupivacaine, carticaine, cinchocaine, etidocaine, levobupivacaine, lidocaine, mepivacaine, piperocaine, prilocaine, ropivacaine, trimecaine, saxitoxin and tetrodotoxin), and a cox-2-inhibitor (i.e., celecoxib, rofecoxib, and valdecoxib). For a neuropathy disorder with vertigo involvement, a neurological drug may be selected that is an anti-vertigo agent including, but not limited to, meclizine, diphenhydramine, promethazine and diazepam. For a neuropathy disorder with nausea involvement, a neurological drug may be selected that is an anti-nausea agent including, but not limited to, promethazine, chlorpromazine, prochlorperazine, trimethobenzamide, and metoclopramide. For a neurodegenerative disease, a neurological drug may be selected that is a growth hormone or neurotrophic factor; examples include but are not limited to brain-derived neurotrophic factor (BDNF), nerve growth factor (NGF), neurotrophin-4/5, fibroblast growth factor (FGF)-2 and other FGFs, neurotrophin (NT)-3, erythropoietin (EPO), hepatocyte growth factor (HGF), epidermal growth factor (EGF), transforming growth factor (TGF)-alpha, TGF-beta, vascular endothelial growth factor (VEGF), interleukin-1 receptor antagonist (IL-1ra), ciliary neurotrophic factor (CNTF), glial-derived neurotrophic factor (GDNF), neurturin, platelet-derived growth factor (PDGF), heregulin, neuregulin, artemin, persephin, interleukins, glial cell line derived neurotrophic factor (GFR), granulocyte-colony stimulating factor (CSF), granulocyte-macrophage-CSF, netrins, cardiotrophin-1, hedgehogs, leukemia inhibitory factor (LIF), midkine, pleiotrophin, bone morphogenetic proteins (BMPs), netrins, saposins, semaphorins, and stem cell factor (SCF).

For cancer, a neurological drug may be selected that is a chemotherapeutic agent. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphor-amide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition of chemotherapeutic agents are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

Another group of compounds that may be selected as neurological drugs for cancer treatment or prevention are anti-cancer immunoglobulins (including, but not limited to, trastuzumab, bevacizumab, alemtuxumab, cetuximab, gemtuzumab ozogamicin, ibritumomab tiuxetan, panitumumab and rituximab). In some instances, antibodies in conjunction with a toxic label may be used to target and kill desired cells (i.e., cancer cells), including, but not limited to, tositumomab with a $^{131}$I radiolabel.

For an ocular disease or disorder, a neurological drug may be selected that is an anti-angiogenic ophthalmic agent (i.e., bevacizumab, ranibizumab and pegaptanib), an ophthalmic glaucoma agent (i.e., carbachol, epinephrine, demecarium bromide, apraclonidine, brimonidine, brinzolamide, levobunolol, timolol, betaxolol, dorzolamide, bimatoprost, carteolol, metipranolol, dipivefrin, travoprost and latanoprost), a carbonic anhydrase inhibitor (i.e., methazolamide and acetazolamide), an ophthalmic antihistamine (i.e., naphazoline, phenylephrine and tetrahydrozoline), an ocular lubricant, an ophthalmic steroid (i.e., fluorometholone, prednisolone, loteprednol, dexamethasone, difluprednate, rimexolone, fluocinolone, medrysone and triamcinolone), an ophthalmic anesthetic (i.e., lidocaine, proparacaine and tetracaine), an ophthalmic anti-infective (i.e., levofloxacin, gatifloxacin, ciprofloxacin, moxifloxacin, chloramphenicol, bacitracin/polymyxin b, sulfacetamide, tobramycin, azithromycin, besifloxacin, norfloxacin, sulfisoxazole, gentamicin, idoxuridine, erythromycin, natamycin, gramicidin, neomycin, ofloxacin, trifluridine, ganciclovir, vidarabine), an ophthalmic anti-inflammatory agent (i.e., nepafenac, ketorolac, flurbiprofen, suprofen, cyclosporine, triamcinolone, diclofenac and bromfenac), and an ophthalmic antihistamine or decongestant (i.e., ketotifen, olopatadine, epinastine, naphazoline, cromolyn, tetrahydrozoline, pemirolast, bepotastine, naphazoline, phenylephrine, nedocromil, lodoxamide, phenylephrine, emedastine and azelastine).

For a seizure disorder, a neurological drug may be selected that is an anticonvulsant or antiepileptic including, but not limited to, barbiturate anticonvulsants (i.e., primidone, metharbital, mephobarbital, allobarbital, amobarbital, aprobarbital, alphenal, barbital, brallobarbital and phenobarbital), benzodiazepine anticonvulsants (i.e., diazepam, clonazepam, and lorazepam), carbamate anticonvulsants (i.e. felbamate), carbonic anhydrase inhibitor anticonvulsants (i.e., acetazolamide, topiramate and zonisamide), dibenzazepine anticonvulsants (i.e., rufinamide, carbamazepine, and oxcarbazepine), fatty acid derivative anticonvulsants (i.e., divalproex and valproic acid), gamma-aminobutyric acid analogs (i.e., pregabalin, gabapentin and vigabatrin), gamma-aminobutyric acid reuptake inhibitors (i.e., tiagabine), gamma-aminobutyric acid transaminase inhibitors (i.e., vigabatrin), hydantoin anticonvulsants (i.e. phenytoin, ethotoin, fosphenytoin and mephenytoin), miscellaneous anticonvulsants (i.e., lacosamide and magnesium sulfate), progestins (i.e., progesterone), oxazolidinedione anticonvulsants (i.e., paramethadione and trimethadione), pyrrolidine anticonvulsants (i.e., levetiracetam), succinimide anticonvulsants (i.e., ethosuximide and methsuximide), triazine anticonvulsants (i.e., lamotrigine), and urea anticonvulsants (i.e., phenacemide and pheneturide).

For a lysosomal storage disease, a neurological drug may be selected that is itself or otherwise mimics the activity of the enzyme that is impaired in the disease. Exemplary recombinant enzymes for the treatment of lysosomal storage disorders include, but are not limited to those set forth in e.g., U.S. Patent Application publication no. 2005/0142141 (i.e., alpha-L-iduronidase, iduronate-2-sulphatase, N-sulfatase, alpha-N-acetylglucosaminidase, N-acetyl-galactosamine-6-sulfatase, beta-galactosidase, arylsulphatase B, beta-glucuronidase, acid alpha-glucosidase, glucocerebrosidase, alpha-galactosidase A, hexosaminidase A, acid sphingomyelinase, beta-galactocerebrosidase, beta-galactosidase, arylsulfatase A, acid ceramidase, aspartoacylase, palmitoyl-protein thioesterase 1 and tripeptidyl amino peptidase 1).

For amyloidosis, a neurological drug may be selected that includes, but is not limited to, an antibody or other binding molecule (including, but not limited to a small molecule, a peptide, an aptamer, or other protein binder) that specifically binds to a target selected from: beta secretase, tau, presenilin, amyloid precursor protein or portions thereof, amyloid beta peptide or oligomers or fibrils thereof, death receptor 6 (DR6), receptor for advanced glycation endproducts (RAGE), parkin, and huntingtin; a cholinesterase inhibitor (i.e., galantamine, donepezil, rivastigmine and tacrine); an NMDA receptor antagonist (i.e., memantine), a monoamine depletor (i.e., tetrabenazine); an ergoloid mesylate; an anti-cholinergic antiparkinsonism agent (i.e., procyclidine, diphenhydramine, trihexylphenidyl, benztropine, biperiden and trihexyphenidyl); a dopaminergic antiparkinsonism agent (i.e., entacapone, selegiline, pramipexole, bromocriptine, rotigotine, selegiline, ropinirole, rasagiline, apomorphine, carbidopa, levodopa, pergolide, tolcapone and amantadine); a tetrabenazine; an anti-inflammatory (including, but not limited to, a nonsteroidal anti-inflammatory drug (i.e., indomethicin and other compounds listed above); a hormone (i.e., estrogen, progesterone and leuprolide); a vitamin (i.e., folate and nicotinamide); a dimebolin; a homotaurine (i.e., 3-aminopropanesulfonic acid; 3APS); a serotonin receptor activity modulator (i.e., xaliproden); an, an interferon, and a glucocorticoid.

For a viral or microbial disease, a neurological drug may be selected that includes, but is not limited to, an antiviral compound (including, but not limited to, an adamantane antiviral (i.e., rimantadine and amantadine), an antiviral interferon (i.e., peginterferon alfa-2b), a chemokine receptor antagonist (i.e., maraviroc), an integrase strand transfer inhibitor (i.e., raltegravir), a neuraminidase inhibitor (i.e., oseltamivir and zanamivir), a non-nucleoside reverse transcriptase inhibitor (i.e., efavirenz, etravirine, delavirdine and nevirapine), a nucleoside reverse transcriptase inhibitors (tenofovir, abacavir, lamivudine, zidovudine, stavudine, entecavir, emtricitabine, adefovir, zalcitabine, telbivudine and didanosine), a protease inhibitor (i.e., darunavir, atazanavir, fosamprenavir, tipranavir, ritonavir, nelfinavir, amprenavir, indinavir and saquinavir), a purine nucleoside (i.e., valacyclovir, famciclovir, acyclovir, ribavirin, ganciclovir, valganciclovir and cidofovir), and a miscellaneous antiviral (i.e., enfuvirtide, foscarnet, palivizumab and fomivirsen)), an antibiotic (including, but not limited to, an aminopenicillin (i.e., amoxicillin, ampicillin, oxacillin, nafcillin, cloxacillin, dicloxacillin, flucoxacillin, temocillin, azlocillin, carbenicillin, ticarcillin, mezlocillin, piperacillin and bacampicillin), a cephalosporin (i.e., cefazolin, cephalexin, cephalothin, cefamandole, ceftriaxone, cefotaxime, cefpodoxime, ceftazidime, cefadroxil, cephradine, loracarbef, cefotetan, cefuroxime, cefprozil, cefaclor, and cefoxitin), a carbapenem/penem (i.e., imipenem, meropenem, ertapenem, faropenem and doripenem), a monobactam (i.e., aztreonam, tigemonam, norcardicin A and tabtoxinine-betalactam, a beta-lactamase inhibitor (i.e., clavulanic acid, tazobactam and sulbactam) in conjunction with another beta-lactam antibiotic, an aminoglycoside (i.e., amikacin, gentamicin, kanamycin, neomycin, netilmicin, streptomycin, tobramycin, and paromomycin), an ansamycin (i.e., geldanamycin and herbimycin), a carbacephem (i.e., loracarbef), a glycopeptides (i.e., teicoplanin and vancomycin), a macrolide (i.e., azithromycin, clarithromycin, dirithromycin, erythromycin, roxithromycin, troleandomycin, telithromycin and spectinomycin), a monobactam (i.e., aztreonam), a quinolone (i.e., ciprofloxacin, enoxacin, gatifloxacin, levofloxacin, lomefloxacin, moxifloxacin, norfloxacin, ofloxacin, trovafloxacin, grepafloxacin, sparfloxacin and temafloxacin), a sulfonamide (i.e., mafenide, sulfonamidochrysoidine, sulfacetamide, sulfadiazine, sulfamethizole, sulfanilamide, sulfasalazine, sulfisoxazole, trimethoprim, trimethoprim and sulfamethoxazole), a tetracycline (i.e., tetracycline, demeclocycline, doxycycline, minocycline and oxytetracycline), an antineoplastic or cytotoxic antibiotic (i.e., doxorubicin, mitoxantrone, bleomycin, daunorubicin, dactinomycin, epirubicin, idarubicin, plicamycin, mitomycin, pentostatin and valrubicin) and a miscellaneous antibacterial compound (i.e., bacitracin, colistin and polymyxin B)), an antifungal (i.e., metronidazole, nitazoxanide, tinidazole, chloroquine, iodoquinol and paromomycin), and an antiparasitic (including, but not limited to, quinine, chloroquine, amodiaquine, pyrimethamine, sulphadoxine, proguanil, mefloquine, atovaquone, primaquine, artemesinin, halofantrine, doxycycline, clindamycin, mebendazole, pyrantel pamoate, thiabendazole, diethylcarbamazine, ivermectin, rifampin, amphotericin B, melarsoprol, eformithine and albendazole).

For ischemia, a neurological drug may be selected that includes, but is not limited to, a thrombolytic (i.e., urokinase, alteplase, reteplase and tenecteplase), a platelet aggregation inhibitor (i.e., aspirin, cilostazol, clopidogrel, prasugrel and dipyridamole), a statin (i.e., lovastatin, pravastatin, fluvastatin, rosuvastatin, atorvastatin, simvastatin, cerivastatin and pitavastatin), and a compound to improve blood flow or vascular flexibility, including, e.g., blood pressure medications.

For a behavioral disorder, a neurological drug may be selected from a behavior-modifying compound including, but not limited to, an atypical antipsychotic (i.e., risperidone, olanzapine, apripiprazole, quetiapine, paliperidone, asenapine, clozapine, iloperidone and ziprasidone), a phenothiazine antipsychotic (i.e., prochlorperazine, chlorpromazine, fluphenazine, perphenazine, trifluoperazine, thioridazine and mesoridazine), a thioxanthene (i.e., thiothixene), a miscellaneous antipsychotic (i.e., pimozide, lithium, molindone, haloperidol and loxapine), a selective serotonin reuptake inhibitor (i.e., citalopram, escitalopram, paroxetine, fluoxetine and sertraline), a serotonin-norepinephrine reuptake inhibitor (i.e., duloxetine, venlafaxine, desvenlafaxine, a tricyclic antidepressant (i.e., doxepin, clomipramine, amoxapine, nortriptyline, amitriptyline, trimipramine, imipramine, protriptyline and desipramine), a tetracyclic antidepressant (i.e., mirtazapine and maprotiline), a phenylpiperazine antidepressant (i.e., trazodone and nefazodone), a monoamine oxidase inhibitor (i.e., isocarboxazid, phenelzine, selegiline and tranylcypromine), a benzodiazepine (i.e., alprazolam, estazolam, flurazeptam, clonazepam, lorazepam and diazepam), a norepinephrine-dopamine reuptake inhibitor (i.e., bupropion), a CNS stimulant (i.e., phentermine, diethylpropion, methamphetamine, dextroamphetamine, amphetamine, methylphenidate, dexmethylphenidate, lisdexamfetamine, modafinil, pemoline, phendimetrazine, benzphetamine, phendimetrazine, armodafinil, diethylpropion, caffeine, atomoxetine, doxapram, and mazindol), an anxiolytic/sedative/hypnotic (including, but not limited to, a barbiturate (i.e., secobarbital, phenobarbital and mephobarbital), a benzodiazepine (as described above), and a miscellaneous anxiolytic/sedative/hypnotic (i.e. diphenhydramine, sodium oxybate, zaleplon, hydroxyzine, chloral hydrate, aolpidem, buspirone, doxepin, eszopiclone, ramelteon, meprobamate and ethclorvynol)), a secretin (see, e.g., Ratliff-Schaub et al. *Autism* 9: 256-265 (2005)), an opioid peptide (see, e.g., Cowen et al., *J. Neurochem.* 89:273-285 (2004)), and a neuropeptide (see, e.g., Hethwa et al. *Am. J. Physiol.* 289: E301-305 (2005)).

For CNS inflammation, a neurological drug may be selected that addresses the inflammation itself (i.e., a non-steroidal anti-inflammatory agent such as ibuprofen or naproxen), or one which treats the underlying cause of the inflammation (i.e., an anti-viral or anti-cancer agent).

According to one embodiment of the invention, the "coupling" is achieved by generating a multispecific antibody (e.g. a bispecific antibody). Multispecific antibodies are monoclonal antibodies that have binding specificities for at least two different sites. In one embodiment, the multispecific antibody comprises a first antigen binding site which binds the BBB-R and a second antigen binding site which binds a brain antigen, such as beta-secretase 1 (BACE1) or Abeta, and the other brain antigens disclosed herein.

An exemplary brain antigen bound by such multispecific/bispecific antibody is BACE1, and an exemplary antibody binding thereto is the YW412.8.31 antibody in FIGS. 5*a-b* herein.

In another embodiment, the brain antigen is Abeta, exemplary such antibodies being described in WO2007068412, WO2008011348, WO20080156622, and WO2008156621, expressly incorporated herein by reference, with an exemplary Abeta antibody comprising IgG4 MABT5102A antibody comprising the heavy and light chain amino acid sequences in FIGS. 7*a* and 7*b*, respectively.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies" or "dual-variable domain immunoglobulins" (DVDs) are also included herein (see, e.g. US 2006/0025576A1, and Wu et al. *Nature Biotechnology* (2007)).

The antibody or fragment herein also includes a "Dual Acting FAb" or "DAF" comprising an antigen binding site that binds to the BBB-R (e.g. TfR) as well as the brain antigen (e.g. BACE1) (see, US 2008/0069820, for example).

In one embodiment, the antibody is an antibody fragment, various such fragments being disclosed above.

In another embodiment, the antibody is an intact or full-length antibody. Depending on the amino acid sequence of the constant domain of their heavy chains, intact antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called α, δ, ε, γ, and μ, respectively. The subunit structures and three-dimensional configurations of different classes of immunoglobulins are well known. In one embodiment, the intact antibody lacks effector function.

Techniques for generating antibodies are known and examples provided above in the definitions section of this document. In one embodiment, the antibody is a chimeric, humanized, or human antibody or antigen-binding fragment thereof.

Various techniques are available for determining binding of the antibody to the BBB-R. One such assay is an enzyme linked immunosorbent assay (ELISA) for confirming an ability to bind to human BBB-R (and brain antigen). According to this assay, plates coated with antigen (e.g. recombinant sBBB-R) are incubated with a sample comprising the anti-BBB-R antibody and binding of the antibody to the antigen of interest is determined.

In one aspect, an antibody of the invention is tested for its antigen binding activity, e.g., by known methods such as ELISA, Western blot, etc.

Assays for evaluating uptake of systemically administered antibody and other biological activity of the antibody can be performed as disclosed in the examples or as known for the anti-brain antigen antibody of interest.

Exemplary assays where the multispecific antibody binds BACE1 shall now be described.

Competition assays may be used to identify an antibody that competes with any of the antibodies or Fabs described herein, for example, YW412.8, YW412.8.31, YW412.8.30, YW412.8.2, YW412.8.29, YW412.8.51, Fab12, LC6, LC9, LC10 for binding to BACE1. In certain embodiments, such a competing antibody binds to the same epitope (e.g., a linear or a conformational epitope) that is bound by any of the antibodies or Fabs described herein, for example, YW412.8, YW412.8.31, YW412.8.30, YW412.8.2, YW412.8.29, YW412.8.51, Fab12, LC6, LC9, LC10. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized BACE1 is incubated in a solution comprising a first labeled antibody that binds to BACE1 (e.g., YW412.8, YW412.8.31, YW412.8.30, YW412.8.2, YW412.8.29, YW412.8.51, Fab12, LC6, LC9, LC10) and a second unlabeled antibody that is being tested for its ability to compete with the first antibody for binding to BACE1. The second antibody may be present in a hybridoma supernatant. As a control, immobilized BACE1 is incubated in a solution comprising the first labeled antibody but not the second unlabeled antibody. After incubation under conditions permissive for binding of the first antibody to BACE1, excess unbound antibody is removed, and the amount of label associated with immobilized BACE1 is measured. If the amount of label associated with immobilized BACE1 is substantially reduced in the test sample relative to the control sample, then that indicates that the second antibody is competing with the first antibody for binding to BACE1. See Harlow and Lane (1988) *Antibodies: A Laboratory Manual* ch. 14 (Cold Spring Harbor Laboratory, Cold Spring Harbor, N.Y.).

In one aspect, assays are provided for identifying anti-BACE1 antibodies thereof having biological activity. Biological activity may include, e.g., inhibition of BACE1 aspartyl protease activity. Antibodies having such biological activity in vivo and/or in vitro are also provided, e.g. as evaluated by homogeneous time-resolved fluorescence HTRF assay or a microfluidic capillary electrophoretic (MCE) assay using synthetic substrate peptides, or in vivo in cell lines which express BACE1 substrates such as APP.

The antibody (including the multispecific antibody) herein is optionally recombinantly produced in a host cell transformed with nucleic acid sequences encoding its heavy and light chains (e.g. where the host cell has been transformed by one or more vectors with the nucleic acid therein). The host cell is optionally a mammalian cell, for example a Chinese Hamster Ovary (CHO) cell.

III. Pharmaceutical Formulations

Therapeutic formulations of the antibodies used in accordance with the present invention are prepared for storage by mixing an antibody having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The formulation herein may also contain more than one active compound as necessary, optionally those with complementary activities that do not adversely affect each other. The type and effective amounts of such medicaments depend, for example, on the amount of antibody present in the formulation, and clinical parameters of the subjects. Exemplary such medicaments are discussed below.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid.

The formulations to be used for in vivo administration must be sterile. This is readily accomplished by filtration through sterile filtration membranes.

In one embodiment the formulation is isotonic.

IV. Therapeutic Uses of Anti-BBB-R Antibodies

The anti-BBB-R antibodies (including multispecific antibodies comprising them) may be utilized in a variety of in vivo methods. For example, the invention provides a method of transporting a therapeutic compound across the blood-brain barrier comprising exposing the anti-BBB-R antibody coupled to a therapeutic compound (e.g. a multispecific antibody which binds both the BBB-R and a brain antigen) to the BBB such that the antibody transports the therapeutic compound coupled thereto across the BBB. In another example, the invention provides a method of transporting a neurological disorder drug across the blood-brain barrier comprising exposing the anti-BBB-R antibody coupled to a brain disorder drug (e.g. a multispecific antibody which binds both the BBB-R and a brain antigen) to the BBB such that the antibody transports the neurological disorder drug coupled thereto across the BBB. In one embodiment, the BBB here is in a mammal (e.g. a human), e.g. one which has a neurological disorder, including, without limitation: Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, traumatic brain injury, etc.

In one embodiment, neurological disorder is selected from: a neuropathy, amyloidosis, cancer (e.g. involving the CNS or brain), an ocular disease or disorder, a viral or microbial infection, inflammation (e.g. of the CNS or brain), ischemia, neurodegenerative disease, seizure, behavioral disorder, lysosomal storage disease, etc.

Neuropathy disorders are diseases or abnormalities of the nervous system characterized by inappropriate or uncontrolled nerve signaling or lack thereof, and include, but are not limited to, chronic pain (including nociceptive pain), pain caused by an injury to body tissues, including cancer-related pain, neuropathic pain (pain caused by abnormalities in the nerves, spinal cord, or brain), and psychogenic pain (entirely or mostly related to a psychological disorder), headache, migraine, neuropathy, and symptoms and syndromes often accompanying such neuropathy disorders such as vertigo or nausea.

Amyloidoses are a group of diseases and disorders associated with extracellular proteinaceous deposits in the CNS, including, but not limited to, secondary amyloidosis, age-related amyloidosis, Alzheimer's Disease (AD), mild cognitive impairment (MCI), Lewy body dementia, Down's syndrome, hereditary cerebral hemorrhage with amyloidosis (Dutch type); the Guam Parkinson-Dementia complex, cerebral amyloid angiopathy, Huntington's disease, progressive supranuclear palsy, multiple sclerosis; Creutzfeld Jacob disease, Parkinson's disease, transmissible spongiform encephalopathy, HIV-related dementia, amyotropic lateral sclerosis (ALS), inclusion-body myositis (IBM), and ocular diseases relating to beta-amyloid deposition (i.e., macular degeneration, drusen-related optic neuropathy, and cataract).

Cancers of the CNS are characterized by aberrant proliferation of one or more CNS cell (i.e., a neural cell) and include, but are not limited to, glioma, glioblastoma multiforme, meningioma, astrocytoma, acoustic neuroma, chondroma, oligodendroglioma, medulloblastomas, ganglioglioma, Schwannoma, neurofibroma, neuroblastoma, and extradural, intramedullary or intradural tumors.

Ocular diseases or disorders are diseases or disorders of the eye, which for the purposes herein is considered a CNS organ subject to the BBB. Ocular diseases or disorders include, but are not limited to, disorders of sclera, cornea, iris and ciliary body (i.e., scleritis, keratitis, corneal ulcer, corneal abrasion, snow blindness, arc eye, Thygeson's superficial punctate keratopathy, corneal neovascularisation, Fuchs' dystrophy, keratoconus, keratoconjunctivitis sicca, iritis and uveitis), disorders of the lens (i.e., cataract), disorders of choroid and retina (i.e., retinal detachment, retinoschisis, hypertensive retinopathy, diabetic retinopathy, retinopathy, retinopathy of prematurity, age-related macular degeneration, macular degeneration (wet or dry), epiretinal membrane, retinitis pigmentosa and macular edema), glaucoma, floaters, disorders of optic nerve and visual pathways (i.e., Leber's hereditary optic neuropathy and optic disc drusen), disorders of ocular muscles/binocular movement accommodation/refraction (i.e., strabismus, ophthalmoparesis, progressive external opthalmoplegia, esotropia, exotropia, hypermetropia, myopia, astigmatism, anisometropia, presbyopia and ophthalmoplegia), visual disturbances and blindness (i.e., amblyopia, Lever's congenital amaurosis, scotoma, color blindness, achromatopsia, nyctalopia, blindness, river blindness and micro-opthalmia/coloboma), red eye, Argyll Robertson pupil, keratomycosis, xerophthalmia and andaniridia.

Viral or microbial infections of the CNS include, but are not limited to, infections by viruses (i.e., influenza, HIV, poliovirus, rubella,), bacteria (i.e., *Neisseria* sp., *Streptococcus* sp., *Pseudomonas* sp., *Proteus* sp., *E. coli, S. aureus, Pneumococcus* sp., *Meningococcus* sp., *Haemophilus* sp., and *Mycobacterium tuberculosis*) and other microorganisms such as fungi (i.e., yeast, *Cryptococcus neoformans*), parasites (i.e., toxoplasma *gondii*) or amoebas resulting in CNS pathophysiologies including, but not limited to, meningitis, encephalitis, myelitis, vasculitis and abscess, which can be acute or chronic.

Inflammation of the CNS is inflammation that is caused by an injury to the CNS, which can be a physical injury (i.e., due to accident, surgery, brain trauma, spinal cord injury, concussion) or an injury due to or related to one or more other diseases or disorders of the CNS (i.e., abscess, cancer, viral or microbial infection).

Ischemia of the CNS, as used herein, refers to a group of disorders relating to aberrant blood flow or vascular behavior in the brain or the causes therefor, and includes, but is not limited to: focal brain ischemia, global brain ischemia, stroke (i.e., subarachnoid hemorrhage and intracerebral hemorrhage), and aneurysm.

Neurodegenerative diseases are a group of diseases and disorders associated with neural cell loss of function or death in the CNS, and include, but are not limited to: adrenoleukodystrophy, Alexander's disease, Alper's disease, amyotrophic lateral sclerosis, ataxia telangiectasia, Batten disease, cockayne syndrome, corticobasal degeneration, degeneration caused by or associated with an amyloidosis, Friedreich's ataxia, frontotemporal lobar degeneration, Kennedy's disease, multiple system atrophy, multiple sclerosis, primary lateral sclerosis, progressive supranuclear palsy, spinal muscular atrophy, transverse myelitis, Refsum's disease, and spinocerebellar ataxia.

Seizure diseases and disorders of the CNS involve inappropriate and/or abnormal electrical conduction in the CNS, and include, but are not limited to: epilepsy (i.e., absence seizures, atonic seizures, benign Rolandic epilepsy, childhood absence, clonic seizures, complex partial seizures, frontal lobe epilepsy, febrile seizures, infantile spasms, juvenile myoclonic epilepsy, juvenile absence epilepsy, Lennox-Gastaut syndrome, Landau-Kleffner Syndrome, Dravet's syndrome, Otahara syndrome, West syndrome, myoclonic seizures, mitochondrial disorders, progressive myoclonic epilepsies, psychogenic seizures, reflex epilepsy, Rasmussen's Syndrome, simple partial seizures, secondarily generalized seizures, temporal lobe epilepsy, toniclonic seizures, tonic seizures, psychomotor seizures, limbic epilepsy, partial-onset seizures, generalized-onset seizures, status epilepticus, abdominal epilepsy, akinetic seizures, autonomic seizures, massive bilateral myoclonus, catamenial epilepsy, drop seizures, emotional seizures, focal seizures, gelastic seizures, Jacksonian March, Lafora Disease, motor seizures, multifocal seizures, nocturnal seizures, photosensitive seizure, pseudo seizures, sensory seizures, subtle seizures, sylvan seizures, withdrawal seizures, and visual reflex seizures).

Behavioral disorders are disorders of the CNS characterized by aberrant behavior on the part of the afflicted subject and include, but are not limited to: sleep disorders (i.e., insomnia, parasomnias, night terrors, circadian rhythm sleep disorders, and narcolepsy), mood disorders (i.e., depression, suicidal depression, anxiety, chronic affective disorders, phobias, panic attacks, obsessive-compulsive disorder, attention deficit hyperactivity disorder (ADHD), attention deficit disorder (ADD), chronic fatigue syndrome, agoraphobia, post-traumatic stress disorder, bipolar disorder), eating disorders (i.e., anorexia or bulimia), psychoses, developmental behavioral disorders (i.e., autism, Rett's syndrome, Aspberger's syndrome), personality disorders and psychotic disorders (i.e., schizophrenia, delusional disorder, and the like).

Lysosomal storage disorders are metabolic disorders which are in some cases associated with the CNS or have CNS-specific symptoms; such disorders include, but are not limited to: Tay-Sachs disease, Gaucher's disease, Fabry disease, mucopolysaccharidosis (types I, II, III, IV, V, VI and VII), glycogen storage disease, GM1-gangliosidosis, metachromatic leukodystrophy, Farber's disease, Canavan's leukodystrophy, and neuronal ceroid lipofuscinoses types 1 and 2, Niemann-Pick disease, Pompe disease, and Krabbe's disease.

In one aspect, the antibody is used to detect a neurological disorder before the onset of symptoms and/or to assess the severity or duration of the disease or disorder. In one aspect, the antibody permits detection and/or imaging of the neurological disorder, including imaging by radiography, tomography, or magnetic resonance imaging (MM).

In one aspect, a low affinity anti-BBB-R antibody for use as a medicament is provided. In further aspects, a low affinity anti-BBB-R antibody for use in treating a neurological disease or disorder is provided (e.g., Alzheimer's disease). In certain embodiments, a low affinity anti-BBB-R antibody for use in a method of treatment is provided. In certain embodiments, the invention provides a low affinity anti-BBB-R antibody for use in a method of treating an individual having a neurological disease or disorder comprising administering to the individual an effective amount of the anti-BBB-R antibody (optionally coupled to a neurological disorder drug). In one such embodiment, the method further comprises administering to the individual an effective amount of at least one additional therapeutic agent. In further embodiments, the invention provides an anti-BBB-R antibody for use in reducing or inhibiting amlyoid plaque formation in a patient at risk or suffering from a neurological disease or disorder (e.g., Alzheimer's disease). An "individual" according to any of the above embodiments is optionally a human. In certain aspect, the anti-BBB-R antibody for use in the methods of the invention improves uptake of the neurological disorder drug with which it is coupled.

In a further aspect, the invention provides for the use of a low affinity anti-BBB-R antibody in the manufacture or preparation of a medicament. In one embodiment, the medicament is for treatment of neurological disease or disorder. In a further embodiment, the medicament is for use in a method of treating neurological disease or disorder comprising administering to an individual having neurological disease or disorder an effective amount of the medicament. In one such embodiment, the method further comprises administering to the individual an effective amount of at least one additional therapeutic agent.

In a further aspect, the invention provides a method for treating Alzheimer's disease. In one embodiment, the method comprises administering to an individual having Alzheimer's disease an effective amount of a multispecific antibody which binds both BACE1 and TfR. In one such embodiment, the method further comprises administering to the individual an effective amount of at least one additional therapeutic agent. An "individual" according to any of the above embodiments may be a human.

The anti-BBB-R antibodies of the invention can be used either alone or in combination with other agents in a therapy. For instance, the anti-BBB-R antibody of the invention may be co-administered with at least one additional therapeutic agent. In certain embodiments, an additional therapeutic agent is a therapeutic agent effective to treat the same or a different neurological disorder as the anti-BBB-R antibody is being employed to treat. Exemplary additional therapeutic agents include, but are not limited to: the various neurological drugs described above, cholinesterase inhibitors (such as donepezil, galantamine, rovastigmine, and tacrine), NMDA receptor antagonists (such as memantine), amyloid beta peptide aggregation inhibitors, antioxidants, γ-secretase modulators, nerve growth factor (NGF) mimics or NGF gene therapy, PPARγ agonists, HMS-CoA reductase inhibitors (statins), ampakines, calcium channel blockers, GABA receptor antagonists, glycogen synthase kinase inhibitors, intravenous immunoglobulin, muscarinic receptor agonists, nicrotinic receptor modulators, active or passive amyloid beta peptide immunization, phosphodiesterase inhibitors, serotonin receptor antagonists and anti-amyloid beta peptide antibodies. In certain embodiments, the at least one additional therapeutic agent is selected for its ability to mitigate one or more side effects of the neurological drug.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with other interventional therapies such as, but not limited to, radiation therapy, behavioral therapy, or other therapies known in the art and appropriate for the neurological disorder to be treated or prevented.

The anti-BBB-R antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Lipid-based methods of transporting the antibody or fragment thereof across the blood-brain barrier include, but are not limited to, encapsulating the antibody or fragment thereof in liposomes that are coupled to antibody binding fragments that bind to receptors on the vascular endothelium of the blood-brain barrier (see e.g., U.S. Patent Application Publication No. 20020025313), and coating the antibody or active fragment thereof in low-density lipoprotein particles (see e.g., U.S. Patent Application Publication No. 20040204354) or apolipoprotein E (see e.g., U.S. Patent Application Publication No. 20040131692).

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-BBB-R antibody.

V. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-BBB-R antibody.

The article of manufacture optionally further comprises a package insert with instructions for treating a neurological disorder in a subject, wherein the instructions indicate that treatment with the antibody as disclosed herein treats the neurological disorder, and optionally indicates that the antibody has improved uptake across the BBB due to its low affinity for the BBB-R.

III. Examples

This example evaluated the transferrin receptor (TfR), which mediates iron transport into the brain via the holo-transferrin complex (Skarlatos et al. *Brain Res* 683: 164-171 (1995)). A human chimeric anti-murine transferrin receptor (anti-TfR$^A$) antibody that does not compete with endogenous transferrin binding to TfR was compared to a human control IgG in a double-labeled experiment for uptake in wild type mouse brain. A single trace dose (approximately 50 µg/kg) of [$^{131}$I]anti-TfR$^A$ and [$^{125}$I]control IgG was injected into wild type mice intravenously (i.v.) and brain uptake was measured at 5 min., 0.5, 1, 4, 24, 48, and 72 hours. A significant increase in [$^{131}$I]anti-TfR$^A$ uptake in the brain, measured as a percentage of injected dose per gram of brain, was observed at all time points (FIG. 1A). At its peak, 1 hour after injection, there was a >11-fold difference in [$^{131}$I]anti-TfR$^A$ brain accumulation as compared to [$^{125}$I] control IgG (n=6). If unlabeled anti-TfR$^A$ (4 mg/kg body weight) was also co-administered, brain accumulation of [$^{131}$I]anti-TfR$^A$ was nearly reduced to the level of control IgG, indicating specific, target-driven uptake.

To evaluate whether significant antibody uptake in brain also occurs at therapeutic dose levels, wild type mice were administered either anti-TfR$^A$ or control IgG at 20 mg/kg intravenously (i.v.). Human antibody concentration in the cortex and serum was determined 1 and 24 hours after injection using a human Fc sandwich ELISA. Briefly, after the indicated time of administration, mice were perfused with D-PBS at a rate of 2 ml/min. for 8 minutes. Brains were extracted and the cortex and hippocampus were isolated, homogenized in 1% NP-40 (Cal-Biochem) in PBS containing Complete Mini EDTA-free protease inhibitor cocktail tablets (Roche Diagnostics). Homogenized brain samples were rotated at 4° C. for 1 hour before centrifugation at 14,000 rpm for 20 minutes. The supernatant was isolated for brain antibody measurement. Whole blood was collected prior to perfusion in serum separator microcontainer tubes (BD Diagnostics), allowed to clot for at least 30 minutes, and spun down at 5,000×g for 90 seconds. The supernatant was isolated for serum antibody measurements. Antibody concentrations in mouse serum and brain samples were measured by ELISA. NUNC 384-well Maxisorp immunoplates (Neptune, N.J.) were coated with F(ab')$_2$ fragment of donkey anti-human IgG, Fc fragment-specific polyclonal antibody (Jackson ImmunoResearch, West Grove, Pa.) overnight at 4° C. Plates were blocked with PBS containing 0.5% BSA for 1 hour at 25° C. Each antibody was used as an internal standard to quantify respective antibody concentration. Plates were washed with PBS containing 0.05% Tween-20 using a microplate washer (Bio-Tek Instruments, Inc., Winooski, Vt.). Standards and samples were diluted in PBS containing 0.5% BSA, 0.35 M NaCl, 0.25% CHAPS, 5 mM EDTA, 0.05% Tween-20 and 15 ppm Proclin, and were added to the microplate for two hours at 25° C. Bound antibody was detected with horseradish peroxidase-conjugated F(ab')$_2$ goat anti-human IgG, Fc-specific polyclonal antibody (Jackson ImmunoResearch), developed using 3,3', 5,5'-tetramethyl benzidine (TMB) (KPL, Inc., Gaithersburg, Md.) and absorbance measured at 450 nm on a Multiskan Ascent reader (Thermo Scientific, Hudson, N.H.). Concentrations were determined from the standard curve using a four-parameter non-linear regression program. The assay had lower limit of quantification (LLOQ) values of 3.12 ng/ml in serum and 15.6 ng/g in brain. Statistical analysis of differences between experimental groups was performed using a two-tailed unpaired t-test.

Figure 1B:
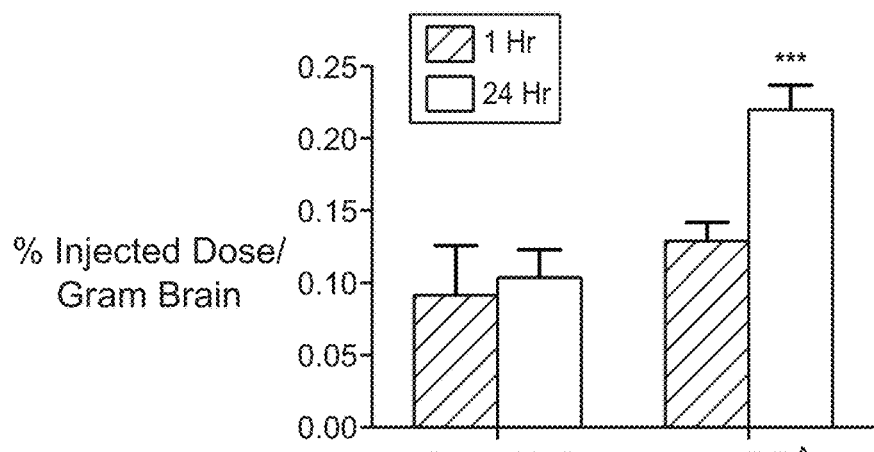
Figure 1C:
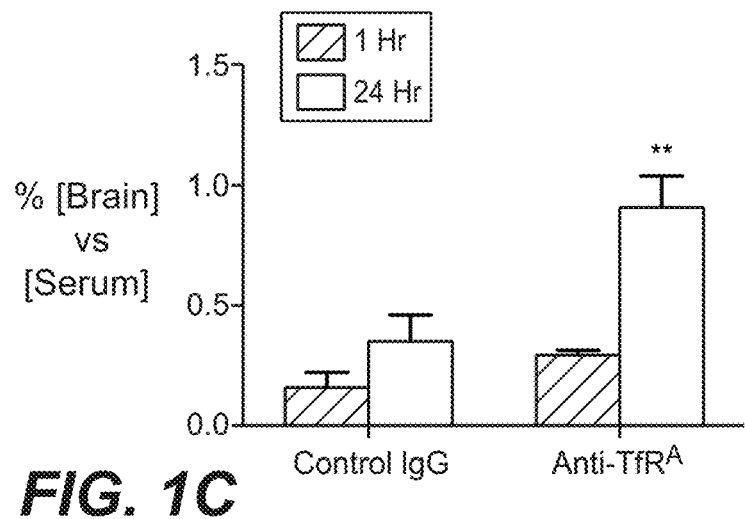

Compared to control IgG, concentration of anti-TfR$^A$ was significantly higher in the brain 24 hours after antibody administration (FIG. 1B, p=0.0002, n=10). Additionally, human IgG concentration in brain was >2.5-fold higher compared to serum for anti-TfR$^A$ compared to control IgG at 24 hours (FIG. 1C, p=0.003, n=10). Together with the radiolabeled trace data, these results indicate that systemically administered anti-TfR$^A$ can accumulate in the brain, however the tissue distribution of antibody in brain remained to be understood.

Figure 1D:
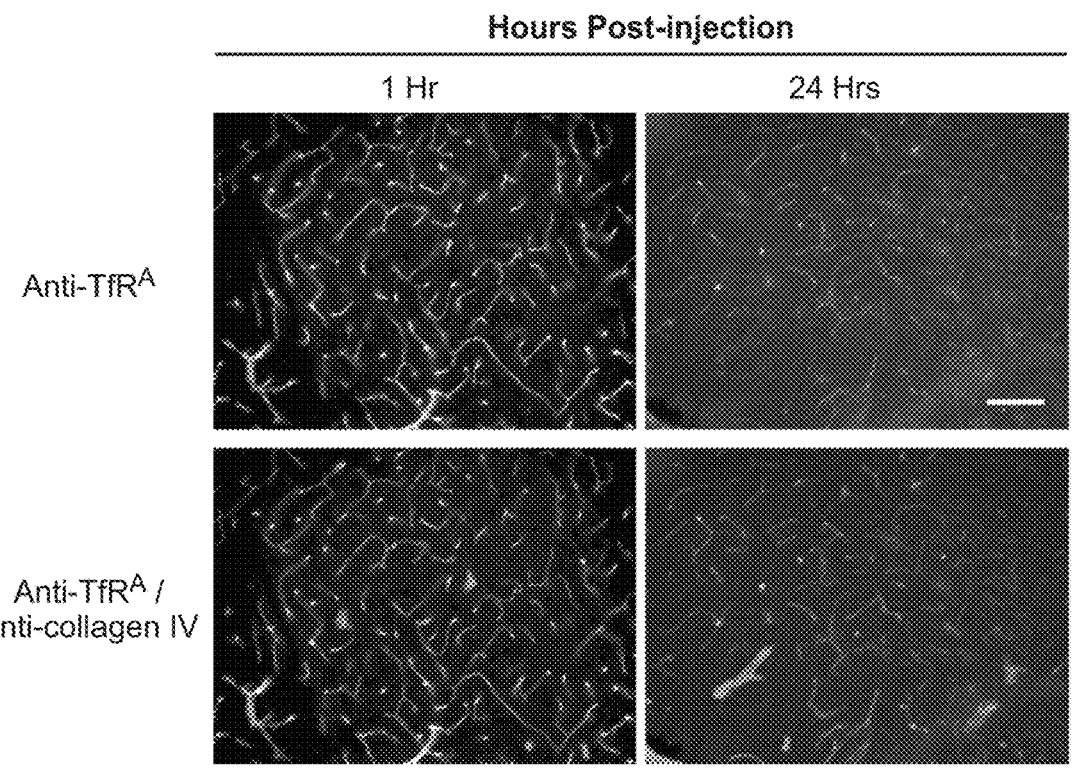
Figure 1E:
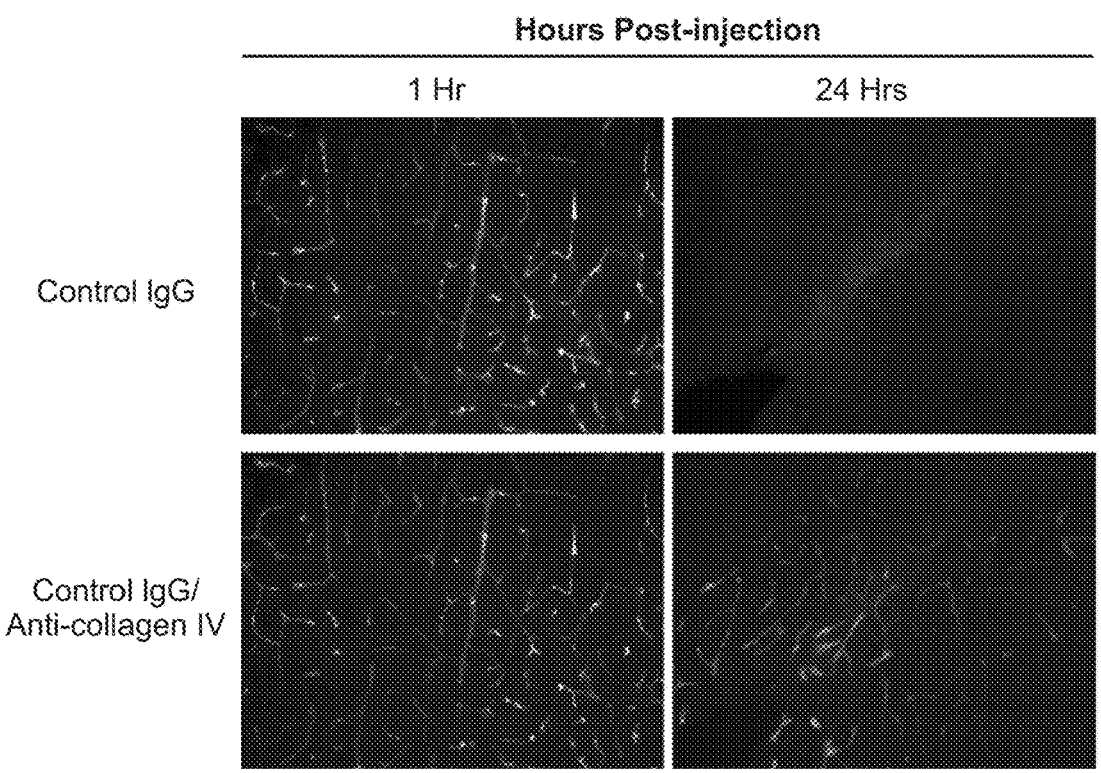

To address the distribution of systemically administered antibodies in brain, wild type mice were injected 20 mg/kg i.v. with either anti-TfR$^A$ or control IgG, perfused with PBS to flush out any remaining circulating antibody, and brain sections were stained with fluorescent anti-human secondary IgG to determine antibody localization. After 1 hour of circulation, anti-TfR$^A$ had a pronounced vascular distribution, as indicated by its co-localization with the basement membrane marker anti-collagen IV (FIG. 1D, left column). Although less pronounced, control IgG also localized to the vasculature, indicating that after 1 hour of exposure, therapeutic dose levels of systemically administered IgG maintains a vascular distribution (FIG. 1E, left column). However, there was a marked difference in antibody localization 24 hours after injection. Anti-TfR$^A$ distribution was no longer exclusively vascular, but instead, exhibited modest parenchymal staining (FIG. 1D, right columns). In contrast, control IgG antibody was largely absent in brain tissue 24 hours after injection (FIG. 1E, right columns). These results indicate that when dosed at therapeutically relevant levels, anti-TfR$^A$ may penetrate the BBB as evidenced by modest parenchymal staining, however, the bulk of the brain-accumulated antibody was largely confined to endothelial cells of the BBB.

Accumulation in the parenchyma requires binding to surface TfRs expressed on brain endothelial cells as well as dissociation from the receptor following RMT. Without being bound by any theory, it was hypothesized that reduced affinity for TfR may facilitate dissociation after RMT and allow enhanced accumulation in the parenchyma. Further, an anti-TfR with reduced affinity would be less efficiently captured and transported in a concentration-limited environment, such as in the brain, where anti-TfR concentrations are low. In a clinical setting, however, serum levels of an anti-TfR therapeutic would still be sufficiently high to maintain saturation of the receptor in the vascular lumen.

Figure 2A:
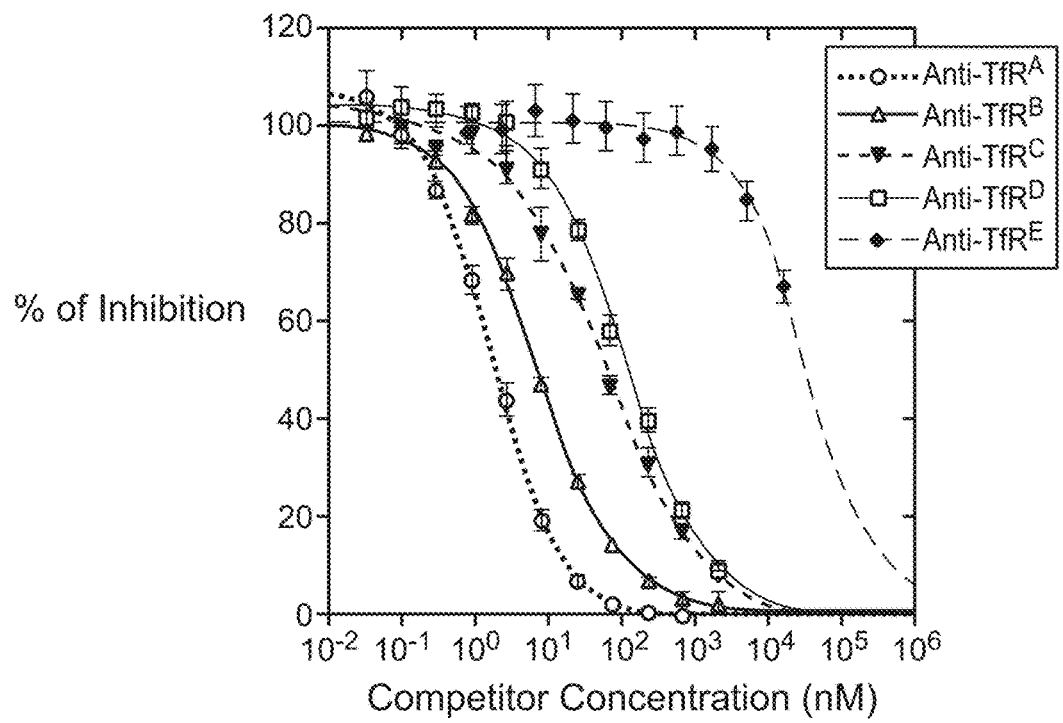

To test this prediction, variants of anti-TfR$^A$ were generated that vary in their binding affinity for TfR. These variants were tested in a competition ELISA assay (FIG. 2A); anti-TfR$^A$ had the strongest affinity and lowest IC50 of any of the tested antibodies for TfR, and each of anti-TfR$^{B,C,D}$ had successively lower affinity and higher IC50. Later, variant anti-TfR$^E$ was generated and tested in the same assay along with anti-TfR$^{A,B,C,D}$ variants; as shown in FIG. 2A, it was substantially less able to compete for binding to TfR than any of the other tested anti-TfR antibodies, and it had a corresponding high IC50 value (Table 2).

TABLE 2

| IC50 measurements for anti-TfR antibodies | | |
|---|---|---|
| Antibody | IC50 (nM) | Standard deviation |
| Anti-TfR$^A$ | 1.7 | 0.1 |
| Anti-TfR$^B$ | 6.9 | 0.4 |
| Anti-TfR$^C$ | 65 | 12 |
| Anti-TfR$^D$ | 111 | 16 |
| Anti-TfR$^E$ | >5 × 10$^4$ | — |

Figure 2B:
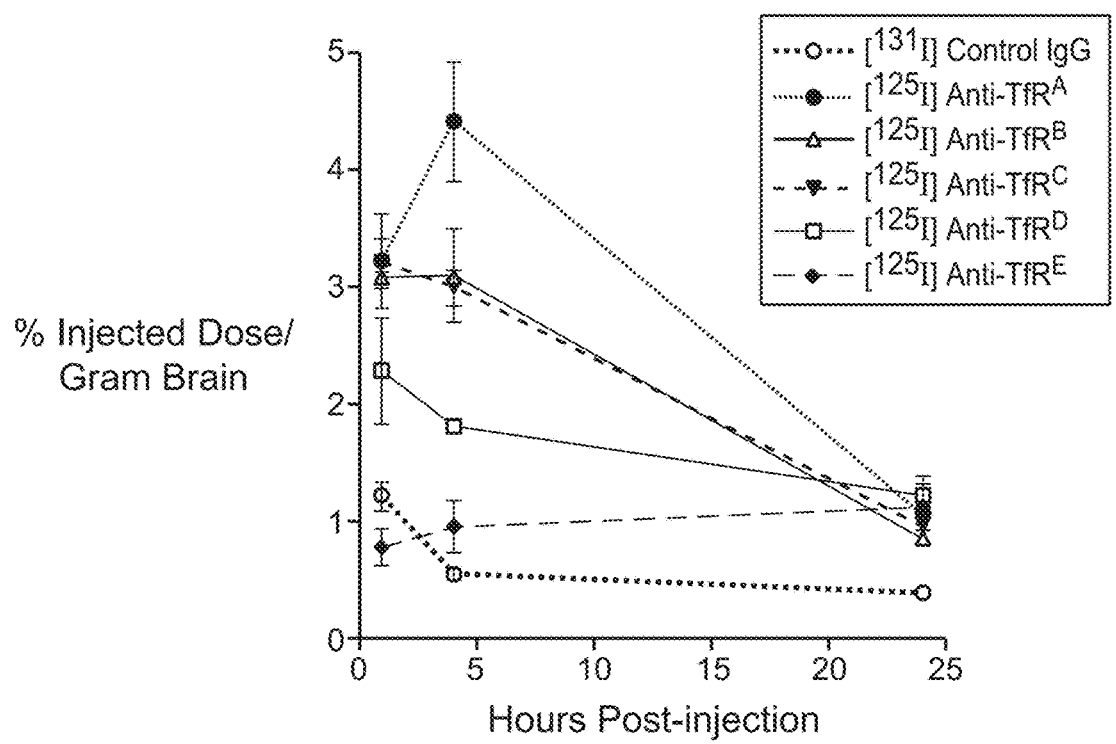

These variants were tested in both a non-TfR saturating (trace dosing) and TfR saturating (therapeutic dosing) environment. Trace levels of [$^{125}$I]anti-TfR$^A$, [$^{125}$I]anti-TfR$^B$, [$^{125}$I]anti-TfR$^C$, [$^{125}$I]anti-TfR$^D$ and [$^{125}$I]anti-TfR$^E$ (which vary in affinity for TfR, with the affinity of anti- TfR$^A$>affinity of anti-TfR$^B$>affinity of anti-TfR$^C$>affinity of anti-TfR$^D$>affinity of anti-TfR$^E$) were injected i.v. into mice and brain uptake was measured 1, 4, or 24 hours after injection. This assay was performed originally with [$^{125}$I]anti-TfR$^A$, [$^{125}$I]anti-TfR$^B$, [$^{125}$I]anti-TfR$^C$, and [$^{125}$I]anti-TfR$^D$, and later repeated upon the construction of [$^{125}$I]anti-TfR$^E$, the results of which are shown in FIG. 2B. Consistent with the proposed model, trace dose levels of lower affinity anti-TfR antibodies resulted in less uptake in brain compared to higher affinity variants (FIG. 2B). In striking contrast to trace dosing, however, brain uptake of these same lower-affinity variants at therapeutic levels (20 mg/kg assessed at 1 and 24 hours) exhibited increased brain uptake at 24 hours as affinity was lowered, while no significant difference in uptake was observed at 1 hour (FIG. 2C). These data support the hypothesis that a lower affinity RMT antibody would exhibit decreased transport under limiting concentrations while transport under saturating conditions would be unaffected.

Thus, the following model is proposed: compared to a high affinity antibody, fewer low affinity antibodies bind to receptors on the luminal side of the vasculature under non-saturating concentrations, leading to lower endothelial uptake (FIG. 2D, left panels). At a higher therapeutic dose, however, luminal receptors would be saturated regardless of affinity resulting in similar endothelial uptake (FIG. 2D, right panels). Under these conditions, lower affinity RMT antibodies can achieve greater brain accumulation by 1) maximizing dissociation from the RMT target facilitating release into the brain, and 2) reducing the likelihood of efflux out of the brain as concentrations are limited on the parenchymal side of the BBB. Thus in a therapeutic setting, a lower affinity antibody for an RMT target is surprisingly advantageous for parenchymal accumulation.

Figure 2E:
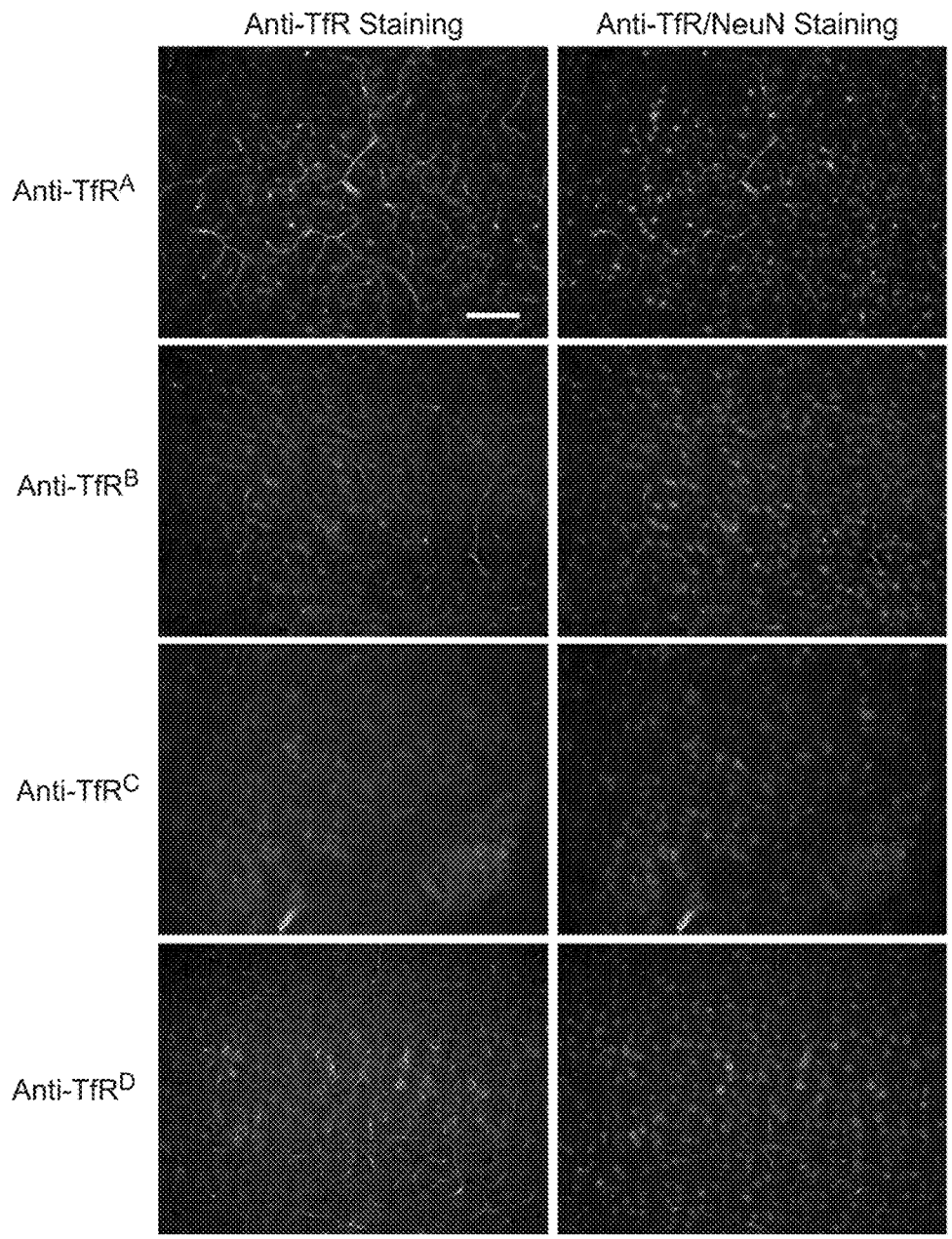
Figure 2F:
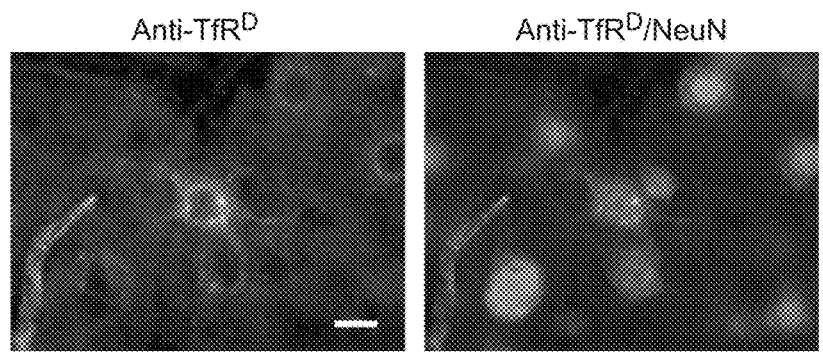

To evaluate the localization of these variants exhibiting increased brain uptake, mice were dosed i.v. with 20 mg/kg of either the high affinity anti-TfR$^A$ or the lower affinity variants anti-TfR$^{B,C,D}$. After 24 hours, animals were PBS-perfused and brain sections were co-stained for human IgG and the neuronal marker NeuN (FIG. 2E). As observed before, high affinity anti-TfR$^A$ treated animals had mostly vascular staining with low levels of parenchymal signal (FIG. 2E, top row). However, the lower affinity anti-TfR$^{B,C,D}$ had noticeably more pronounced cellular staining not depicting cortical blood vessels (FIG. 2E, data for anti-TfR$^{B,C,D}$). Furthermore, co-localized staining with NeuN indicated a redistribution of antibody from the vasculature to neurons. This is especially pronounced in a representative higher magnification image of anti-TfR$^D$ variant (FIG. 2F). Together with the brain uptake data, these results indicate that a significantly higher brain accumulation of antibody can be achieved by lowering the affinity of anti-TfR for TfR, and that lower affinity antibodies such as anti-TfR$^D$ selectively distributed to neurons.

Transport of anti-TfR antibodies across the BBB was further established when evaluating a bispecific antibody (anti-TfR$^A$/BACE1) that binds both TfR and the amyloid precursor protein (APP) cleavage enzyme, beta secretase (BACE1) (FIG. 3A). The high affinity anti-TfR$^A$ was used to engineer the TfR binding arm of the bispecific using standard 'knob in hole' bispecific antibody construction technology (see, e.g., Ridgway et al., Protein Eng. (1996) 9(7): 617-621). In addition to the knob and hole mutations in the Fc for anti-TfR (hole) and anti-BACE1 (knob), the anti-TfR arm of the antibody comprised a mutation in the Fc region that abrogated glycosylation (N297G). The knob and hole half-antibodies were purified separately and annealed to generate an aglycosylated bispecific IgG in vitro. The binding affinity of the anti-TfR$^A$/BACE1 antibody to TfR was considerably reduced compared to the parental anti-TfR$^A$ due to the loss of bivalent binding (FIG. 3B). BACE1 is expressed primarily on neurons in the CNS and is considered to be the primary contributor of beta amyloid (A$\beta_{1-40}$) formation via APP cleavage (Vassar et al., Science 286:735-741 (1999)). An antibody to BACE1 has been described as an effective means to inhibit BACE1 activity, and may reduce A$\beta_{1-40}$ production in vivo. Inhibition of BACE1 by anti-TfR/BACE1 was examined in a HEK293 cell line stably expressing APP. Compared to anti-BACE1, the bispecific antibody had both similar efficacy and potency in inhibiting A$\beta_{1-40}$ production, suggesting that the anti-TfR/BACE1 is a fully functional large molecule inhibitor of BACE1 activity (FIG. 3C).

Figure 3D:
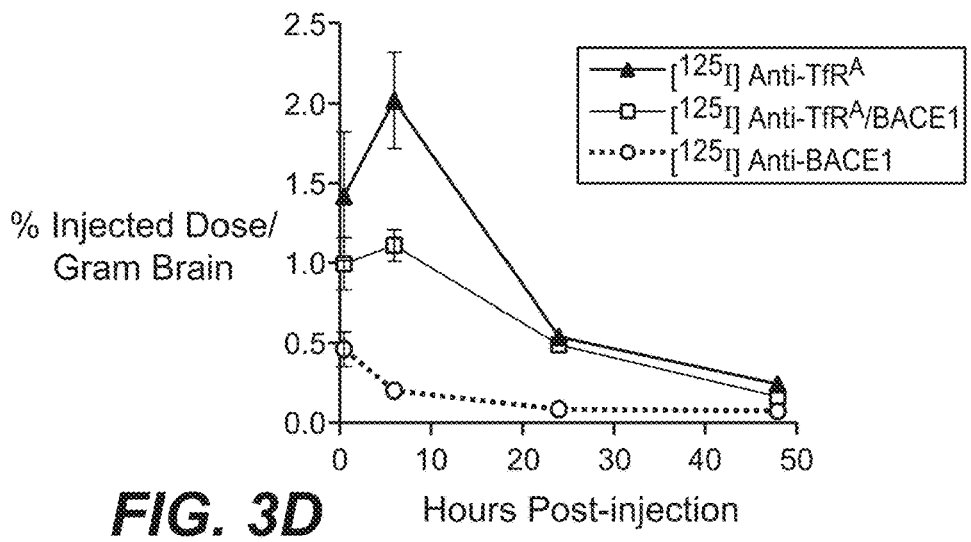
Figure 3E:
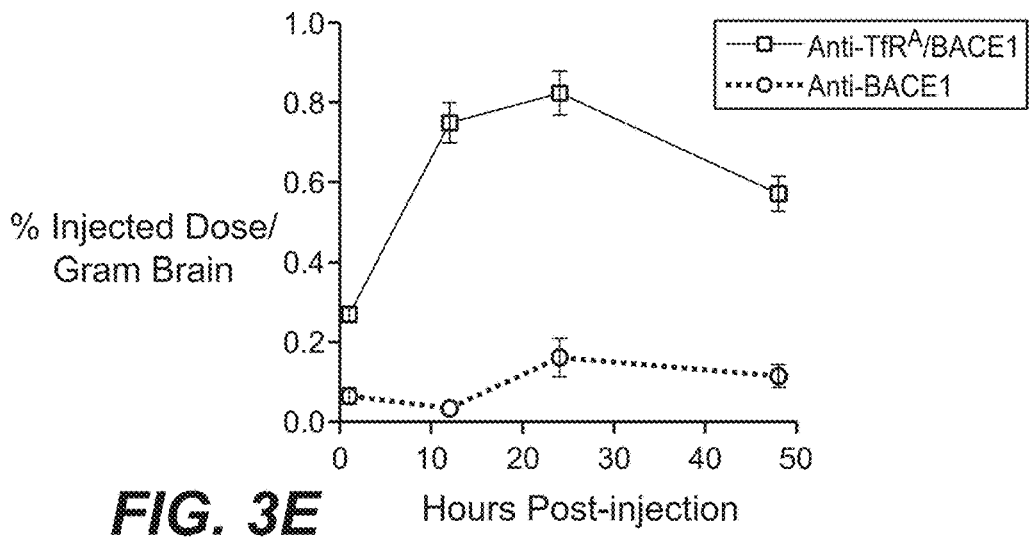
Figure 3F:
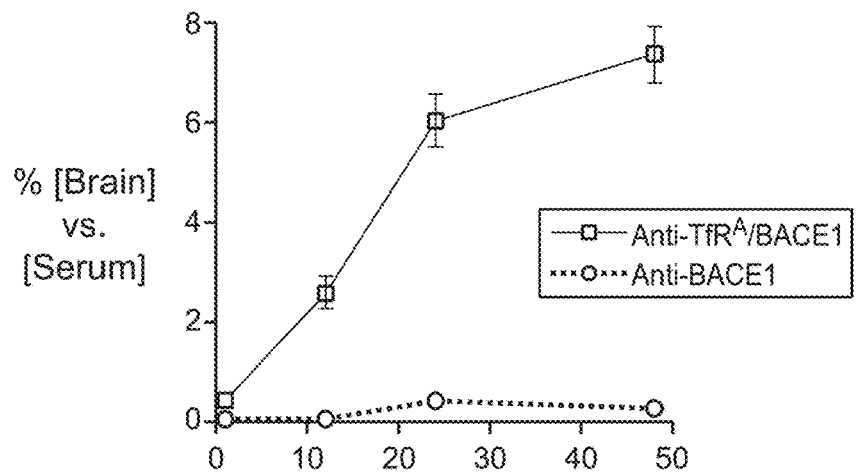

Based on this model, this lower affinity bispecific would be expected to be a more favorable candidate for increased uptake compared to the anti-TfR alone. To investigate the brain accumulation of the bispecific antibody, trace doses of [$^{125}$I]anti-TfR$^A$/BACE1 were compared to [$^{125}$I]anti-TfR$^A$ and [$^{125}$I]anti-BACE1 and brain uptake was evaluated at 30 min., 6, 24, and 48 hours after i.v. injection. Significantly higher brain uptake was observed with [$^{125}$I]anti-TfR/BACE1 compared to [$^{125}$I]anti-BACE1 at all time points (FIG. 3d, n=4). Consistent with the affinity hypothesis, brain uptake of this non-saturating trace dose of [$^{125}$I]anti-TfR$^A$ was much greater than that of the lower affinity [$^{125}$I]anti-TfR$^A$/BACE1. To assess antibody accumulation at therapeutic dose levels, mice were injected i.v. with anti-TfR$^A$/BACE1 or anti-BACE1 at 20 mg/kg and brain uptake of antibody was determined after 1, 12, 24, and 48 hours. Compared to the monospecific anti-BACE1, administration of the bispecific anti-TfR$^A$/BACE1 resulted in a significantly higher brain uptake at all time points (FIG. 3E). As predicted by the affinity model, the extent of uptake was significantly greater than the higher affinity anti-TfR$^A$ alone (compare FIG. 3E to 1B). Peak accumulation was achieved at 24 hours after injection, reaching concentrations of ~20 nM and remained elevated 48 hours after injection, even as peripheral levels of antibody cleared to ~12% of its concentration at 1 hour. Enhanced uptake by the bispecific is dramatically apparent when comparing the average percent of antibody in the brain versus the serum (FIG. 3F).

Figure 3G:
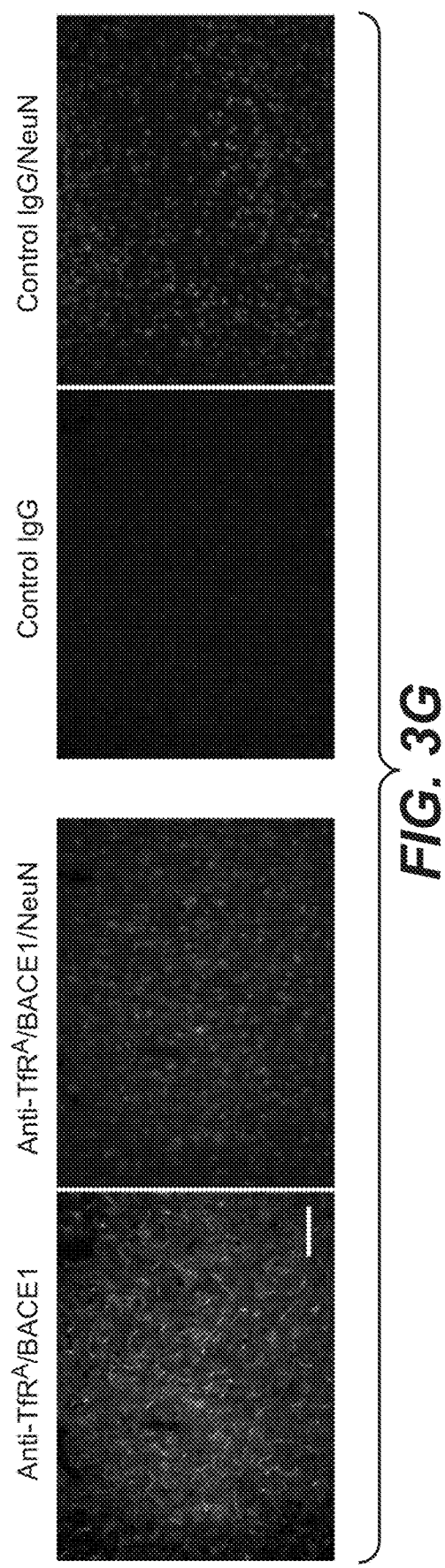

To determine localization of anti-TfR$^A$/BACE1 after systemic administration, mice were PBS-perfused 24 hours after injection, and antibody distribution was visualized with anti-human fluorescent secondary (FIG. 3G). Similar to the lower affinity anti-TfR antibody localization, there was substantial staining of the parenchyma in addition to vascular staining. Parenchymal co-localization with NeuN indicated that these antibodies were localized to the neuronal population. In contrast, animals injected with control IgG showed a complete lack of both vascular and parenchymal staining. Together, these data indicate that the bispecific anti-TfR$^A$/BACE1 traverses across the BBB and can significantly accumulate in the brain parenchyma.

Figure 4A:
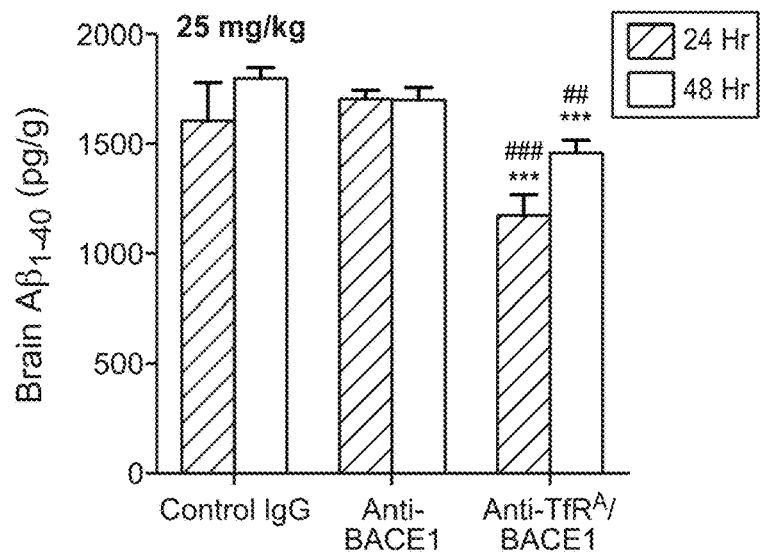
FIGS. 4A-E show that a single systemic dose of anti-TfR$^A$/BACE1 significantly reduces central and peripheral Aβ$_{1-40}$.
Figure 4B:
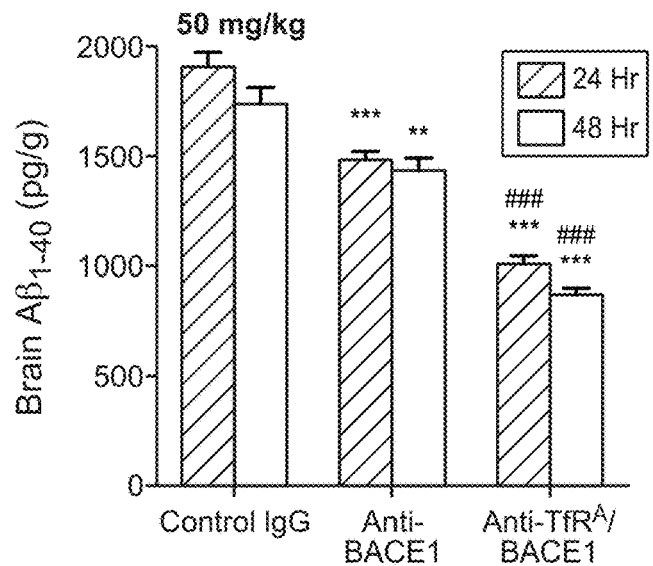
Figure 4C:
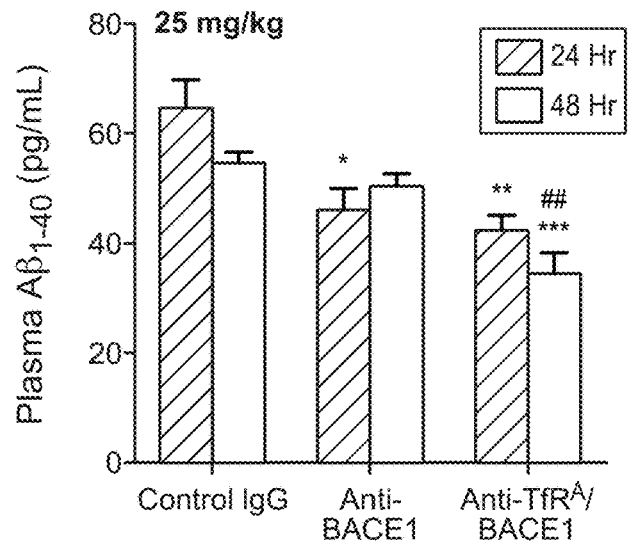
Figure 4D:
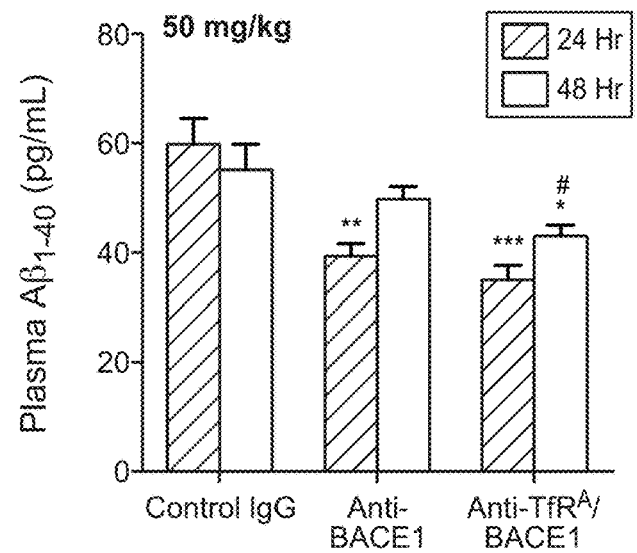
Figure 4E:
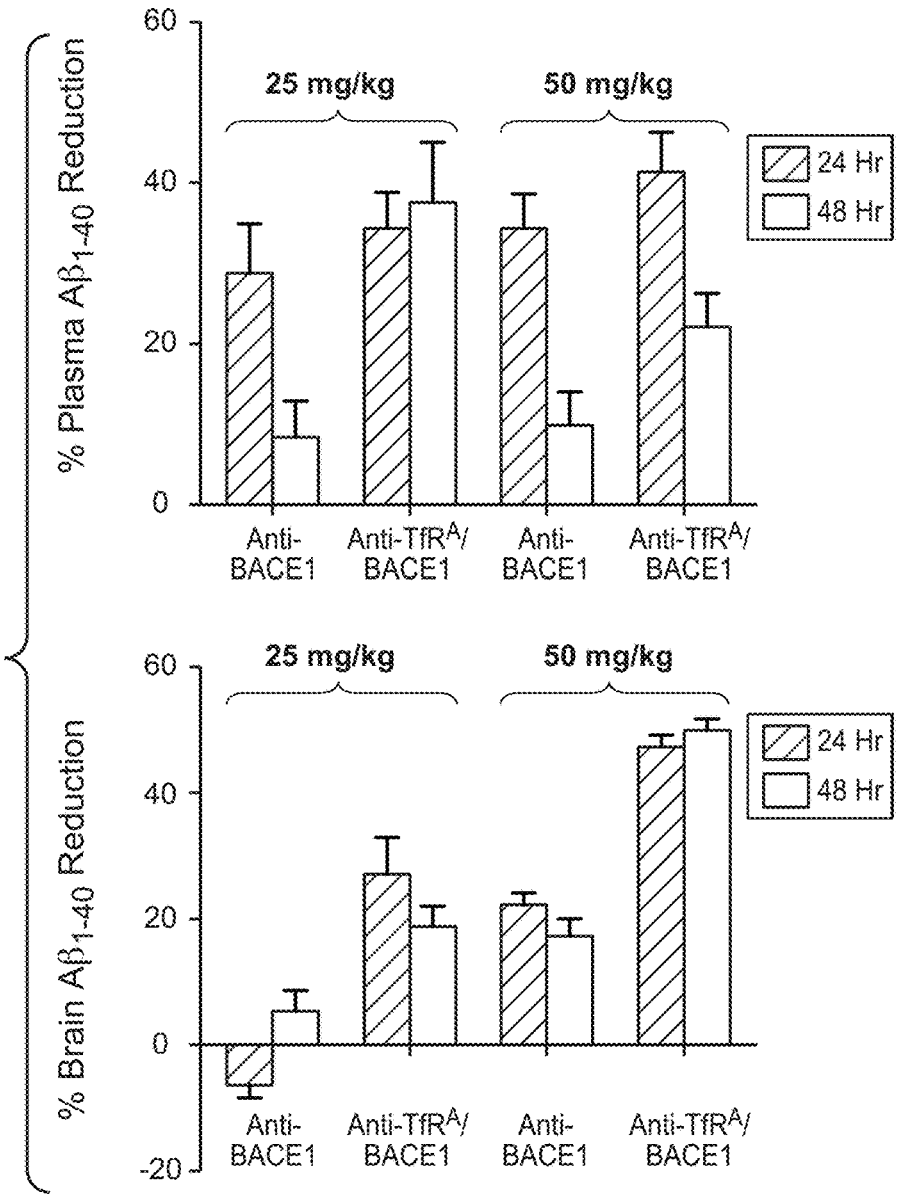

To assess the efficacy of anti-TfR$^A$/BACE1 on A$\beta_{1-40}$ production in vivo, wild type mice were administered a single 25 mg/kg or 50 mg/kg dose of control IgG, anti-BACE1, or anti-TfR/BACE1. Based on the observation that brain antibody uptake peaks 24 hours after injection (see FIG. 3E), brain and plasma A$\beta_{1-40}$ levels were determined at 24 and 48 hours after i.v. antibody administration. At 25 mg/kg, anti-TfR$^A$/BACE1 was able to significantly reduce brain A$\beta_{1-40}$ levels compared to control IgG both after 24 (p=0.001, n=10) and 48 (p=0.0003, n=10) hours post-injection, while anti-BACE1 had no effect on $A\beta_{1-40}$ reduction (FIG. 4A). At 50 mg/kg, anti-TfR$^A$/BACE1 had a even more dramatic effect on reducing brain $A\beta_{1-40}$ at both time points compared to control IgG (FIG. 3B, p<0.0001, n=10 for both 24 and 48 hr). Administration of anti-BACE1 at this dose also significantly reduced brain $A\beta_{1-40}$ levels compared to control (p<0.0001, n=10 for 24 hr; p=0.006, n=10 for 48 hr), though to a significantly lesser extent than the bispecific anti-TfR$^A$/BACE1 (p<0.0001, n=10 for both 24 and 48 hours). Notably, the ability of the bispecific to reduce $A\beta_{1-40}$ was 2- to 3-fold greater than anti-BACE1 for all time points and doses measured. The maximal effect of anti-TfR$^A$/BACE1 was achieved 48 hours after injection at 50 mg/kg, with a 50.0±1.9% reduction in brain $A\beta_{1-40}$ compared to control IgG (FIG. 4E). Significant reductions in peripheral $A\beta_{1-40}$ was also observed at both doses and time points for anti-TfR$^A$/BACE1 (FIGS. 4C-D). Treatment with anti-BACE1 resulted in a reduction in peripheral $A\beta_{1-40}$ only at the 24 hour time point (p=0.01 for 25 mg/kg, p=0.002 for 50 mg/kg; n=10 for each). These data confirm that antibodies engineered to cross the BBB can be pharmacodynamically efficacious. Furthermore, the increase in brain penetrance of the bispecific renders it more potent BACE1 inhibitor drug by significantly reducing brain $A\beta_{1-40}$ levels.

Figure 8A:
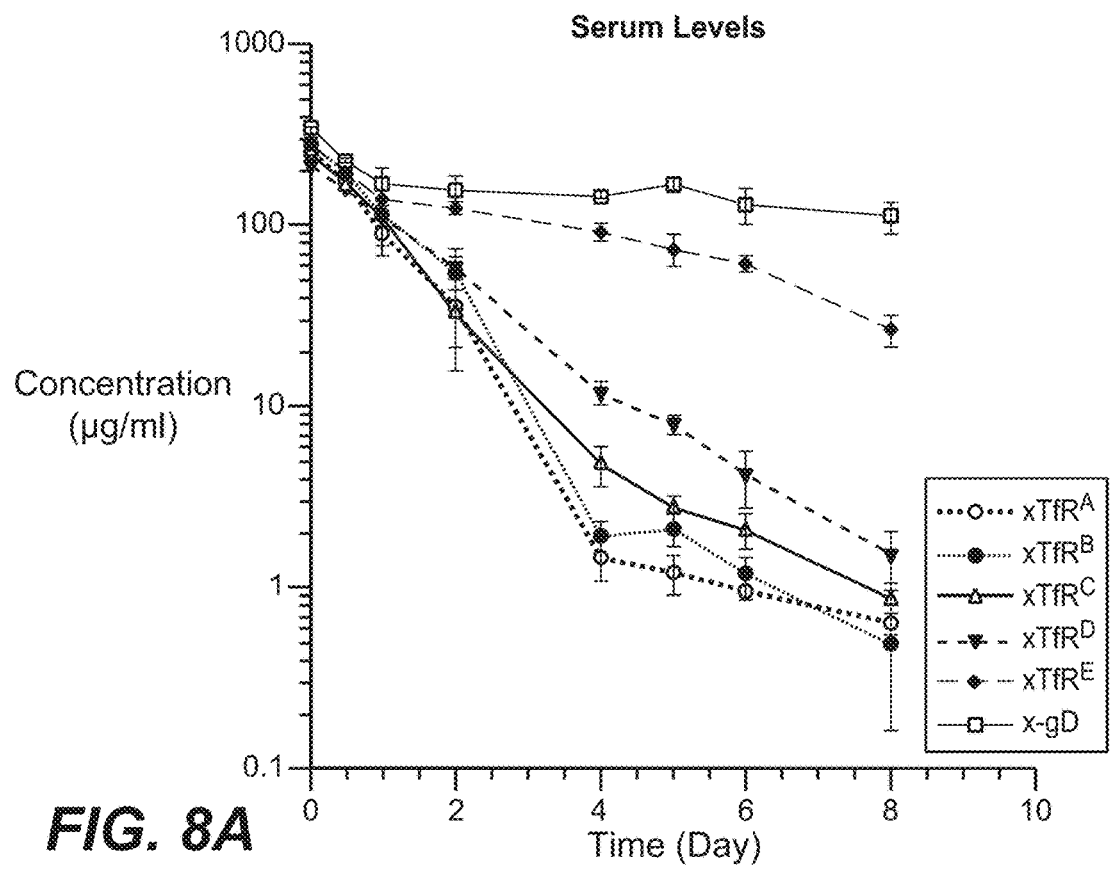
FIGS. 8A-B depict the quantification of anti-TfR$^{A,B,C,D,E}$ in the serum (FIG. 8A) and brain (FIG. 8B) after a single therapeutic dose administration in mice. Six-eight week old wild type female C57B/6 mice were used for all studies. Mice were intravenously injected with 20 mg/kg of anti-TfR variants or control IgG. Antibody levels in brain and serum were measured at 1 and 12 hours and 1, 2, 4, 5, 6, and 8 days post injection. Total injection volume did not exceed 260 μL and antibodies were diluted in D-PBS (Invitrogen) when necessary. The experiment was performed using the same protocol as the experiment whose results are shown in FIG. 1B.
Figure 8B:
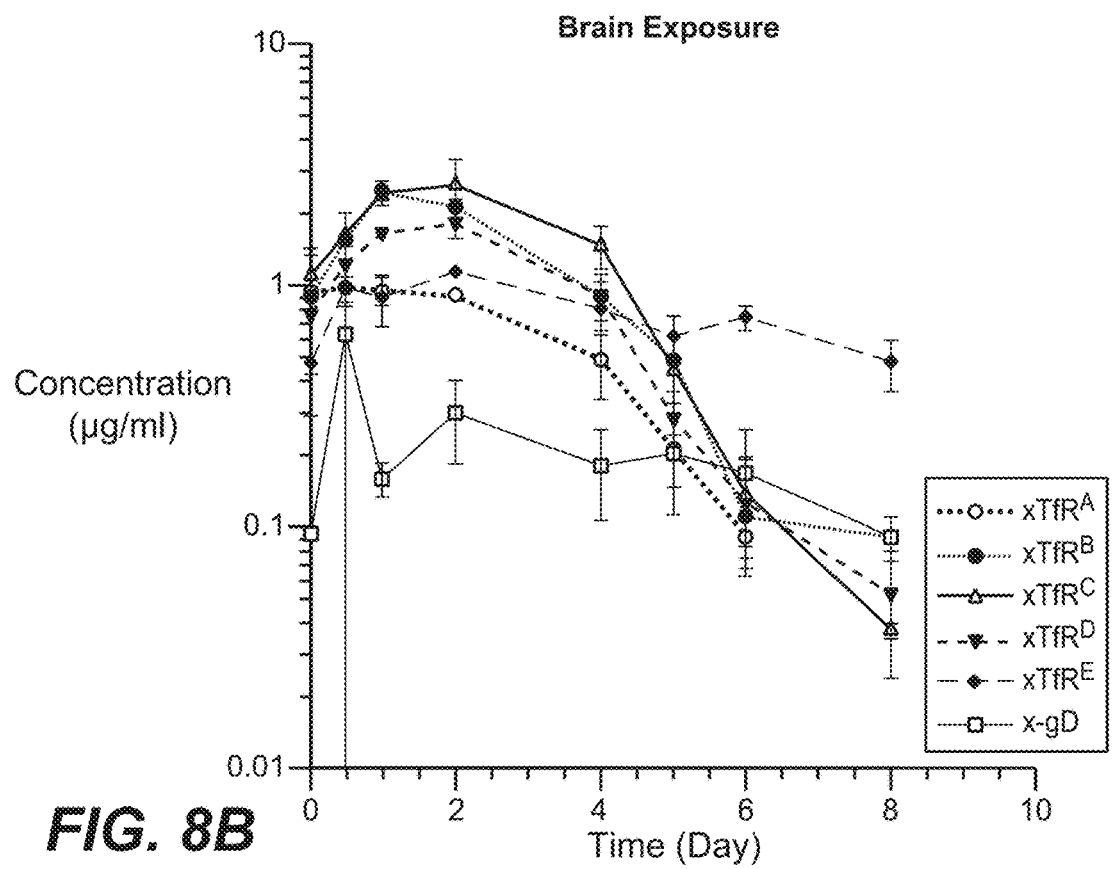

At therapeutic doses of 20 mg/kg, however, BBB penetrance and entry into the non-vascular portions of the CNS was enhanced in the anti-TfR$^E$-treated animals relative to the anti-TfR$^A$ or anti-TfR$^D$-treated animals (FIG. 8B). Notably, anti-TfR$^D$ achieved a higher initial concentration in the brain, which steadily decreased after day 2; anti-TfR$^E$, on the other hand, retained a consistently high level of brain exposure over the tested 8 day period. Relatedly, anti-TfR$^E$ concentration in the serum decreased the least of all of the anti-TfR antibodies over the assessed period (FIG. 8A). In all, this data indicates that generally a lower affinity for TfR surprisingly reduces serum clearance and increases brain exposure, but that at some threshold the lower affinity begins to impair the maximum brain exposure obtainable with the antibody. In this example, an optimum would seem to be found between the affinities of antibodies anti-TfR$^D$ and anti-TfR$^E$ for transferrin receptor.

Importantly, these data highlight several causative mechanisms behind increasing uptake of an antibody into the CNS using a lower-affinity antibody approach. First, high affinity anti-TfR antibodies (e.g., anti-TfR$^A$, FIG. 1D) limit brain uptake by quickly saturating the TfR in the brain vasculature, thus reducing the total amount of antibody taken up into the brain and also restricting its distribution to the vasculature. Strikingly, lowering affinity (e.g., anti-TfR$^{B-E}$, and anti-TfR$^{A,D,E}$/BACE1, FIGS. 2C, 2E, 2F, 3E-G and 9C) improves brain uptake and distribution, with a robust shift observed in localization from the vasculature to neurons and associated neuropil. Second, the lower affinity of the antibody for TfR is proposed to impair the ability of the antibody to return to the vascular side of the BBB via TfR from the CNS side of the membrane because the overall affinity of the antibody for TfR is low and the local concentration of the antibody on the CNS side of the BBB is non-saturating due to the rapid dispersal of the antibody into the CNS compartment (see, e.g., FIGS. 1D, 2E and 2F). Third, in vivo, antibodies with less affinity for TfR are not cleared from the system as efficiently as those with greater affinity for TfR (see FIGS. 8A and 9B), and thus remain at higher circulating concentrations than their higher-affinity counterparts. This is advantageous because the circulating antibody levels of the lower-affinity antibody are sustained at therapeutic levels for a longer period of time than the higher-affinity antibody, which subsequently improves uptake of antibody in brain for longer period of time (compare anti-TfR$^A$/BACE1 to anti-TfR$^D$/BACE1 in FIG. 9C). Furthermore, this improvement in both plasma and brain exposure may reduce the frequency of dosing in the clinic, which would have potential benefit not only for patient compliance and convenience but also in lessening any potential side effects or off-target effects of the antibody and/or of a therapeutic compound coupled thereto.

Further studies were performed to assess whether further lessening the affinity of the bispecific anti-TfR$^A$/BACE1 antibody could further improve its BBB and parenchymal penetrance. Two further bispecific antibodies were constructed: anti-TfR$^D$/BACE1 and anti-TfR$^E$/BACE1, using the same construction methodology employed for the anti-TfR$^A$/BACE1 antibody. Competition ELISA assays were performed (FIG. 9A) and the resulting IC50s were as follows:

TABLE 3

IC50/affinity measurements for anti-TfR/BACE1 antibodies

| Antibody | IC50 | Kd (Biacore) (nM) |
|---|---|---|
| Anti-TfR$^A$/BACE1 | 15 nM | 33.3 ± 1.7 |
| Anti-TfR$^D$/BACE1 | 1.6 μM | 630 ± 50 |
| Anti-TfR$^E$/BACE1 | >50 μM | N.D. |

Surface plasmon resonance measurements of Kd were also made for the binding between each bispecific antibody and TfR. The BIACORE® analysis in Table 3 was performed as follows. Kd was measured using surface plasmon resonance assays using a BIACORE®-T-100 (BIAcore, Inc., Piscataway, N.J.) at 25° C. using penta-His Ab capture (Qiagen, Valencia, Calif.). Briefly, carboxymethylated dextran biosensor chips (CMS, BIACORE, Inc.) were activated with N-ethyl-N'-(3-dimethylaminopropyl)-carbodiimide hydrochloride (EDC) and N-hydroxysuccinimide (NHS) according to the supplier's instructions. Penta-His antibody was diluted with 100 mM sodium acetate, pH 4.0, to 50 μg/ml before injection at a flow rate of 5 μl/minute to achieve approximately 10000 response units (RU) of coupled protein. Following the injection of antibody, 1 M ethanolamine was injected to block unreacted groups. For kinetics measurements, MuTfR-His was injected in HBS-P to reach about 50 RU, then two-fold serial dilutions of anti-TfR$^A$/BACE1 (1.95 nM to 1000 nM) or anti-TfR$^D$/BACE1 (9.75 nM to 5000 nM) were injected in HBS-P at 25° C. at a flow rate of approximately 30 μl/min. Association rates ($k_{on}$) and dissociation rates ($k_{off}$) were calculated using a simple one-to-one Langmuir binding model (BIACORE® Evaluation Software version 3.2) by simultaneously fitting the association and dissociation sensorgrams. The equilibrium dissociation constant (Kd) was calculated as the ratio koff/kon. See, e.g., Chen et al., *J. Mol. Biol.* 293:865-881 (1999). The affinity of anti-TfR$^E$/BACE1 was too weak to be determined by surface plasmon resonance.

Figure 9A:
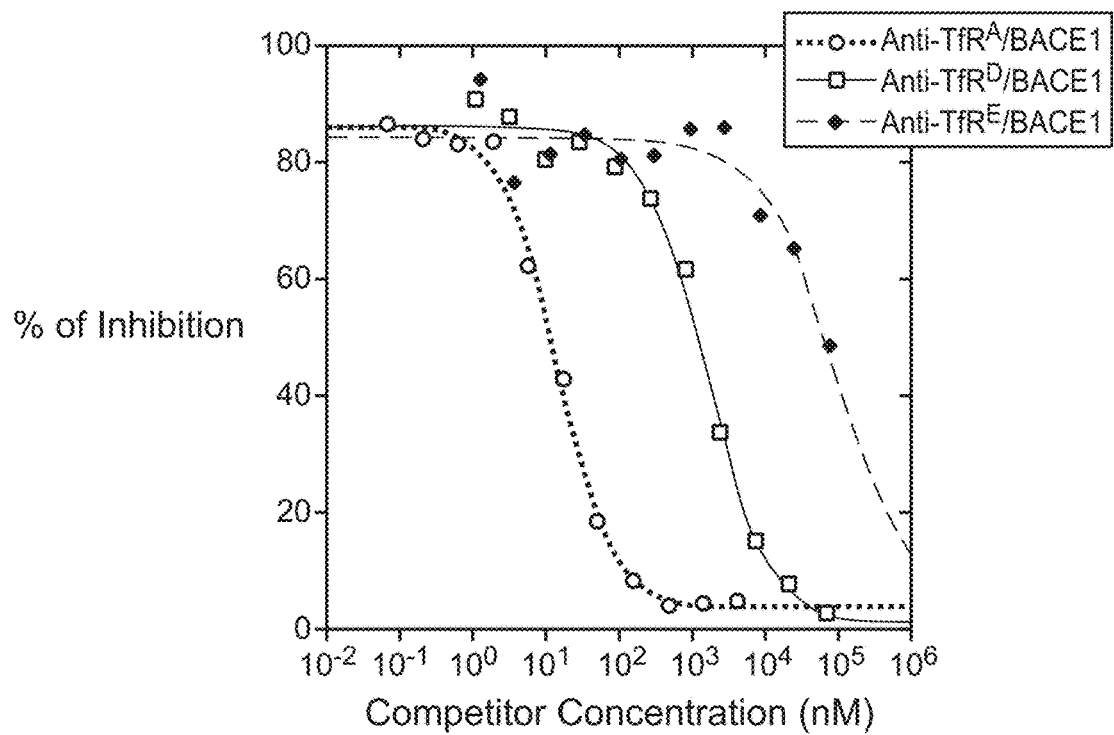
FIGS. 9A-E show the varying degrees to which bispecific anti-TfR$^{A,D,E}$/BACE1 antibodies accumulate in the brain and inhibit Aβ production in vivo.
Figure 9B:
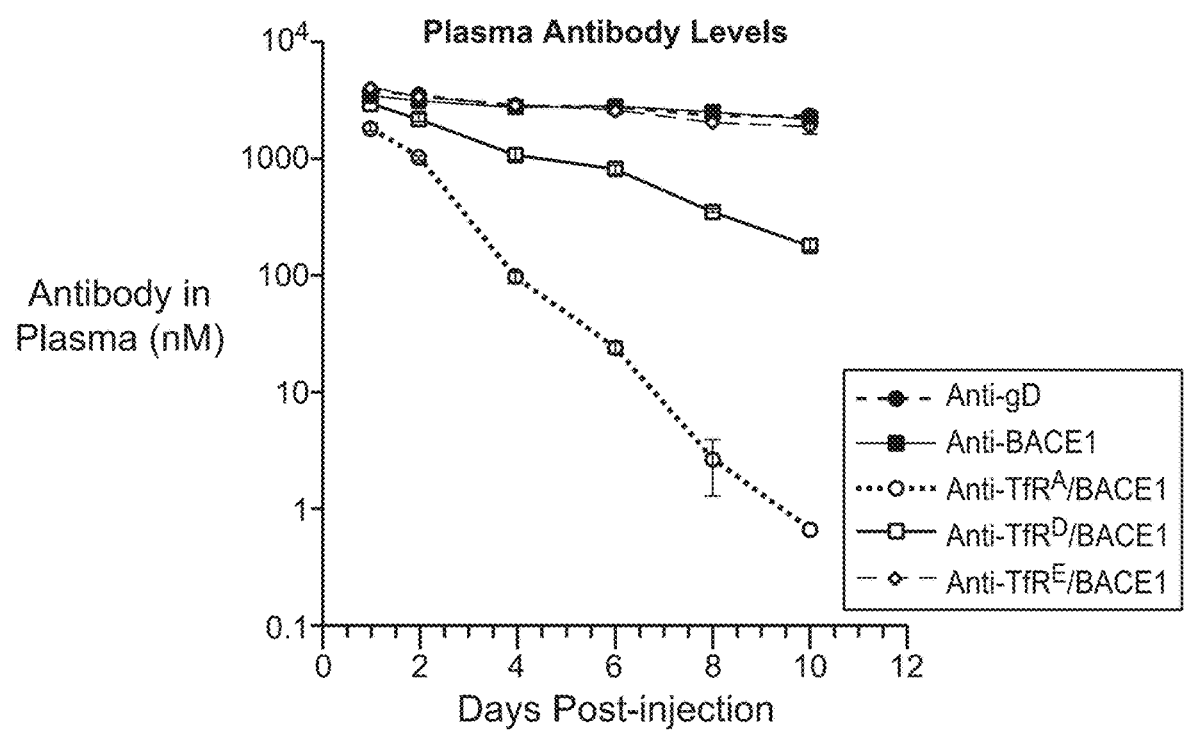

As shown in FIG. 9A and Tables 2 and 3, the bispecific anti-TfR$^A$/BACE1 and anti-TfR$^D$/BACE1 antibodies bound markedly less well to TfR than the corresponding monospecific anti-TfR$^A$ and anti-TfR$^D$ (compare FIG. 9A to FIG. 2A). For anti-TfR$^E$/BACE1, the partial binding curves for the bispecific and monospecific also suggest that the bispecific anti-TfR$^E$/BACE1 has a much higher IC50 than the corresponding monospecific anti-TfR$^E$.

Figure 9C:
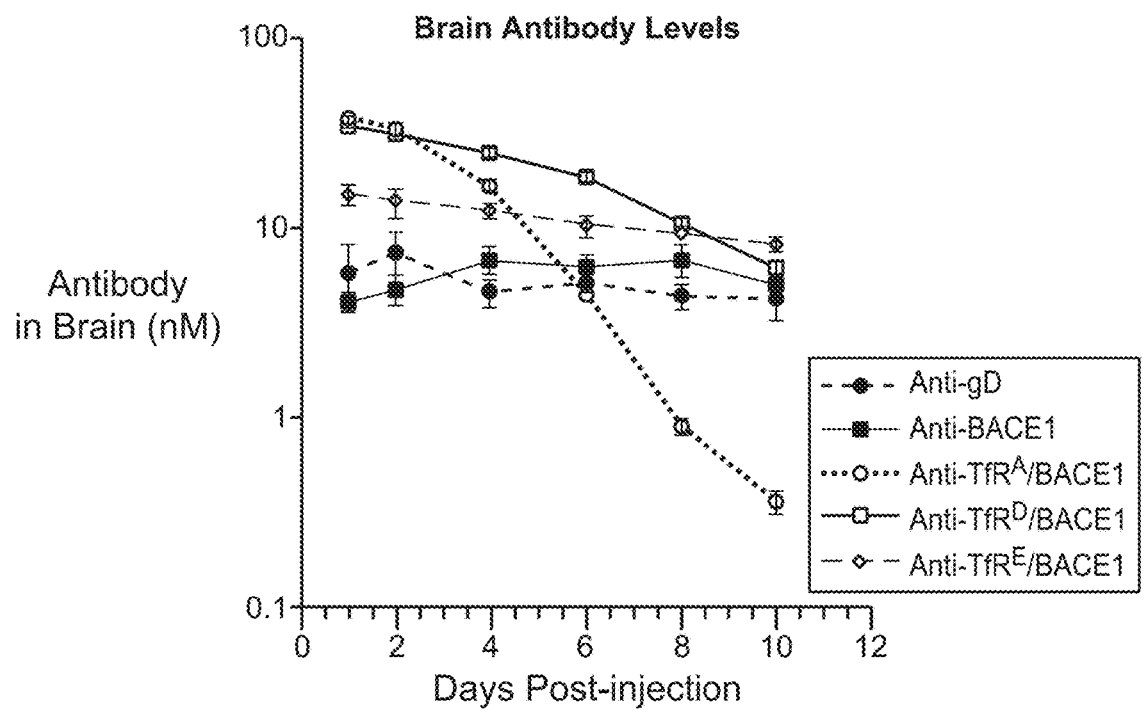
Figure 9D:
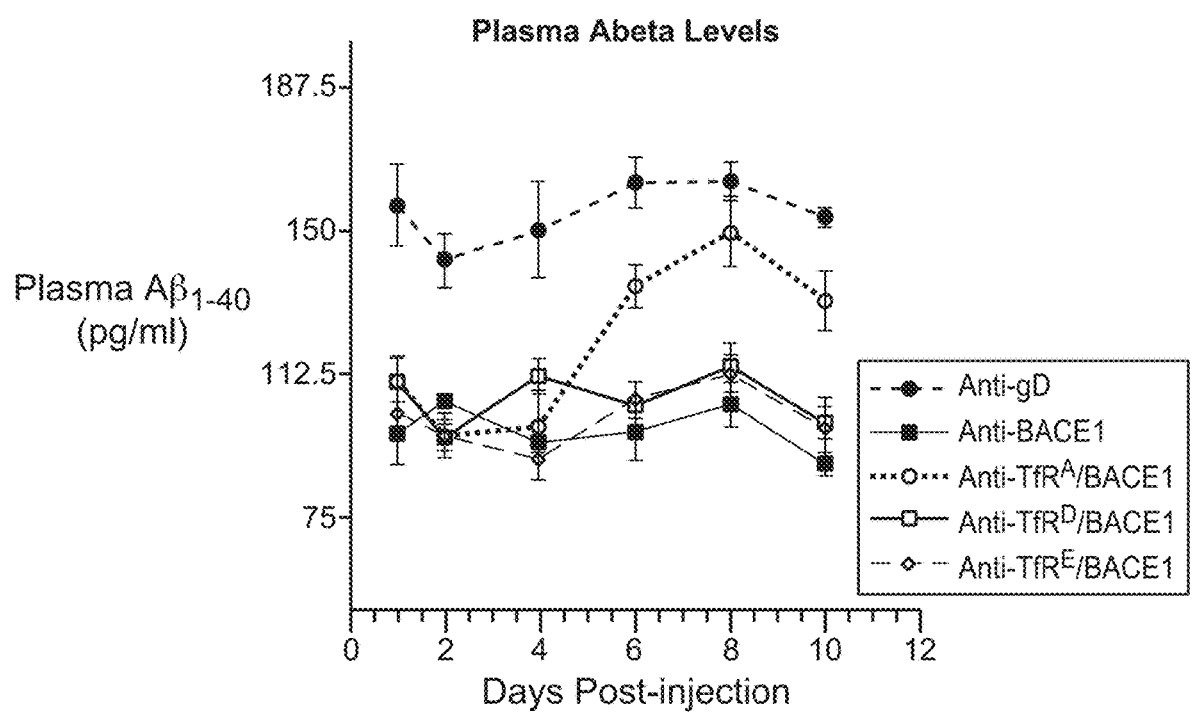
Figure 9E:
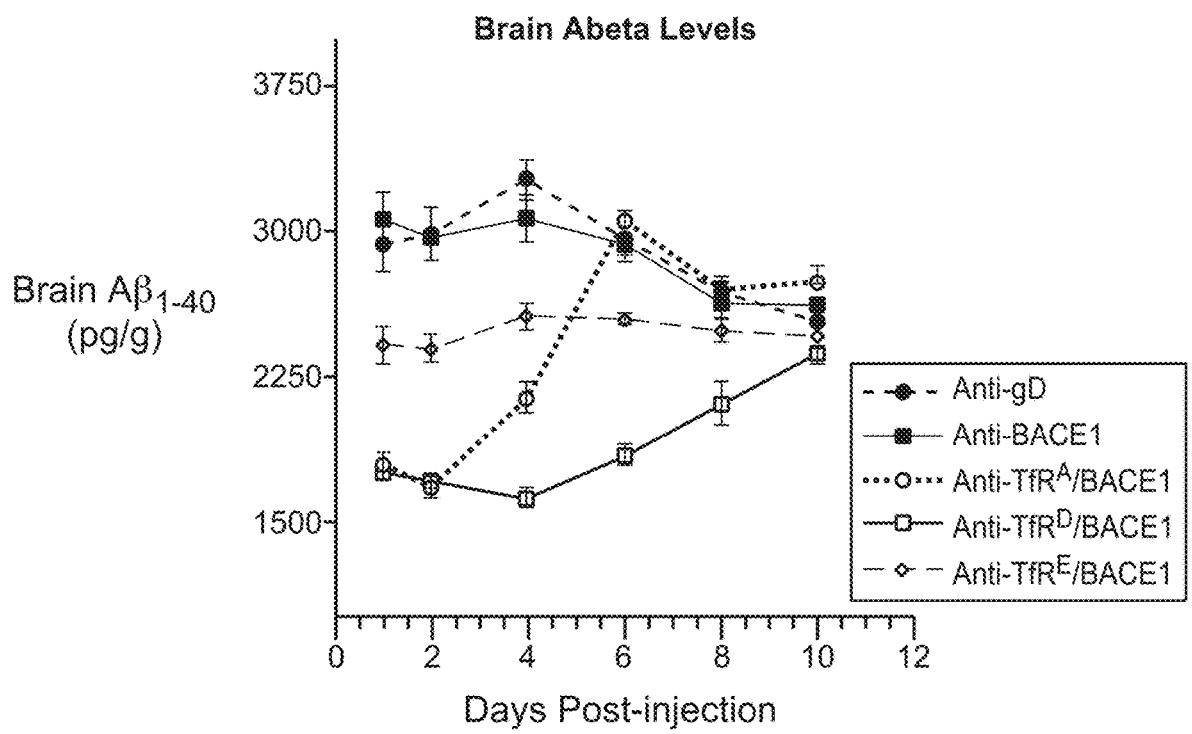

These antibodies were tested in the same in vivo $A\beta_{1-40}$ production assay described above. Briefly, 6-8 week old wild type C57Bl/6 mice were administered via i.v. tail vein injection a single 50 mg/kg dose of control IgG, monospecific anti-BACE1, or anti-TfR$^A$/BACE1, anti-TfR$^D$/BACE1, or anti-TfR$^E$/BACE1, 6 mice per antibody treatment per timepoint, for a total of 180 mice treated. Brain and plasma Aβ$_{1-40}$ levels were determined at 1, 2, 4, 6, 8, and 10 days after i.v. antibody administration (FIGS. 9B-9E). The concentration of bispecific antibodies found in the brain (FIG. 9C) at the earliest time point was greatest with anti-TfR$^A$/BACE1 and anti-TfR$^D$/BACE1, each of which had concentrations of more than twice the concentration achieved by anti-TfR$^E$/BACE1 at the 1 day time point. However, the anti-TfR$^A$/BACE1 brain concentration levels returned to control levels by day 6, and the anti-TfR$^D$/BACE1 levels did so by day 10. In contrast, the lowest affinity bispecific antibody anti-TfR$^E$/BACE1 had a much lower relative dropoff in brain antibody concentration as compared to anti-TfR$^A$/BACE1 and anti-TfR$^D$/BACE1, in keeping with the proposed model that a lower affinity for anti-TfR leads to a reduced ability for the antibody to be exported from the parenchymal space. The levels of Abeta1-40 in the brain (FIG. 9E) were reduced in roughly the same proportion expected by the observed concentrations of bispecific antibody in the brain: anti-TfR$^A$/BACE1 and anti-TfR$^D$/BACE1 had similarly reduced levels of observed brain Abeta1-40 at the earliest time points (days 1-2), which either rapidly increased at subsequent time points (anti-TfR$^A$/BACE1) or more moderately increased at subsequent time points (anti-TfR$^D$/BACE1), consistent with the observed decreases in brain concentration of each of these antibodies (FIG. 9C). Notably, while the anti-TfR$^E$/BACE1 antibody treatment resulted in a relatively more modest reduction in brain Abeta1-40 levels than that observed with the other bispecific antibodies, this reduction was consistent across all timepoints (FIG. 9E).

Plasma measurements (FIG. 9B) showed that anti-TfR$^A$/BACE1 was cleared by day 4, while anti-TfR$^D$/BACE1 persisted at relatively low levels across all time points, and levels of anti-TfR$^E$/BACE1 remained similar to controls across all time points. Consistent with this finding, observed plasma Abeta1-40 levels (FIG. 9D) were similarly reduced from control anti-gD levels at all time points with each of anti-TfR$^D$/BACE1, anti-TfR$^E$/BACE1 and anti-BACE1. Anti-TfR$^A$/BACE1 showed similar reductions at the 1, 2 and 4-day time points, rapidly returning to control levels at later time points, in keeping with the observed disappearance of the antibody from the plasma.

These results again demonstrate that bispecific anti-TfR/BACE1 antibodies effectively cross the BBB and inhibit BACE1 activity in a mammalian in vivo system. They also suggest that an affinity for TfR between that of the anti-TFR$^D$/BACE1 and the anti-TfR$^E$/BACE1 may provide an optimal combination of persistence and activity in the parenchyma/brain. It is noted, however that for each brain target, the potency of the bispecific arm specific for that target will dictate how much of the anti-TfR/target bispecific antibody must be present in the CNS side of the BBB in order to achieve the desired results, and thus what degree of affinity of the anti-TfR for TfR must be used in the bispecific to obtain that concentration. This invention provides a means to determine and design the bispecific antibody to achieve such target levels in the CNS after administration on the nonprivileged side of the BBB.

These results were confirmed and extended using another anti-TfR bispecific antibody, anti-TfR/Abeta, that binds both TfR and amyloid beta. Three bispecific variants were prepared: anti-TfR$^A$/Abeta, anti-TfR$^D$/Abeta and anti-TfR$^E$/Abeta, using the same methods as used for the preparation of the anti-TfR/BACE1 bispecific above. Abeta is the main substituent of amyloid plaques, which are believed to be involved in the development of AD. Inhibition of plaque formation by Abeta binding and removal, in either its free or oligomerized state, may inhibit the development or progression of AD. The pharmacokinetic properties of each of these bispecific antibodies were assessed.

Figure 10A:
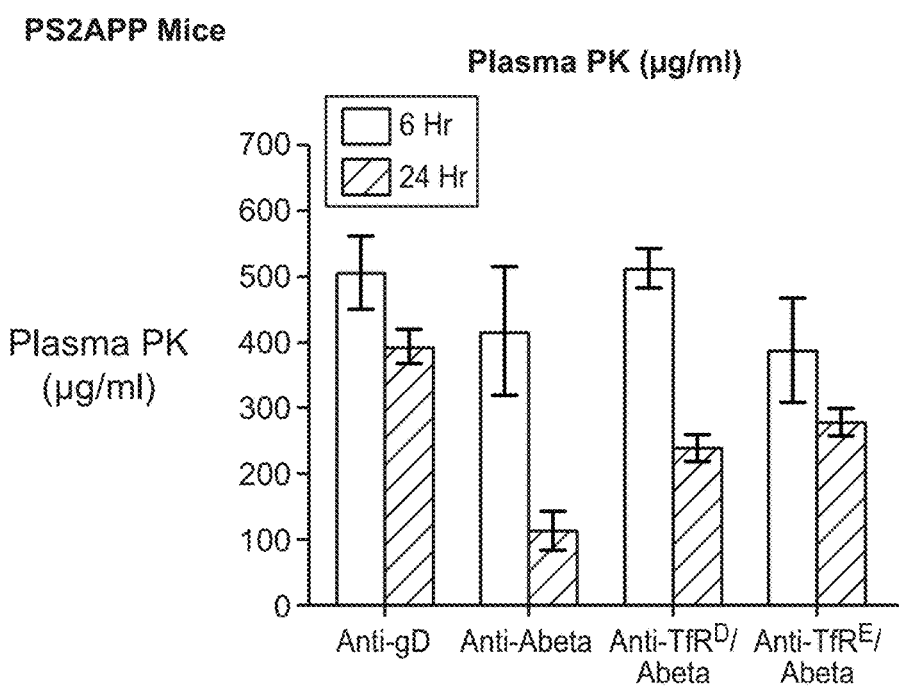
FIGS. 10A-B and 11A-B show the varying degrees to which bispecific anti-TfR$^{A,D,E}$/Abeta antibodies accumulate in the brain of PS2APP mice (FIG. 10) and wild type mice (FIG. 11).
Figure 11A:
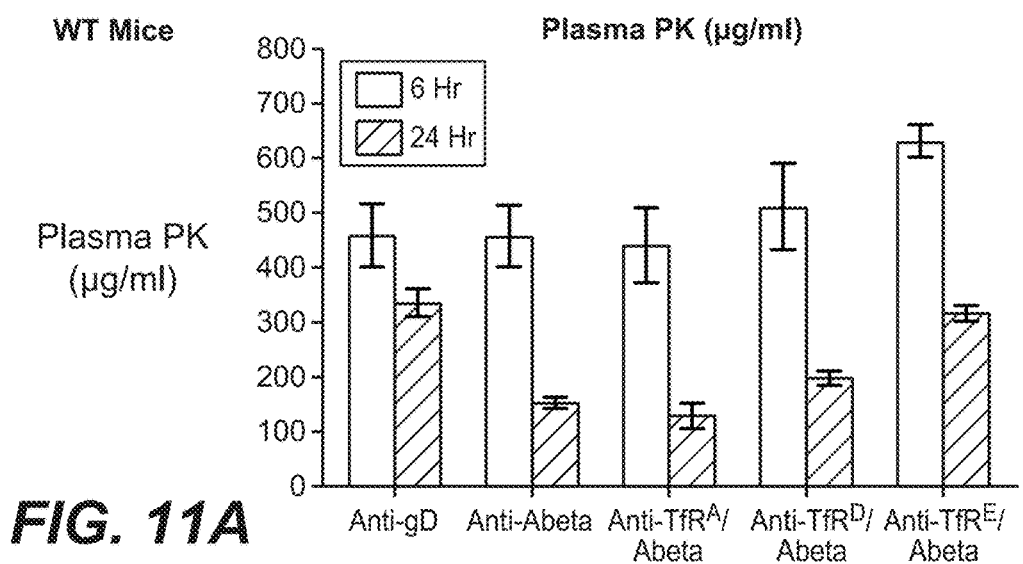

A single 50 mg/kg dose of control IgG, monospecific anti-Abeta antibody, or each bispecific antibody was injected i.p. into 8-16 week old wild type C57BL/6J mice or mice expressing both human presenilin 2 and human amyloid precursor protein (PS2APP). Due to a limited number of transgenic animals, only two of the bispecific variants (anti-TfR$^D$/Abeta and anti-TfR$^E$/Abeta) were assayed in the PS2APP mice. Four to six replicate mice were dosed in each treatment group. The mice were sacrificed after 24 hours and drug levels measured in both the brain and plasma, as with the anti-TfR/BACE1 bispecific studies. Prior to sacrifice, blood was also collected 6 hours post-dose for an early evaluation of plasma antibody concentrations. Plasma measurements of antibody concentration (FIGS. 10A and 11A) showed that all antibodies were present at similar levels at 6 hours post-dose. However, control monospecific anti-Abeta levels were reduced compared to control IgG by 24 hours. This is similar to previous observations for this anti-Abeta molecule. At 24 hours, anti-TfR$^A$/Abeta showed similar antibody levels in the periphery as anti-Abeta, whereas anti-TfR$^D$/Abeta and anti-TfR$^E$/Abeta showed slightly elevated levels, intermediate between anti-Abeta and control IgG.

Figure 10B:
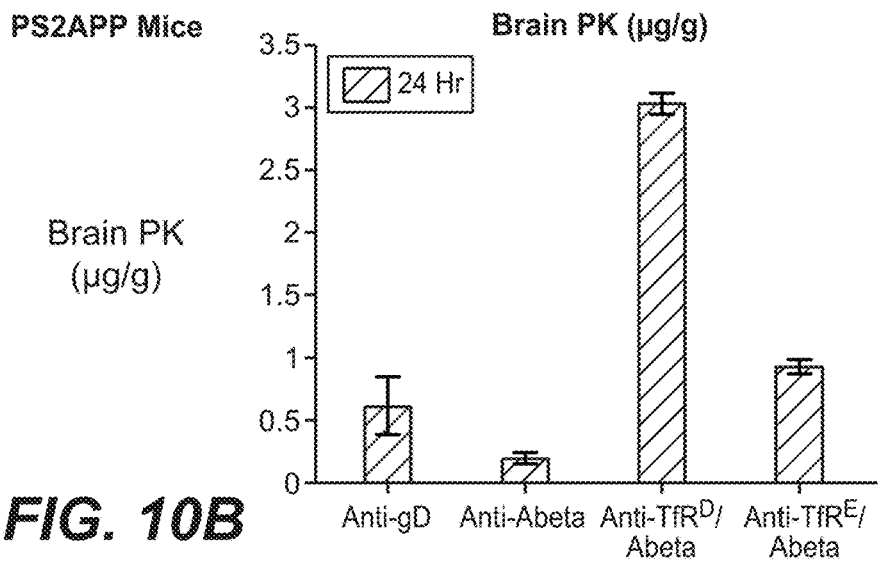
Figure 11B:
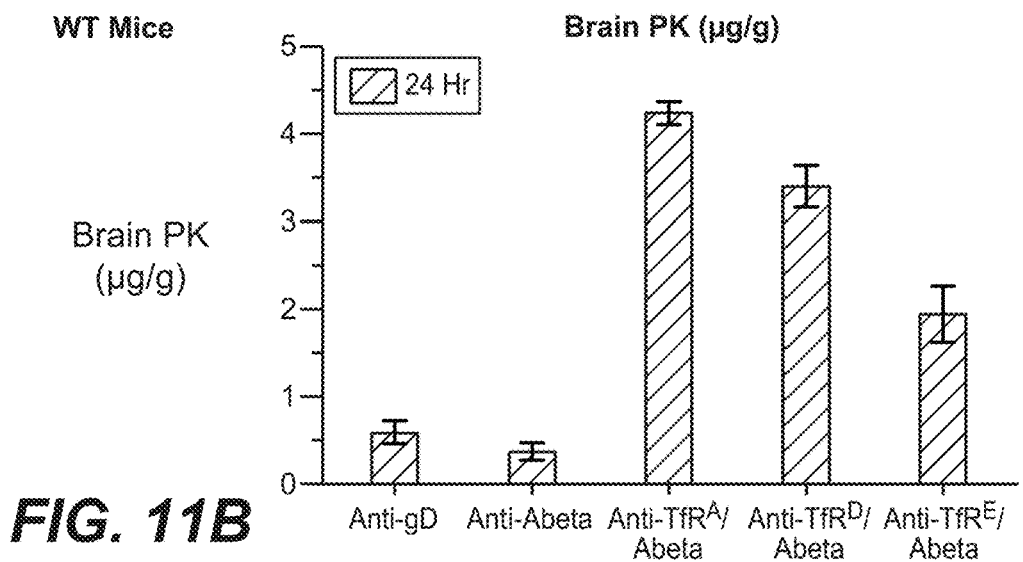

The concentration of bispecific antibodies found in the brain was increased compared to both control IgG and anti-Abeta (FIGS. 10B and 11B). As compared to anti-Abeta, anti-TfR$^A$/Abeta had concentrations 12-fold higher, anti-TfR$^D$/Abeta had concentrations 8- to 15-fold higher, and anti-TfR$^E$/Abeta had concentrations 4- to 5-fold higher. The increase in brain uptake of the anti-TfR$^{A,D,E}$/Abeta antibodies compared to anti-Abeta was even greater than the increases seen for the anti-TfR$^{A,D,E}$/BACE bispecific antibodies compared to anti-BACE1. This is likely due to the decreased peripheral exposure of anti-Abeta compared to control IgG 24 hours after dosing, which resulted in lower levels of anti-Abeta in brain as compared to control IgG.

These findings are the first demonstration that large molecule antibodies administered at therapeutically relevant doses can traverse the BBB and produce significant and sustained brain uptake. Furthermore, these results demonstrating an inverse relationship between antibody affinity and extent of brain uptake furthers understanding of RMT dynamics. This novel insight can be applied to a variety of other potential RMT targets to provide a more effective strategy for antibody drug delivery into the CNS. Additionally, these in vivo results demonstrate that a bispecific antibody can greatly improve the potency of a promising anti-amyloidogenic therapeutic by significantly increasing brain penetrance of the targeting antibody drug. This could be highly advantageous, as enhanced drug delivery would translate to less potential side effects due to lower therapeutic dosing required. More generally, this technology has vast potential to be applied to therapeutics for a wide range of CNS diseases and represents an improved approach to provide safer antibody drugs.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method of making an antibody useful for transporting a compound across the BBB comprising selecting an antibody specific for a transferrin receptor (TfR) with an affinity from 20 nM to 10 μM for the TfR and coupling the antibody to a compound, wherein the antibody comprises at least a portion of an immunoglobulin constant region.

2. A method of lowering the affinity of an antibody that binds to a transferrin receptor (TfR) of a mammal and comprises at least a portion of an immunoglobulin constant region, the method comprising: mutating a codon encoding a hypervariable region residue of the antibody, thereby producing a nucleic acid encoding an altered antibody, wherein the altered antibody has an affinity from 20 nM to 10 μM for the TfR.

3. The method of claim 2, further comprising expressing the altered antibody.

4. The method of claim 3, further comprising coupling the altered antibody to a compound.

5. The method of claim 4, wherein the compound is a neurological disorder drug or an imaging agent.

6. The method of claim 5, wherein the neurological disorder drug is a drug that treats Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, or traumatic brain injury.

7. The method of claim 2, wherein the altered antibody is a multispecific antibody.

8. The method of claim 2, wherein the altered antibody comprises an additional antigen-binding site that binds a brain antigen.

9. The method of claim 8, wherein the brain antigen is beta-secretase 1 (BACE1), Abeta, epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), and caspase 6.

10. The method of claim 9, wherein the brain antigen is BACE1.

11. The method of claim 9, wherein brain antigen is Abeta.

12. The method of claim 2, wherein the hypervariable region residue to be mutated is identified using alanine scanning mutagenesis.

13. The method of claim 2, wherein the hypervariable region residue to be mutated is identified by structural analysis of an antibody-antigen complex comprising the antibody.

14. The method of claim 2, wherein the altered antibody has an affinity for the TfR from about 20 nM to about 1 μM.

15. The method of claim 2, wherein the altered antibody has an affinity for the TfR from about 100 nM to about 10 μM.

16. The method of claim 2, wherein the antibody does not inhibit the binding of TfR to transferrin.

* * * * *

SEQUENCE LISTING

<160> NUMBER OF SEQ ID NOS: 15

<210> SEQ ID NO 1
<211> LENGTH: 108
<212> TYPE: PRT
<213> ORGANISM: Artificial sequence
<220> FEATURE:
<223> OTHER INFORMATION: sequence is synthesized

<400> SEQUENCE: 1

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
            35                  40                  45

Leu Leu Ile Tyr Ser Ala Ser Phe Leu Tyr Ser Gly Val Pro Ser
        50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Ser Tyr Thr Thr Pro Pro Thr Phe Gly Gln Gly Thr Lys Val Glu
                95                  100                 105

Ile Lys Arg

<210> SEQ ID NO 2
<211> LENGTH: 108
<212> TYPE: PRT
<213> ORGANISM: Artificial sequence
<220> FEATURE:
<223> OTHER INFORMATION: sequence is synthesized

<400> SEQUENCE: 2

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
            35                  40                  45

Leu Leu Ile Tyr Ser Ala Ser Phe Leu Tyr Ser Gly Val Pro Ser
        50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Phe Pro Thr Tyr Leu Pro Thr Phe Gly Gln Gly Thr Lys Val Glu
                95                  100                 105

Ile Lys Arg

<210> SEQ ID NO 3
<211> LENGTH: 108
<212> TYPE: PRT
<213> ORGANISM: Artificial sequence
<220> FEATURE:

<223> OTHER INFORMATION: sequence is synthesized

<400> SEQUENCE: 3

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Ser
            20                  25                  30

Thr Ala Val Ala Trp Tyr Gln Gln Lys Pro Gly Lys Ala Pro Lys
        35                  40                  45

Leu Leu Ile Tyr Ser Ala Ser Phe Leu Tyr Ser Gly Val Pro Ser
    50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Gly Tyr Asn Asp Pro Pro Thr Phe Gly Gln Gly Thr Lys Val Glu
            95                  100                 105

Ile Lys Arg

<210> SEQ ID NO 4
<211> LENGTH: 108
<212> TYPE: PRT
<213> ORGANISM: Artificial sequence
<220> FEATURE:
<223> OTHER INFORMATION: sequence is synthesized

<400> SEQUENCE: 4

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Ser
            20                  25                  30

Thr Ala Val Ala Trp Tyr Gln Gln Lys Pro Gly Lys Ala Pro Lys
        35                  40                  45

Leu Leu Ile Tyr Ser Ala Ser Phe Leu Tyr Ser Gly Val Pro Ser
    50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Ser Ser Thr Asp Pro Thr Thr Phe Gly Gln Gly Thr Lys Val Glu
            95                  100                 105

Ile Lys Arg

<210> SEQ ID NO 5
<211> LENGTH: 108
<212> TYPE: PRT
<213> ORGANISM: Artificial sequence
<220> FEATURE:
<223> OTHER INFORMATION: sequence is synthesized

<400> SEQUENCE: 5

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Val Val Ala
            20                  25                  30

Asn Ser Leu Ala Trp Tyr Gln Gln Lys Pro Gly Lys Ala Pro Lys
        35                  40                  45

Leu Leu Ile Tyr Leu Ala Ser Phe Leu Tyr Ser Gly Val Pro Ser
        50                  55                  60

Arg Phe Ser Gly Ser Gly Ser Gly Thr Asp Phe Thr Leu Thr Ile
 65                  70                  75

Ser Ser Leu Gln Pro Glu Asp Phe Ala Thr Tyr Tyr Cys Gln Gln
                 80                  85                  90

Asp Ala Thr Ser Pro Pro Thr Phe Gly Gln Gly Thr Lys Val Glu
                 95                 100                 105

Ile Lys Arg

<210> SEQ ID NO 6
<211> LENGTH: 108
<212> TYPE: PRT
<213> ORGANISM: Artificial sequence
<220> FEATURE:
<223> OTHER INFORMATION: sequence is synthesized

<400> SEQUENCE: 6

Asp Ile Gln Met Thr Gln Ser Pro Ser Ser Leu Ser Ala Ser Val
 1                   5                  10                  15

Gly Asp Arg Val Thr Ile Thr Cys Arg Ala Ser Gln Asp Val Ser
                 20                  25                  30

Thr Ala Val Ala Trp Tyr Gln Gln Lys Pro Gly Lys Ala Pro Lys
             35                  40                  45

Leu Leu Ile Tyr Ser Ala Ser Phe Leu Tyr Ser Gly Val Pro Ser
        50                  55                  60

Arg Phe Ser Gly Ser Gly Ser Gly Thr Asp Phe Thr Leu Thr Ile
 65                  70                  75

Ser Ser Leu Gln Pro Glu Asp Phe Ala Thr Tyr Tyr Cys Gln Gln
                 80                  85                  90

Tyr Ala Thr Asp Pro Pro Thr Phe Gly Gln Gly Thr Lys Val Glu
                 95                 100                 105

Ile Lys Arg

<210> SEQ ID NO 7
<211> LENGTH: 119
<212> TYPE: PRT
<213> ORGANISM: Artificial sequence
<220> FEATURE:
<223> OTHER INFORMATION: sequence is synthesized

<400> SEQUENCE: 7

Glu Val Gln Leu Val Glu Ser Gly Gly Gly Leu Val Gln Pro Gly
 1                   5                  10                  15

Gly Ser Leu Arg Leu Ser Cys Ala Ala Ser Gly Phe Thr Phe Ser
                 20                  25                  30

Gly Tyr Ala Ile His Trp Val Arg Gln Ala Pro Gly Lys Gly Leu
             35                  40                  45

Glu Trp Val Gly Trp Ile Ser Pro Ala Gly Gly Ser Thr Asp Tyr
        50                  55                  60

Ala Asp Ser Val Lys Gly Arg Phe Thr Ile Ser Ala Asp Thr Ser
 65                  70                  75

Lys Asn Thr Ala Tyr Leu Gln Met Asn Ser Leu Arg Ala Glu Asp
                 80                  85                  90

Thr Ala Val Tyr Tyr Cys Ala Arg Gly Pro Phe Ser Pro Trp Val
                 95                 100                 105

Met Asp Tyr Trp Gly Gln Gly Thr Leu Val Thr Val Ser Ser

<210> SEQ ID NO 8
<211> LENGTH: 119
<212> TYPE: PRT
<213> ORGANISM: Artificial sequence
<220> FEATURE:
<223> OTHER INFORMATION: sequence is synthesized

<400> SEQUENCE: 8

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Leu
            20                  25                  30

Gly Tyr Gly Ile His Trp Val Arg Gln Ala Pro Gly Lys Gly Leu
        35                  40                  45

Glu Trp Val Gly Trp Ile Ser Pro Ala Gly Gly Ser Thr Asp Tyr
    50                  55                  60

Ala Asp Ser Val Lys Gly Arg Phe Thr Ile Ser Ala Asp Thr Ser
65                  70                  75

Lys Asn Thr Ala Tyr Leu Gln Met Asn Ser Leu Arg Ala Glu Asp
                80                  85                  90

Thr Ala Val Tyr Tyr Cys Ala Arg Gly Pro Phe Ser Pro Trp Val
            95                  100                 105

Met Asp Tyr Trp Gly Gln Gly Thr Leu Val Thr Val Ser Ser
        110                 115

<210> SEQ ID NO 9
<211> LENGTH: 108
<212> TYPE: PRT
<213> ORGANISM: Artificial sequence
<220> FEATURE:
<223> OTHER INFORMATION: sequence is synthesized

<400> SEQUENCE: 9

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Val Ser
            20                  25                  30

Ser Ala Val Ala Trp Tyr Gln Gln Lys Pro Gly Lys Ala Pro Lys
        35                  40                  45

Leu Leu Ile Tyr Ser Ala Ser Ser Leu Tyr Ser Gly Val Pro Ser
    50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Tyr Ser Tyr Ser Pro Phe Thr Phe Gly Gln Gly Thr Lys Val Glu
            95                  100                 105

Ile Lys Arg

<210> SEQ ID NO 10
<211> LENGTH: 108
<212> TYPE: PRT
<213> ORGANISM: Artificial sequence
<220> FEATURE:
<223> OTHER INFORMATION: sequence is synthesized

<400> SEQUENCE: 10

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Val Ser
            20                  25                  30

Ser Ala Val Ala Trp Tyr Gln Gln Lys Pro Gly Lys Ala Pro Lys
        35                  40                  45

Leu Leu Ile Ser Trp Ala Ser Trp Leu Tyr Ser Gly Val Pro Ser
    50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
            80                  85                  90

Tyr Ser Tyr Ser Pro Phe Thr Phe Gly Gln Gly Thr Lys Val Glu
        95                  100                 105

Ile Lys Arg

<210> SEQ ID NO 11
<211> LENGTH: 108
<212> TYPE: PRT
<213> ORGANISM: Artificial sequence
<220> FEATURE:
<223> OTHER INFORMATION: sequence is synthesized

<400> SEQUENCE: 11

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Val Ser
            20                  25                  30

Ser Ala Val Ala Trp Tyr Gln Gln Lys Pro Gly Lys Ala Pro Lys
        35                  40                  45

Leu Leu Ile Trp Tyr Ala Ser Trp Leu Tyr Ser Gly Val Pro Ser
    50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
            80                  85                  90

Tyr Ser Tyr Ser Pro Phe Thr Phe Gly Gln Gly Thr Lys Val Glu
        95                  100                 105

Ile Lys Arg

<210> SEQ ID NO 12
<211> LENGTH: 108
<212> TYPE: PRT
<213> ORGANISM: Artificial sequence
<220> FEATURE:
<223> OTHER INFORMATION: sequence is synthesized

<400> SEQUENCE: 12

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Val Ser
            20                  25                  30

Ser Ala Val Ala Trp Tyr Gln Gln Lys Pro Gly Lys Ala Pro Lys
        35                  40                  45

Leu Leu Ile Trp Trp Ala Ser Ser Leu Tyr Ser Gly Val Pro Ser
    50                  55                  60

Arg Phe Ser Gly Ser Gly Ser Gly Thr Asp Phe Thr Leu Thr Ile

```
                65                  70                  75
Ser Ser Leu Gln Pro Glu Asp Phe Ala Thr Tyr Tyr Cys Gln Gln
                    80                  85                  90

Tyr Ser Tyr Ser Pro Phe Thr Phe Gly Gln Gly Thr Lys Val Glu
                95                 100                 105

Ile Lys Arg

<210> SEQ ID NO 13
<211> LENGTH: 126
<212> TYPE: PRT
<213> ORGANISM: Artificial sequence
<220> FEATURE:
<223> OTHER INFORMATION: sequence is synthesized

<400> SEQUENCE: 13

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Asn Phe Tyr
                20                  25                  30

Tyr Ser Ser Ile His Trp Val Arg Gln Ala Pro Gly Lys Gly Leu
            35                  40                  45

Glu Trp Val Ala Ser Ile Ser Pro Tyr Ser Gly Tyr Thr Ser Tyr
    50                  55                  60

Ala Asp Ser Val Lys Gly Arg Phe Thr Ile Ser Ala Asp Thr Ser
65                  70                  75

Lys Asn Thr Ala Tyr Leu Gln Met Asn Ser Leu Arg Ala Glu Asp
                80                  85                  90

Thr Ala Val Tyr Tyr Cys Ala Arg Gln Pro Thr His Tyr Tyr Tyr
                95                 100                 105

Tyr Ala Lys Gly Tyr Lys Ala Met Asp Tyr Trp Gly Gln Gly Thr
            110                 115                 120

Leu Val Thr Val Ser Ser
        125

<210> SEQ ID NO 14
<211> LENGTH: 438
<212> TYPE: PRT
<213> ORGANISM: Artificial sequence
<220> FEATURE:
<223> OTHER INFORMATION: sequence is synthesized

<400> SEQUENCE: 14

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser
                20                  25                  30

Ser Tyr Gly Met Ser Trp Val Arg Gln Ala Pro Gly Lys Gly Leu
            35                  40                  45

Glu Leu Val Ala Ser Ile Asn Ser Asn Gly Gly Ser Thr Tyr Tyr
    50                  55                  60

Pro Asp Ser Val Lys Gly Arg Phe Thr Ile Ser Arg Asp Asn Ala
65                  70                  75

Lys Asn Ser Leu Tyr Leu Gln Met Asn Ser Leu Arg Ala Glu Asp
                80                  85                  90

Thr Ala Val Tyr Tyr Cys Ala Ser Gly Asp Tyr Trp Gly Gln Gly
                95                 100                 105

Thr Thr Val Thr Val Ser Ser Ala Ser Thr Lys Gly Pro Ser Val
```

```
            110                 115                 120
Phe Pro Leu Ala Pro Cys Ser Arg Ser Thr Ser Glu Ser Thr Ala
        125                 130                 135
Ala Leu Gly Cys Leu Val Lys Asp Tyr Phe Pro Glu Pro Val Thr
140                 145                 150
Val Ser Trp Asn Ser Gly Ala Leu Thr Ser Gly Val His Thr Phe
                155                 160                 165
Pro Ala Val Leu Gln Ser Ser Gly Leu Tyr Ser Leu Ser Ser Val
            170                 175                 180
Val Thr Val Pro Ser Ser Ser Leu Gly Thr Lys Thr Tyr Thr Cys
                185                 190                 195
Asn Val Asp His Lys Pro Ser Asn Thr Lys Val Asp Lys Arg Val
200                 205                 210
Glu Ser Lys Tyr Gly Pro Pro Cys Pro Pro Cys Pro Ala Pro Glu
215                 220                 225
Phe Leu Gly Gly Pro Ser Val Phe Leu Phe Pro Pro Lys Pro Lys
                230                 235                 240
Asp Thr Leu Met Ile Ser Arg Thr Pro Glu Val Thr Cys Val Val
                245                 250                 255
Val Asp Val Ser Gln Glu Asp Pro Glu Val Gln Phe Asn Trp Tyr
            260                 265                 270
Val Asp Gly Val Glu Val His Asn Ala Lys Thr Lys Pro Arg Glu
        275                 280                 285
Glu Gln Phe Asn Ser Thr Tyr Arg Val Val Ser Val Leu Thr Val
290                 295                 300
Leu His Gln Asp Trp Leu Asn Gly Lys Glu Tyr Lys Cys Lys Val
                305                 310                 315
Ser Asn Lys Gly Leu Pro Ser Ser Ile Glu Lys Thr Ile Ser Lys
            320                 325                 330
Ala Lys Gly Gln Pro Arg Glu Pro Gln Val Tyr Thr Leu Pro Pro
        335                 340                 345
Ser Gln Glu Glu Met Thr Lys Asn Gln Val Ser Leu Thr Cys Leu
    350                 355                 360
Val Lys Gly Phe Tyr Pro Ser Asp Ile Ala Val Glu Trp Glu Ser
365                 370                 375
Asn Gly Gln Pro Glu Asn Asn Tyr Lys Thr Thr Pro Pro Val Leu
                380                 385                 390
Asp Ser Asp Gly Ser Phe Phe Leu Tyr Ser Arg Leu Thr Val Asp
            395                 400                 405
Lys Ser Arg Trp Gln Glu Gly Asn Val Phe Ser Cys Ser Val Met
        410                 415                 420
His Glu Ala Leu His Asn His Tyr Thr Gln Lys Ser Leu Ser Leu
    425                 430                 435
Ser Leu Gly

<210> SEQ ID NO 15
<211> LENGTH: 219
<212> TYPE: PRT
<213> ORGANISM: Artificial sequence
<220> FEATURE:
<223> OTHER INFORMATION: sequence is synthesized

<400> SEQUENCE: 15

Asp Ile Val Met Thr Gln Ser Pro Leu Ser Leu Pro Val Thr Pro
1               5                   10                  15
```

```
Gly Glu Pro Ala Ser Ile Ser Cys Arg Ser Ser Gln Ser Leu Val
            20                  25                  30

Tyr Ser Asn Gly Asp Thr Tyr Leu His Trp Tyr Leu Gln Lys Pro
        35                  40                  45

Gly Gln Ser Pro Gln Leu Leu Ile Tyr Lys Val Ser Asn Arg Phe
    50                  55                  60

Ser Gly Val Pro Asp Arg Phe Ser Gly Ser Gly Ser Gly Thr Asp
65                  70                  75

Phe Thr Leu Lys Ile Ser Arg Val Glu Ala Glu Asp Val Gly Val
            80                  85                  90

Tyr Tyr Cys Ser Gln Ser Thr His Val Pro Trp Thr Phe Gly Gln
            95                  100                 105

Gly Thr Lys Val Glu Ile Lys Arg Thr Val Ala Ala Pro Ser Val
            110                 115                 120

Phe Ile Phe Pro Pro Ser Asp Glu Gln Leu Lys Ser Gly Thr Ala
            125                 130                 135

Ser Val Val Cys Leu Leu Asn Asn Phe Tyr Pro Arg Glu Ala Lys
140                 145                 150

Val Gln Trp Lys Val Asp Asn Ala Leu Gln Ser Gly Asn Ser Gln
            155                 160                 165

Glu Ser Val Thr Glu Gln Asp Ser Lys Asp Ser Thr Tyr Ser Leu
            170                 175                 180

Ser Ser Thr Leu Thr Leu Ser Lys Ala Asp Tyr Glu Lys His Lys
            185                 190                 195

Val Tyr Ala Cys Glu Val Thr His Gln Gly Leu Ser Ser Pro Val
            200                 205                 210

Thr Lys Ser Phe Asn Arg Gly Glu Cys
215
```